(12) United States Patent
Li et al.

(10) Patent No.: US 11,608,337 B2
(45) Date of Patent: Mar. 21, 2023

(54) HETEROCYCLIC COMPOUNDS AS IMMUNOMODULATORS

(71) Applicant: Incyte Corporation, Wilmington, DE (US)

(72) Inventors: Zhenwu Li, Wilmington, DE (US); Liangxing Wu, Wilmington, DE (US); Wenqing Yao, Chadds Ford, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 17/032,603

(22) Filed: Sep. 25, 2020

(65) Prior Publication Data

US 2021/0017175 A1    Jan. 21, 2021

Related U.S. Application Data

(63) Continuation of application No. 16/781,927, filed on Feb. 4, 2020, now abandoned, which is a continuation of application No. 16/444,797, filed on Jun. 18, 2019, now abandoned, which is a continuation of application No. 16/170,827, filed on Oct. 25, 2018, now abandoned, which is a continuation of application No. 15/906,655, filed on Feb. 27, 2018, now abandoned, which is a continuation of application No. 15/587,466, filed on May 5, 2017, now abandoned.

(60) Provisional application No. 62/332,655, filed on May 6, 2016.

(51) Int. Cl.
| | | |
|---|---|---|
| C07D 513/04 | (2006.01) | |
| C07D 471/04 | (2006.01) | |
| C07D 498/04 | (2006.01) | |
| C07D 487/04 | (2006.01) | |

(52) U.S. Cl.
CPC ......... *C07D 471/04* (2013.01); *C07D 487/04* (2013.01); *C07D 498/04* (2013.01); *C07D 513/04* (2013.01)

(58) Field of Classification Search
CPC .................................................. C07D 513/04
See application file for complete search history.

(56) References Cited

U.S. PATENT DOCUMENTS

| | | | |
|---|---|---|---|
| 3,272,781 | A | 9/1966 | Goodrow |
| 4,208,328 | A | 6/1980 | Lavallee et al. |
| 4,789,711 | A | 12/1988 | Monnier et al. |
| 5,077,164 | A | 12/1991 | Ueda et al. |
| 6,114,497 | A | 9/2000 | Tada et al. |
| 6,297,351 | B1 | 10/2001 | Murayama et al. |
| 6,372,907 | B1 | 4/2002 | Lee et al. |
| 6,521,618 | B2 | 2/2003 | Boschelli et al. |
| 6,867,200 | B1 | 3/2005 | Allen et al. |
| 7,320,989 | B2 | 1/2008 | Anderson et al. |
| 7,417,065 | B2 | 8/2008 | Mi et al. |
| 7,491,245 | B2 | 2/2009 | Glenn et al. |
| 7,691,870 | B2 | 4/2010 | Buchstaller et al. |
| 7,851,489 | B2 | 12/2010 | Borzilleri et al. |
| 8,163,743 | B2 | 4/2012 | Baldwin et al. |
| 8,541,424 | B2 | 9/2013 | DeGoey et al. |
| 8,993,604 | B2 | 3/2015 | Byrd et al. |
| 9,085,576 | B2 | 7/2015 | Minatti et al. |
| 9,163,017 | B2 | 10/2015 | DeGoey et al. |
| 9,394,365 | B1 | 7/2016 | Eisenbach-Schwartz et al. |
| 9,540,322 | B2 | 1/2017 | Jorgensen et al. |
| 9,611,261 | B2 | 4/2017 | Minatti et al. |
| 9,643,922 | B2 | 5/2017 | Jorgensen et al. |
| 10,017,520 | B2 | 7/2018 | Koehler et al. |
| 10,202,343 | B2 | 2/2019 | Jorgensen et al. |
| 10,308,644 | B2 | 6/2019 | Wu et al. |
| 10,618,916 | B2 | 4/2020 | Wu et al. |
| 10,669,271 | B2 | 6/2020 | Wu et al. |
| 10,793,505 | B2 | 10/2020 | Wu et al. |
| 10,793,565 | B2 | 10/2020 | Wu et al. |
| 10,800,768 | B2 | 10/2020 | Wu et al. |
| 10,806,785 | B2 | 10/2020 | Liu et al. |
| 10,906,920 | B2 | 2/2021 | Wu et al. |
| 11,124,511 | B2 | 9/2021 | Wu et al. |
| 11,339,149 | B2 | 5/2022 | Wu et al. |
| 11,401,279 | B2 | 8/2022 | Li et al. |
| 11,407,749 | B2 | 8/2022 | Wu et al. |
| 11,414,433 | B2 | 8/2022 | Wu et al. |
| 11,465,981 | B2 | 10/2022 | Wu et al. |

(Continued)

FOREIGN PATENT DOCUMENTS

| | | |
|---|---|---|
| CA | 2355249 | 6/2000 |
| CA | 3099994 | 11/2019 |

(Continued)

OTHER PUBLICATIONS

Camara et al., "Multiple dermatofibromas: Dermoscopic patterns," Indian journal of dermatology, 2013, 58(3):243.

(Continued)

*Primary Examiner* — Brian E McDowell
(74) *Attorney, Agent, or Firm* — Fish & Richardson P.C.

(57) ABSTRACT

Disclosed are compounds of Formula (I), methods of using the compounds as immunomodulators, and pharmaceutical compositions comprising such compounds. The compounds are useful in treating, preventing or ameliorating diseases or disorders such as cancer or infections.

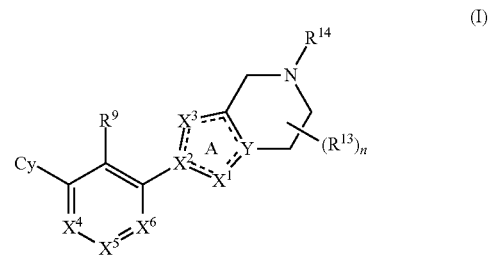

(I)

22 Claims, No Drawings

(56) References Cited

U.S. PATENT DOCUMENTS

| | | |
|---|---|---|
| 2002/0082266 A1 | 6/2002 | Gallant et al. |
| 2003/0134843 A1 | 7/2003 | Lubisch et al. |
| 2003/0191115 A1 | 10/2003 | Pinto et al. |
| 2004/0018986 A1 | 1/2004 | Pitlik et al. |
| 2004/0058938 A1 | 3/2004 | Cullmann et al. |
| 2004/0063963 A1 | 4/2004 | Ueno et al. |
| 2004/0082635 A1 | 4/2004 | Hashimoto et al. |
| 2004/0186114 A1 | 9/2004 | Cirillo et al. |
| 2004/0214040 A1 | 10/2004 | Lee et al. |
| 2005/0187230 A1 | 8/2005 | Ding et al. |
| 2005/0245536 A1 | 11/2005 | Hao et al. |
| 2005/0260126 A1 | 11/2005 | Kudo et al. |
| 2005/0288295 A1 | 12/2005 | Currie et al. |
| 2006/0004010 A1 | 1/2006 | Habashita et al. |
| 2006/0084650 A1 | 4/2006 | Dong et al. |
| 2006/0089362 A1 | 4/2006 | Seno et al. |
| 2006/0178367 A1 | 8/2006 | Currie et al. |
| 2006/0183746 A1 | 8/2006 | Currie et al. |
| 2006/0229337 A1 | 10/2006 | Brittelli et al. |
| 2006/0270686 A1 | 11/2006 | Kelly et al. |
| 2007/0099938 A1 | 5/2007 | Ohmoto et al. |
| 2007/0191395 A1 | 8/2007 | Kawakami et al. |
| 2008/0045536 A1 | 2/2008 | Vaccaro et al. |
| 2008/0139557 A1 | 6/2008 | Blomgren et al. |
| 2008/0153834 A1 | 6/2008 | Blomgren et al. |
| 2008/0280891 A1 | 11/2008 | Kelly et al. |
| 2009/0163545 A1 | 6/2009 | Goldfarb |
| 2009/0253735 A1 | 10/2009 | Almario-Garcia et al. |
| 2009/0281075 A1 | 11/2009 | Roughton et al. |
| 2009/0281120 A1 | 11/2009 | Nakai et al. |
| 2009/0304821 A1 | 12/2009 | Notoya et al. |
| 2010/0155712 A1 | 6/2010 | Kitamura |
| 2010/0160292 A1 | 6/2010 | Whitney et al. |
| 2010/0160303 A1 | 6/2010 | Liu et al. |
| 2010/0249151 A1 | 9/2010 | Klein et al. |
| 2010/0267775 A1 | 10/2010 | Negoro et al. |
| 2010/0267778 A1 | 10/2010 | Kusuda et al. |
| 2010/0273832 A1 | 10/2010 | Jung et al. |
| 2010/0292227 A1 | 11/2010 | Yoakim et al. |
| 2011/0053915 A1 | 3/2011 | Ivaschenko et al. |
| 2011/0062858 A1 | 3/2011 | Yersin et al. |
| 2011/0065699 A1 | 3/2011 | De Peretti et al. |
| 2011/0065700 A1 | 3/2011 | De Peretti et al. |
| 2011/0065745 A1 | 3/2011 | De Peretti et al. |
| 2011/0124640 A1 | 5/2011 | Liu et al. |
| 2011/0294781 A1 | 12/2011 | Yamamoto et al. |
| 2011/0301145 A1 | 12/2011 | Barbosa, Jr. et al. |
| 2012/0058996 A1 | 3/2012 | Liu et al. |
| 2012/0295884 A1 | 11/2012 | Altmann et al. |
| 2012/0323002 A1 | 12/2012 | Yamamoto et al. |
| 2012/0328569 A1 | 12/2012 | McComas et al. |
| 2013/0096118 A1 | 4/2013 | Liu et al. |
| 2013/0131063 A1 | 5/2013 | Castro et al. |
| 2013/0203741 A1 | 8/2013 | Suzuki et al. |
| 2013/0203747 A1 | 8/2013 | Yoakim et al. |
| 2013/0203754 A1 | 8/2013 | Yang et al. |
| 2013/0253011 A1 | 9/2013 | Jung et al. |
| 2014/0058097 A1 | 2/2014 | Kobayashi et al. |
| 2014/0088117 A1 | 3/2014 | Burch et al. |
| 2014/0128382 A1 | 5/2014 | Wu et al. |
| 2014/0243306 A1 | 8/2014 | Heng et al. |
| 2014/0275058 A1 | 9/2014 | Minatti et al. |
| 2014/0288094 A1 | 9/2014 | Bennett et al. |
| 2014/0378447 A1 | 12/2014 | Okano et al. |
| 2015/0005279 A1 | 1/2015 | Bonafoux et al. |
| 2015/0011751 A1 | 1/2015 | Kawakami et al. |
| 2015/0073024 A1 | 3/2015 | Sasikumar et al. |
| 2015/0181880 A1 | 7/2015 | Takahashi |
| 2015/0210680 A1 | 7/2015 | Kobayashi et al. |
| 2015/0232478 A1 | 8/2015 | Ishida et al. |
| 2015/0239868 A1 | 8/2015 | Pais et al. |
| 2015/0252011 A1 | 9/2015 | Minatti et al. |
| 2015/0258505 A1 | 9/2015 | Hironaka et al. |
| 2015/0291549 A1 | 10/2015 | Chupak et al. |
| 2015/0299227 A1 | 10/2015 | Wolkenberg et al. |
| 2015/0307465 A1 | 10/2015 | Scott et al. |
| 2015/0376172 A1 | 12/2015 | Guba et al. |
| 2016/0015690 A1 | 1/2016 | Babaoglu et al. |
| 2016/0046648 A1 | 2/2016 | Petrukhin et al. |
| 2016/0130251 A1 | 5/2016 | Graupe et al. |
| 2016/0194295 A1 | 7/2016 | Sasikumar et al. |
| 2016/0229816 A1 | 8/2016 | Sato et al. |
| 2016/0280695 A1 | 9/2016 | Minatti et al. |
| 2017/0107216 A1 | 4/2017 | Wu et al. |
| 2017/0145025 A1 | 5/2017 | Li et al. |
| 2017/0174671 A1 | 6/2017 | Wu et al. |
| 2017/0174679 A1 | 6/2017 | Lajkiewicz et al. |
| 2017/0304282 A1 | 10/2017 | Rocco et al. |
| 2017/0320875 A1 | 11/2017 | Li et al. |
| 2017/0342060 A1 | 11/2017 | Lu et al. |
| 2017/0362253 A1 | 12/2017 | Xiao et al. |
| 2018/0016260 A1 | 1/2018 | Yu et al. |
| 2018/0057486 A1 | 3/2018 | Wu et al. |
| 2018/0177784 A1 | 6/2018 | Wu et al. |
| 2018/0177870 A1 | 6/2018 | Liu et al. |
| 2018/0179179 A1 | 6/2018 | Wu et al. |
| 2018/0179197 A1 | 6/2018 | Wu et al. |
| 2018/0179201 A1 | 6/2018 | Wu et al. |
| 2018/0179202 A1 | 6/2018 | Wu et al. |
| 2018/0273519 A1 | 9/2018 | Wu et al. |
| 2019/0040082 A1 | 2/2019 | Xiao et al. |
| 2019/0062345 A1 | 2/2019 | Xiao et al. |
| 2019/0071439 A1 | 3/2019 | Li et al. |
| 2019/0144439 A1 | 5/2019 | Wu et al. |
| 2019/0202824 A1 | 7/2019 | Wu et al. |
| 2019/0225601 A1 | 7/2019 | Wu et al. |
| 2019/0270706 A1 | 9/2019 | Jorgensen et al. |
| 2019/0300524 A1 | 10/2019 | Wu et al. |
| 2019/0345170 A1 | 11/2019 | Wu et al. |
| 2020/0172533 A1 | 6/2020 | Wu et al. |
| 2020/0172541 A1 | 6/2020 | Li et al. |
| 2020/0181126 A1 | 6/2020 | Lu et al. |
| 2020/0255424 A1 | 8/2020 | Wu et al. |
| 2020/0277309 A1 | 9/2020 | Wu et al. |
| 2020/0283423 A1 | 9/2020 | Yu et al. |
| 2020/0325115 A1 | 10/2020 | Wu et al. |
| 2020/0397893 A1 | 12/2020 | Liu et al. |
| 2020/0407357 A1 | 12/2020 | Lajkiewicz et al. |
| 2021/0002276 A1 | 1/2021 | Wu et al. |
| 2021/0017164 A1 | 1/2021 | Lu et al. |
| 2021/0017175 A1 | 1/2021 | Li et al. |
| 2021/0040090 A1 | 2/2021 | Jia et al. |
| 2021/0094976 A1 | 4/2021 | Li et al. |
| 2021/0107900 A1 | 4/2021 | Wu et al. |
| 2021/0115025 A1 | 4/2021 | Yu et al. |
| 2021/0115068 A1 | 4/2021 | Wu et al. |
| 2021/0139511 A1 | 5/2021 | Jia et al. |
| 2021/0221819 A1 | 7/2021 | Li et al. |
| 2021/0317139 A1 | 10/2021 | Xiao et al. |
| 2021/0347771 A1 | 11/2021 | Wu et al. |
| 2021/0363137 A1 | 11/2021 | Wu et al. |
| 2021/0380584 A1 | 12/2021 | Wu et al. |
| 2022/0089588 A1 | 3/2022 | Wu et al. |
| 2022/0144830 A1 | 5/2022 | Zhou et al. |
| 2022/0144831 A1 | 5/2022 | Wang et al. |
| 2022/0144832 A1 | 5/2022 | Jia et al. |
| 2022/0193050 A1 | 6/2022 | Yang et al. |
| 2022/0194931 A1 | 6/2022 | Wu et al. |
| 2022/0213090 A1 | 7/2022 | Wu et al. |

FOREIGN PATENT DOCUMENTS

| | | |
|---|---|---|
| CL | 2018001531 | 7/2018 |
| CL | 2018003734 | 2/2019 |
| CL | 2018003701 | 4/2019 |
| CL | 2018003697 | 5/2019 |
| CL | 2019001744 | 10/2019 |
| CL | 2020002511 | 9/2020 |
| CN | 1344256 | 4/2002 |
| CN | 101891895 | 11/2010 |
| CN | 101910158 | 12/2010 |
| CN | 103933036 | 7/2014 |
| CN | 104045552 | 9/2014 |
| CN | 104211726 | 12/2014 |

(56) References Cited

FOREIGN PATENT DOCUMENTS

| | | |
|---|---|---|
| CN | 105164121 | 12/2015 |
| CN | 105705489 | 6/2016 |
| EP | 0361069 | 4/1990 |
| EP | 0644460 | 3/1995 |
| EP | 1505068 | 2/2005 |
| EP | 1644370 | 4/2006 |
| EP | 1942105 | 7/2008 |
| EP | 2233474 | 9/2010 |
| EP | 2402345 | 1/2012 |
| EP | 2871179 | 5/2015 |
| EP | 2824099 | 1/2018 |
| FR | 1425700 | 1/1966 |
| JP | H 10316853 | 12/1998 |
| JP | 2000128986 | 5/2000 |
| JP | 2000128987 | 5/2000 |
| JP | 2000212281 | 8/2000 |
| JP | 2001114893 | 4/2001 |
| JP | 2001163975 | 6/2001 |
| JP | 3461397 | 10/2003 |
| JP | 2003287634 | 10/2003 |
| JP | 2004059761 | 2/2004 |
| JP | 2004091369 | 3/2004 |
| JP | 2004294556 | 10/2004 |
| JP | 2005002330 | 1/2005 |
| JP | 2005248082 | 9/2005 |
| JP | 2005290301 | 10/2005 |
| JP | 2006-290883 | 10/2006 |
| JP | 2008218327 | 9/2008 |
| JP | 2010202530 | 9/2010 |
| JP | 2010540452 | 12/2010 |
| JP | 2013084945 | 5/2013 |
| JP | 2014520866 | 8/2014 |
| JP | 2014532066 | 12/2014 |
| JP | 2015155397 | 8/2015 |
| JP | 2015193612 | 11/2015 |
| JP | 2016135778 | 7/2016 |
| JP | 2016532710 | 10/2016 |
| JP | 2019523231 | 8/2019 |
| JP | 2019530732 | 10/2019 |
| JP | 2020504737 | 2/2020 |
| JP | 2020504739 | 2/2020 |
| JP | 2020514271 | 5/2020 |
| JP | 6911031 | 7/2021 |
| KR | 1715090 | 3/2015 |
| KR | 1717601 | 12/2015 |
| KR | 1653560 | 2/2016 |
| TW | 103143948 | 12/2014 |
| TW | 201625527 | 7/2016 |
| WO | WO 98/27108 | 6/1998 |
| WO | WO 1999/018096 | 4/1999 |
| WO | WO 99/44992 A1 | 9/1999 |
| WO | WO 00/35886 | 6/2000 |
| WO | WO 01/07409 | 2/2001 |
| WO | WO 2001/047883 | 7/2001 |
| WO | WO 01/74815 | 10/2001 |
| WO | WO 2002/000196 | 1/2002 |
| WO | WO 02/14321 | 2/2002 |
| WO | WO 02/48147 | 6/2002 |
| WO | WO 02/066477 | 8/2002 |
| WO | WO 02/071827 | 9/2002 |
| WO | WO 02/078700 | 10/2002 |
| WO | WO 02/083672 | 10/2002 |
| WO | WO 02/088124 | 11/2002 |
| WO | WO 03/022845 | 3/2003 |
| WO | WO 03/030901 | 4/2003 |
| WO | WO 03/031587 | 4/2003 |
| WO | WO 2004/006906 | 1/2004 |
| WO | WO 2004/033454 | 4/2004 |
| WO | WO 2004/035588 | 4/2004 |
| WO | WO 2004/085385 | 10/2004 |
| WO | WO 2004/089940 | 10/2004 |
| WO | WO 2005/000833 | 1/2005 |
| WO | WO 2005/005429 | 1/2005 |
| WO | WO 2005/014543 | 2/2005 |
| WO | WO 2005/014599 | 2/2005 |
| WO | WO 2005/023761 | 3/2005 |
| WO | WO 2005/034869 | 4/2005 |
| WO | WO 2005/047290 | 5/2005 |
| WO | WO 2005/063710 | 7/2005 |
| WO | WO 2005/077948 | 8/2005 |
| WO | WO 2005/079802 | 9/2005 |
| WO | WO 2005/080316 | 9/2005 |
| WO | WO 2005/086808 | 9/2005 |
| WO | WO 2005/086904 | 9/2005 |
| WO | WO 2005/097751 | 10/2005 |
| WO | WO 2005/103022 | 11/2005 |
| WO | WO 2005/105798 | 11/2005 |
| WO | WO 2006/034317 | 3/2006 |
| WO | WO 2006/034337 | 3/2006 |
| WO | WO 2006/050803 | 5/2006 |
| WO | WO 2006/053121 | 5/2006 |
| WO | WO 2006/094235 | 9/2006 |
| WO | WO 2006/099075 | 9/2006 |
| WO | WO 2006/125101 | 11/2006 |
| WO | WO 2007/004954 | 1/2007 |
| WO | WO 2007/034282 | 3/2007 |
| WO | WO 2007/038314 | 4/2007 |
| WO | WO 2007/061764 | 5/2007 |
| WO | WO 2007/067711 | 6/2007 |
| WO | WO 2007/069565 | 6/2007 |
| WO | WO 2007/096764 | 8/2007 |
| WO | WO 2007/113226 | 10/2007 |
| WO | WO 2007/146712 | 12/2007 |
| WO | WO 2008/011560 | 1/2008 |
| WO | WO 2008/021745 | 2/2008 |
| WO | WO 2008/027812 | 3/2008 |
| WO | WO 2008/032171 | 3/2008 |
| WO | WO 2008/033854 | 3/2008 |
| WO | WO 2008/033857 | 3/2008 |
| WO | WO 2008/033858 | 3/2008 |
| WO | WO 2008/057254 | 5/2008 |
| WO | WO 2008/062182 | 5/2008 |
| WO | WO 2008/064317 | 5/2008 |
| WO | WO 2008/064318 | 5/2008 |
| WO | WO 2008/071944 | 6/2008 |
| WO | WO 2008/079965 | 7/2008 |
| WO | WO 2008/104077 | 9/2008 |
| WO | WO 2008/104278 | 9/2008 |
| WO | WO 2008/104279 | 9/2008 |
| WO | WO 2008/111299 | 9/2008 |
| WO | WO 2008/114002 | 9/2008 |
| WO | WO 2008/118122 | 10/2008 |
| WO | WO 2008/133274 | 11/2008 |
| WO | WO 2008/134553 | 11/2008 |
| WO | WO 2008/141249 | 11/2008 |
| WO | WO 2009/027733 | 3/2009 |
| WO | WO 2009/038759 | 3/2009 |
| WO | WO 2009/039397 | 3/2009 |
| WO | WO 2009/059162 | 5/2009 |
| WO | WO 2009/062059 | 5/2009 |
| WO | WO 2009/075830 | 6/2009 |
| WO | WO 2009/077197 | 6/2009 |
| WO | WO 2009/079683 | 7/2009 |
| WO | WO 2009/106539 | 9/2009 |
| WO | WO 2009/106597 | 9/2009 |
| WO | WO 2009/123986 | 10/2009 |
| WO | WO 2009/139576 | 11/2009 |
| WO | WO 2009/143156 | 11/2009 |
| WO | WO 2009/146358 | 12/2009 |
| WO | WO 2010/011837 | 1/2010 |
| WO | WO 2010/029950 | 3/2010 |
| WO | WO 2010/056875 | 5/2010 |
| WO | WO 2010/064020 | 6/2010 |
| WO | WO 2010/071885 | 6/2010 |
| WO | WO 2010/075376 | 7/2010 |
| WO | WO 2010/080474 | 7/2010 |
| WO | WO 2010/104306 | 9/2010 |
| WO | WO 2010/115736 | 10/2010 |
| WO | WO 2010/119264 | 10/2010 |
| WO | WO 2010/130034 | 11/2010 |
| WO | WO 2011/002635 | 1/2011 |
| WO | WO 2011/008709 | 1/2011 |
| WO | WO 2011/018170 | 2/2011 |
| WO | WO 2011/044181 | 4/2011 |

(56) References Cited

FOREIGN PATENT DOCUMENTS

| | | |
|---|---|---|
| WO | WO 2011/047129 | 4/2011 |
| WO | WO 2011/047319 | 4/2011 |
| WO | WO 2011/050245 | 4/2011 |
| WO | WO 2009/096202 | 5/2011 |
| WO | WO 2011/082400 | 7/2011 |
| WO | WO 2011/097607 | 8/2011 |
| WO | WO 2011/113606 | 9/2011 |
| WO | WO 2011/117264 | 9/2011 |
| WO | WO 2011/140202 | 11/2011 |
| WO | WO 2012/016133 | 2/2012 |
| WO | WO 2012/033735 | 3/2012 |
| WO | WO 2012/034363 | 3/2012 |
| WO | WO 2012/047856 | 4/2012 |
| WO | WO 2012/052730 | 4/2012 |
| WO | WO 2012/052745 | 4/2012 |
| WO | WO 2012/068406 | 5/2012 |
| WO | WO 2012/080376 | 6/2012 |
| WO | WO 2012/088411 | 6/2012 |
| WO | WO 2012/100342 | 8/2012 |
| WO | WO 2012/125886 | 9/2012 |
| WO | WO 2012/129562 | 9/2012 |
| WO | WO 2012/139425 | 10/2012 |
| WO | WO 2012/159565 | 11/2012 |
| WO | WO 2012/166951 | 12/2012 |
| WO | WO 2012/168733 | 12/2012 |
| WO | WO 2012/175991 | 12/2012 |
| WO | WO 2013/008095 | 1/2013 |
| WO | WO 2013/033901 | 3/2013 |
| WO | WO 2013/040528 | 3/2013 |
| WO | WO 2013/057650 | 4/2013 |
| WO | WO 2013/059594 | 4/2013 |
| WO | WO 2013/120040 | 8/2013 |
| WO | WO 2013/134113 | 9/2013 |
| WO | WO 2013/157021 | 10/2013 |
| WO | WO 2013/163404 | 10/2013 |
| WO | WO 2014/009295 | 1/2014 |
| WO | WO 2014/009296 | 1/2014 |
| WO | WO 2014/017087 | 1/2014 |
| WO | WO 2014/039595 | 3/2014 |
| WO | WO 2014/061693 | 4/2014 |
| WO | WO 2014/081878 | 5/2014 |
| WO | WO 2014/113388 | 7/2014 |
| WO | WO 2014/114532 | 7/2014 |
| WO | WO 2014/121085 | 8/2014 |
| WO | WO 2014/133046 | 9/2014 |
| WO | WO 2014/138484 | 9/2014 |
| WO | WO 2014/138791 | 9/2014 |
| WO | WO 2014/151634 | 9/2014 |
| WO | WO 2014/152536 | 9/2014 |
| WO | WO 2014/159959 | 10/2014 |
| WO | WO 2014/181287 | 11/2014 |
| WO | WO 2014/186035 | 11/2014 |
| WO | WO 2014/210255 | 12/2014 |
| WO | WO 2015/000715 | 1/2015 |
| WO | WO 2015/013635 | 1/2015 |
| WO | WO 2015/018940 | 2/2015 |
| WO | WO 2015/033299 | 3/2015 |
| WO | WO 2015/033301 | 3/2015 |
| WO | WO 2015/034820 | 3/2015 |
| WO | WO 2015/036927 | 3/2015 |
| WO | WO 2015/086498 | 6/2015 |
| WO | WO 2015/086499 | 6/2015 |
| WO | WO 2015/086502 | 6/2015 |
| WO | WO 2015/086512 | 6/2015 |
| WO | WO 2015/095337 | 6/2015 |
| WO | WO 2015/101622 | 7/2015 |
| WO | WO 2015/120364 | 8/2015 |
| WO | WO 2015/150097 | 10/2015 |
| WO | WO 2015/160641 | 10/2015 |
| WO | WO 2015/197028 | 12/2015 |
| WO | WO 2016/044604 | 3/2016 |
| WO | WO 2016/094688 | 6/2016 |
| WO | WO 2016/116525 | 7/2016 |
| WO | WO 2016/118404 | 7/2016 |
| WO | WO 2016/156282 | 10/2016 |
| WO | WO 2017/035405 | 3/2017 |
| WO | WO 2017/066227 | 4/2017 |
| WO | WO 2017/070089 | 4/2017 |
| WO | WO 2017/070320 | 4/2017 |
| WO | WO 2017/087777 | 5/2017 |
| WO | WO 2017/106634 | 6/2017 |
| WO | WO 2017/108569 | 6/2017 |
| WO | WO 2017/109041 | 6/2017 |
| WO | WO 2017/112617 | 6/2017 |
| WO | WO 2017/112730 | 6/2017 |
| WO | WO 2017/192961 | 11/2017 |
| WO | WO 2017/205464 | 11/2017 |
| WO | WO 2017/222976 | 12/2017 |
| WO | WO 2017/223239 | 12/2017 |
| WO | WO 2018/013789 | 1/2018 |
| WO | WO 2018/026971 | 2/2018 |
| WO | WO 2018/044783 | 3/2018 |
| WO | WO 2018/045084 | 3/2018 |
| WO | WO 2016/057500 | 4/2018 |
| WO | WO 2018/116259 | 6/2018 |
| WO | WO 2018/119036 | 6/2018 |
| WO | WO 2018/119221 | 6/2018 |
| WO | WO 2018/119224 | 6/2018 |
| WO | WO 2018/119236 | 6/2018 |
| WO | WO 2018/119263 | 6/2018 |
| WO | WO 2018/119266 | 6/2018 |
| WO | WO 2018/119286 | 6/2018 |
| WO | WO 2018/195321 | 10/2018 |
| WO | WO 2019/023575 | 1/2019 |
| WO | WO 2019/032547 | 2/2019 |
| WO | WO 2019/034172 | 2/2019 |
| WO | WO 2019/191707 | 10/2019 |
| WO | WO 2019/192506 | 10/2019 |
| WO | WO 2019/204609 | 10/2019 |
| WO | WO 2020/086556 | 4/2020 |
| WO | WO 2020/088357 | 5/2020 |
| WO | WO 2020/156323 | 8/2020 |
| WO | WO 2021/030162 | 2/2021 |

OTHER PUBLICATIONS

Chilean Office Action in Chilean Application No. 2922-2020, dated Dec. 8, 2021, 21 pages.
Chinese Office Action in Chinese Application No. 201680077700.8, dated Jul. 2, 2021, 23 pages.
Gu et al., "Undo the brake of tumour immune tolerance with antibodies, peptide mimetics and small molecule compounds targeting PD-1/PD-L1 checkpoint at different locations for acceleration of cytotoxic immunity to cancer cells," Clinical and Experimental Pharmacology and Physiology, 2019, 46(2):105-115.
Huang et al., "Pharmacological treatment for keloids," Expert opinion on pharmacotherapy, 2013, 14(15):2087-2100.
Japanese Office Action in Japanese Application No. 2019-534122, dated Oct. 19, 2021, 10 pages.
Japanese Office Action in Japanese Application No. 2019-534195, dated Nov. 1, 2021, 8 pages.
Japanese Office Action in Japanese Application No. 2019-534196, dated Nov. 9, 2021, 8 pages.
Lexico.com, "Synonyms of Enhance," Oxford Dictionary, retrieved on Dec. 9, 2021, retrieved from URL <https://www.lexico.conn/synonynns/enhance>, 4 pages.
Qin et al., "The Diverse Function of PD-1/PD-L Pathway Beyond Cancer," Frontiers In Imunology, Oct. 2019, 10(2298):1-16.
Suarez et al., "Inhibitors of TAM subfamily of tyrosine kinases: synthesis and biological evaluation," European Journal of Medicinal Chemistiy, 2013, 61:6-25.
Yao et al., "PD-1 as an Immune Modulatory Receptor," Cancer J., 2014, 20(4):262-264.
Abdellaoui et al., "Palladium-catalyzed non-directed C—H bond arylation of difluorobenzenes and dichlorobenzenes bearing benzoxazole or benzothiazole," Catalysis Communications, 2015, 71:13-16.
Ahmed et al., "Enantioselective Polymerization of Epoxides Using Biaryl-Linked Bimetallic Cobalt Catalysts: A Mechanistic Study," J Am Chem Soc., 2013, 135(50):18901-18911.

(56) References Cited

OTHER PUBLICATIONS

Alverez et al., "Structure-Activity Study of Bioisosteric Trifluoromethyl and Pentafluorosulfanyl Indole Inhibitors of the AAA ATPase p97," ACS Med Chem., 2015, 6(12):1225-1230.

Amaya et al., "Synthesis of three-dimensionally arranged bisbiphenol ligand on hexaaryl benzene scaffold and its application for cross-pinacol coupling reaction," Tetrahedron Letters, 2011, 52(35):4567-4569.

Anyika et al., "Point-to-Axial Chirality Transfer—A New Probe for "Sensing" the Absolute Configurations of Monoamines," J Am Chem Soc., 2014, 136(2):550-553.

Arkin et al., "Small-Molecule Inhibitors of Protein-Protein Interactions: Progressing toward the Reality," Chemistiy & Biology, Sep. 2014, 21:1102-1114.

Arkin et al., "Small-Molecule Inhibitors of Protein-Protein Interactions: Progressing Towards the Dream," Nature Reviews, Apr. 2004, 3:301-317.

Artz et al., "Host-guest complexation. 28. Hemispherands with four self-organizing units," J Am Chem Soc., 1984, 106(7):2160-2171.

Atzrodt et al., "The Renaissance of H/D Exchange," Angew Chem Int Ed., 2007, 7744-7765.

Australian Office Action in Australian Application No. 2016358100, dated May 8, 2020, 5 pages.

Barakat, "Do We Need Small Molecule Inhibitors for the Immune Checkpoints?" J. Pharma. Care Health Sys., 2014, 1(4):1000e119.

Barber et al, "Restoring function in exhausted CD8 T cells during chronic viral infection," Nature, Feb. 2006, 439:682-687.

Bentley et al., "Antenna Biphenols: Development of Extended Wavelength Chiroptical Reporters," J Org Chem., 2016, 81(3):1185-1191.

Berg, "Modulation of Protein-Protein Interactions with Small Organic Molecules," Angew. Chem. Int. Ed., 2003, 42:2462-2481.

Berge et al., "Pharmaceutical Salts," J. Pharm. Sci., Jan. 1977, 66(1):1-19.

Blank et al, "PD-L1/B7H-1 Inhibits the Effector Phase of Tumor Rejection by T Cell Receptor (TCR) Transgenic CD8+ T Cells," Cancer Res., Feb. 2004, 64(3):1140-5.

Blom et al., "Optimizing Preparative LC-MS Configurations and Methods for Parallel Synthesis Purification", J. Combi. Chem., 2003, 5:670-83.

Blom et al., "Preparative LC-MS Purification: Improved Compound Specific Method Optimization", J. Combi. Chem., Nov. 2004, 6:874-883.

Blom, "Two-Pump At Column Dilution Configuration for Preparative LC-MS", K. Blom, J. Combi. Chem., 2002, 4:295-301.

Brazilian Office Action in Brazilian Application No. BRI 12018012756-6, dated Jan. 5, 2021, 6 pages.

Brass et al., "Radiation damage to 2-(2'-hydroxyphenyl)benzothiazoles," Radiation Physics and Chemistry, Jul. 1992, 41:379-387.

Buisman et al., "Chiral Cooperativity in Diastereomeric Diphosphite Ligands: Effects on the Rhodium-Catalyzed Enantioselective Hydroformylation of Styrene," Organometallics, 1997, 16(13):2929-2939.

Carter et al., "PD-1:PD-L inhibitory pathway affects both CD4+ and CD8+ T cells and is overcome by IL-2," Eur. J. Immunol., 2002, 32(3):634-643.

Chang et al., "Blocking of the PD-1/PD-L1 Interaction by a d-Peptide Antagonist for Cancer Immunotherapy," Angew. Chem. Int. Ed., 2015, 127(40):11926-11930.

Chang et al., "Blocking of the PD-1/PD-L1 Interaction by a d-Peptide Antagonist for Cancer Immunotherapy" Angew. Chem. Int. Ed., 2015, 26 pages; Supporting Information for 127(40):11926-11930.

Chen et al., "Anti-PD-1/PD-L1 therapy of human cancer: past, present, and future," J. Clin. Invest., Sep. 2015, 125(9):3384-3391.

Cheng et al., "Synthetic connections to the aromatic directed metalation reaction. Iterative ortho metalation-cross coupling tactics for the construction of polyphenyls," Tetrahedron Letters, 1978, 28(43):5097-5098.

Cheng et al., "Recent Advances in Small Molecule Based Cancer Immunotherapy," Eur J Med Chem., 2018, 157:582-598.

Cheng et al., "Structure and Interactions of the Human Programmed Cell Death 1 Receptor," J. Bio. Chem., Apr. 2013, 288(17):11771-11785.

Chilean Office Action in Chilean Application No. 201801685, dated Aug. 20, 2019, 18 pages.

Chilean Office Action in Chilean Application No. 201803701, dated Nov. 22, 2019, 18 page.

Chilean Office Action in Chilean Application No. 201901744, dated Apr. 14, 2020, 19 pages.

Chinese Search Report in Chinese Application No. 201780049752.9, dated Dec. 28, 2020, 5 pages.

Clayden et al., "Conformational Preference and Remote (1,10) Stereocontrol in Biphenyl-2,2'-dicarboxamides," Org. Lett., 2001, 3(26):4133-4136.

Colombian Office Action in Colombian Application No. NC2019/0000386, dated Sep. 25, 2020, 18 pages.

Cram et al., "Host-guest complexation. 32. Spherands composed of cyclic urea and anisyl units," J Am Chem Soc., 1984, 106(23):7150-7167.

Cram et al., "Host-guest complexation. 29. Expanded hemispherands," J Am Chem Soc., 1984, 106(11):6386-3292.

Cram et al., "Host-guest complexation. 26. Cavitands composed of fluorobenzene units bonded in their 2,6-positions to form macrocycles," J Am Chem Soc., 1984, 106(3):695-701.

Cram et al., "Spherand hosts containing cyclic urea units," J Am Chem Soc., 1982, 104(24):6828-6830.

Curis, "Overview and Path for Growth," Aurigene Strategic Collaboration, Jan. 21, 2015, 13 slides.

Database Accession No. 1590700-72-3 abstract, Apr. 27, 2014, 1 page.

Database Accession No. 1581556-71-9 abstract, Apr. 8, 2014, 1 page.

Database Accession No. 1580823-55-7 abstract, Apr. 6, 2014, 1 page.

Database Accession No. 1568738-04-4 abstract, Mar. 14, 2014, 1 page.

Database accession No. 1478989-52-4 abstract, Nov. 22, 2013, 1 page.

Database accession No. 2013:447446 abstract, 2013, 1 page.

De Lucca et al., "Small Molecule Reversible Inhibitors of Bruton's Tyrosine Kinase (BTK): Structure-Activity Relationships Leading to the Identification of 7-(2-Hydroxypropan-2-yl)-4-[2-methyl-3-(4-oxo-3,4-dihydroquinazolin-3-yl)phenyl]-9H-carbazole-1-carboxamide (BMS-935177)," Journal of Medicinal Chemistiy, 2016, 59(17):7915-7935.

Differding, "AUNP-12—A Novel Peptide Therapeutic Targeting PD-1 Immune Checkpoint Pathway for Cancer Immunotherapy—Structure Activity Relationships & Peptide / Peptidomimetic Analogs," Differding Consulting s.p.r.l. (Belgium), Feb. 26, 2014, 12 pages.

Dhanunjayarao et al., "Synthesis and Optical Properties of Salicylaldimine-Based Diboron Complexes," Eur J Inorg Chem., 2014, 3:539-545.

Dolan et al., "PD-1 Pathway Inhibitors: Changing the Landscape of Cancer Immunotherapy," Cancer Control, Jul. 2014, 21(3):231-237.

Domling et al., "Programmed Death-1: Therapeutic Success after More than 100 Years of Cancer Immunotherapy," Angew. Chem. Int. Ed., 2014, 53:2283-2288.

Ecuador Opposition in Ecuador Application No. SENADI-2019-3773, dated Oct. 10, 2019, 29 pages.

Escarcega-Bobadilla et al., "A Recyclable Trinuclear Bifunctional Catalyst Derived from a Tetraoxo Bis-Zn(salphen) Metalloligand," Chemistry—A European Journal., 2013, 19(8):2641-2648.

Escarcega-Bobadilla et al., "Metal-directed assembly of chiral bis-Zn(II) Schiff base structures," Dalton Transactions, 2012, 41(32):9766-9772.

Escarcega-Bobadilla et al., "Versatile Switching in Substrate Topicity: Supramolecular Chirality Induction in Di- and Trinuclear Host Complexes," Chemistry—A European Journal, 2012:8(22):6805-6810.

Eurasian Office Action in Eurasian Application No. 201990074/28, dated Oct. 3, 2019, 5 pages.

(56) References Cited

OTHER PUBLICATIONS

European Communication in European Application No. 16805690.1, dated Jul. 10, 2018, 6 pages.
European Communication in European Application No. 16805690.1, dated Jan. 22, 2020, 5 pages.
European Communication in European Application No. 17743174.9, dated Jan. 31, 2020, 5 pages.
European Communication in European Application No. 16805690.1, dated Nov. 5, 2020, 4 pages.
Fabris et al., "Central to Axial Transfer of Chirality in Menthone or Camphor-Derived 2,2'-Biphenols," J Org Chem., 1997, 62(21):7156-7164.
FDA Report, "22 Case Studies Where Phase 2 and Phase 3 Trials Had Divergent Results," U.S. Food and Drug Administration, Jan. 2017, 44 pages.
Francisco et al., "The PD-1 Pathway in Tolerance and Autoimmunity," Immunol. Rev., Jul. 2010, 236:219-242.
Freeman et al., "Engagement of the Pd-1 Immunoinhibitory Receptor by a Novel B7 Family Member Leads to Negative Regulation of Lymphocyte Activation," J. Exp. Med., Oct. 2000, 192(7):1027-34.
Freeman, "Structures of PD-1 with its ligands: Sideways and dancing cheek to cheek," PNAS, Jul. 2008, 105(30):10275-10276.
Freindorf, M., "Vibronic couplings in an excited state of hydrogen bond dimeric systems," Acta Physica Polonica, 1990, A78(6):825-839.
Gong et al., "Rhodium(I)-catalyzed regiospecific dimerization of aromatic acids: two direct C—H bond activations in water," Angewandte Chemie, 2015, 54(19):5718-5721.
Goswami et al., "A turn on ESIPT probe for rapid and ratiometric Iluorogenic detection of homocysteine and cysteine in water with live cell-imaging," Tetrahedron Letters, 2014, 55(2):490-494.
Gould et al. "Salt selection for basic drugs," Int J Pharma., 1986, 33(1-3):201-217.
Green et al., "Synthesis and investigation of the configurational stability of some dimethylammonium borate salts," J. Chem. Soc., Perkin Trans. 1, 2000, 24:4403-4408.
Greenwald et al., "The B7 Family Revisited," Annu. Rev. Immunol., 2005, 23:515-548.
Han et al., "Synthesis of binuclear phenoxyimino organoaluminum complexes and their use as the catalyst precursors for efficient ring-opening polymerisation of E-caprolactone," Dalton Transactions, 2013, 41:12346-12353.
Helgeson et al., "Host-guest complexation. 66. 18-Membered-ring spherands containing five anisyl groups," J Am Chem Soc., 1993, 1115(24):11506-11511.
Hilfiker "Relevance of Solid-state Properties for Pharmaceutical Products," Polymorphism in the Pharmaceutical Industry, Jan. 1, 2006, pp. 1-19.
Hu et al., "Syntheses and Ethylene Polymerization Behavior of Supported Salicylaldimine-Based Neutral Nickel(II) Catalysts," Organometallics, 2007, 26(10):2609-2615.
Hu et al., "Synthesis and Ethylene Polymerization Activity of a Novel, Highly Active Single-Component Binuclear Neutral Nickel(II) Catalyst," Organometallics, 2005, 24(11):2628-2632.
Hu et al., "Novel highly active binuclear neutral nickel and palladium complexes as precatalysts for norbomene polymerization," Journal of Molecular Catalysis A: Chemical 253, 2006, 155-164.
Huang et al, "The prognostic significance of PD-L1 in bladder cancer," Oncol. Rep., 2015, 33:3075-3084.
Huddle et al., "Reactions of alkyl-lithium compounds with aryl halides ," J Chem Soc., Perkin I, 1980, 12:2617-2625.
HuGEMM™ and HuCELL™ Models, "FactSheet," CrownBio, Oct. 2016, 8 pages.
Indian Office Action with Indian Application No. 201817026809, dated Apr. 29, 2020, 6 pages.
Indian Office Action with Indian Application No. 201917001998, dated Nov. 24, 2020, 7 pages.
Indian Office Action with Indian Application No. 201917028273, dated Feb. 15, 2021, 5 pages.

International Preliminary Report on Patentability in International Application No. PCT/US2016/057487, dated May 3, 2018, 7 pages.
International Preliminary Report on Patentability in International Application No. PCT/US2016/062730, dated May 31, 2018, 7 pages.
International Preliminary Report on Patentability in International Application No. PCT/US2016/067155, dated Jun. 19, 2018, 10 pages.
International Preliminary Report on Patentability in International Application No. PCT/US2016/067925, dated Jun. 26, 2018, 8 pages.
International Preliminary Report on Patentability in International Application No. PCT/US2017/031242, dated Nov. 6, 2018, 7 pages.
International Preliminary Report on Patentability in International Application No. PCT/US2017/034173, dated Nov. 27, 2018, 8 pages.
International Preliminary Report on Patentability in International Application No. PCT/US2017/038120, dated Dec. 25, 2018, 6 pages.
International Preliminary Report on Patentability in International Application No. PCT/US2017/041899, dated Jan. 15, 2019, 7 pages.
International Preliminary Report on Patentability in International Application No. PCT/US2017/048880, dated Mar. 5, 2019, 9 pages.
International Preliminary Report on Patentability in International Application No. PCT/US2017/067904, dated Jun. 25, 2019, 7 pages.
International Preliminary Report on Patentability in International Application No. PCT/US2017/067951, dated Jun. 25, 2019, 8 pages.
International Preliminary Report on Patentability in International Application No. PCT/US2017/067880, dated Jun. 25, 2019, 7 pages.
International Preliminary Report on Patentability in International Application No. PCT/US2017/067984, dated Jun. 25, 2019, 7 pages.
International Preliminary Report on Patentability in International Application No. PCT/US2017/067946, dated Jun. 25, 2019, 9 pages.
International Preliminary Report on Patentability in International Application No. PCT/US2017/067886, dated Jun. 25, 2019, 9 pages.
International Preliminary Report on Patentability in International Application No. PCT/US2019/025036, dated Oct. 15, 2020, 7 pages.
International Preliminary Report on Patentability in International Application No. PCT/US2019/031728, dated Nov. 17, 2020, 7 pages.
International Search Report and Written Opinion in International Application No. PCT/US2016/057487, dated Dec. 8, 2016, 11 pages.
International Search Report and Written Opinion in International Application No. PCT/US2016/062730, dated Feb. 9, 2017, 12 pages.
International Search Report and Written Opinion in International Application No. PCT/US2016/067925, dated Mar. 27, 2017, 13 pages.
International Search Report and Written Opinion in International Application No. PCT/US2016/067155, dated Apr. 24, 2017, 26 pages.
International Search Report and Written Opinion in International Application No. PCT/US2017/031242, dated Jun. 20, 2017, 22 pages.
International Search Report and Written Opinion in International Application No. PCT/US2017/034173, dated Aug. 8, 2017, 15 pages.
International Search Report and Written Opinion in International Application No. PCT/US2017/041899, dated Sep. 5, 2017, 12 pages.
International Search Report and Written Opinion in International Application No. PCT/US2017/038120, dated Aug. 1, 2017, 14 pages.

(56) References Cited

OTHER PUBLICATIONS

International Search Report and Written Opinion in International Application No. PCT/US2017/067904, dated Mar. 22, 2018, 14 pages.
International Search Report and Written Opinion in International Application No. PCT/US2017/067880, dated Mar. 21, 2018, 13 pages.
International Search Report and Written Opinion in International Application No. PCT/US2017/067984, dated Mar. 22, 2018, 14 pages.
International Search Report and Written Opinion in International Application No. PCT/US2017/067886, dated Mar. 23, 2018, 24 pages.
International Search Report and Written Opinion in International Application No. PCT/US2017/067946, dated May 22, 2018, 16 Pages.
International Search Report and Written Opinion in International Application No. PCT/US2017/067951, dated Mar. 27, 2018, 15 pages.
International Search Report and Written Opinion in International Application No. PCT/US2017/048880, dated Oct. 23, 2017, 15 pages.
International Search Report and Written Opinion in International Application No. PCT/US2019/031728, dated Jun. 25, 2019, 12 pages.
International Search Report and Written Opinion in International Application No. PCT/US2019/025036, dated Jul. 3, 2019, 12 pages.
International Search Report and Written Opinion in International Application No. PCT/US2020/045311, dated Oct. 2, 2020, 14 pages.
International Search Report in International Application No. PCT/US2020/053 190, dated Jan. 29, 2021, 13 pages.
International Search Report and Written Opinion in International Application No. PCT/US2020/059817, dated Mar. 29, 2021, 19 pages.
Israeli Office Action in Israeli Application No. 259,406, dated Mar. 11, 2020, 10 pages.
Israeli Office Action in Israeli Application No. 260,166, dated Jun. 2, 2020, 13 pages.
Iwai et al., "Involvement of PD-L1 on tumor cells in the escape from host immune system and tumor immunotherapy by PD-L1 blockade," PNAS, Sep. 2002, 99(19):12293-12297.
Japanese Office Action in Japanese Application No. 2018526213, dated Oct. 13, 2020, 10 pages.
Jiang et al., "Self-immobilizing binuclear neutral nickel catalyst for ethylene polymerization: Synthesis and catalytic studies," J Mol Cat., 2013, 380:139-143.
Kayal et al., "3,3'-Bis(triphenylsilyl)biphenoxide as a Sterically Hindered Ligand on Fe(II), Fe(III), and Cr(II)," Inorg Chem., 2002, 41(2):321-330.
Keir et al., "PD-1 and Its Ligands in Tolerance and Immunity," Annu. Rev. Immunol., 2008, 26:677-704.
Kerekes et al., "Aurora kinase inhibitors based on the imidazo[1,2-a]pyrazine core: fluorine and deuterium incorporation improve oral absorption and exposure," J Med Chem., 2011, 54(1):201-210.
Koch et al., "Nucleophilic reactions of pyridines and imidazoles with vinyl and aromatic halides," J Org Chem., 1993, 58(6):1409-1414.
Komiyama et al., "IL-17 Plays an Important Role in the Development of Experimental Autoimmune Encephalomyelitis," J. Immunol., Jul. 2006, 177:566-73.
Latchman et al., "PD-L2 is a second ligand for PD-1 and inhibits T cell activation," Nat. Immunol., Mar. 2001, 2(3):261-268.
Lazar-Molnar et al., "Crystal structure of the complex between programmed death-1 (PD-1) and its ligand PD-L2," PNAS, Jul. 2008, 105(30):10483-10488.
Legon'kova et al., "Interaction of o,o-dihalo o'-hydroxy azo compounds with metallic copper. II. Preparation of oligomeric azo compounds from monoazo compounds," Mosk Khim-Tekhnol Inst im Mendeleeva., 1968, 11(11):1281-1284 Machine Translation.

Legon'kova et al., "Interaction of o,o-dihalogeno o-hydroxy azo compounds with metallic copper," Trudy Instituta—Moskovskii Khimiko-Tekhnologicheskii Institut imeni D. I. Mendeleeva, 1965, 48:120-125 Machine Translation.
Lehtonen et al., "Comparison of quaternary methyl-, ethyl- and butylammonium hydroxides as alkylating reagents in pyrolysis-GC/MS studies of aquatic fulvic acid," Journal of Analytical and Applied Pyrolysis, 2003, 68-69:315-329.
Li et al., "A Mini-Review for Cancer Immunotherapy: Molecular Understanding of PD-1/PD-L1 Pathway & Translational Blockade of Immune Checkpoints," Int. J. Mol. Soc., 2016, 17:1151, 22 pages.
Li et al., "Analysis of Receptor Tyrosine Kinase Internalization Using Flow Cytometry," Methods Mol. Biol., 2008, 457:305-317.
Li et al., "Asymmetric Alternating Copolymerization of Meso-epoxides and Cyclic Anhydrides: Efficient Access to Enantiopure Polyesters," J. Am. Chem. Soc., 2016, 138(36):11493-11496.
Li et al., "A 3D Mesomeric Supramolecular Structure of a Cu(II) Coordination Polymer with 1,1'-Biphenyl-2,2',3,3'-tetracarboxylic Acid and 5,5'-Dimethyl-2,2'-bipyridine Ligands," J Inorg and Organomet Poly Mat., 2012, 22(6):1320-1324.
Li et al., "Discovery of peptide inhibitors targeting human programmed death 1 (PD-1) receptor," Oncotarget, Aug. 2016, 7(40):64967-64976.
Lin et al., "The PD-1/PD-L1 complex resembles the antigen-binding Fv domains of antibodies and T cell receptors," PNAS, Feb. 2008, 105(8):3011-3016.
Lipson et al., "From Discovery to Development: Blocking PD-1 and its Ligands," The Melanoma Letter, A Publication of The Skin Cancer Foundation, vol. 31, Summer 2013, 6 pages.
Liu et al., "Asymmetric Copolymerization of CO2 with meso-Epoxides Mediated by Dinuclear Cobalt(III) Complexes: Unprecedented Enantioselectivity and Activity," Angewandte Chemie, 2013, 52(44):11594-11598.
Liu et al., "Development of amino- and dimethylcarbamate-substituted resorcinol as programmed cell death-1 (PD-1) inhibitor," Eur J Pharm Sci, 2016, 88:50-58.
Mahoney et al., "The Next Immune-Checkpoint Inhibitors:PD-1/PD-L1 Blockade in Melanoma," Clin. Therapeutics, Nov. 2015, 37(4):761-782.
Maier et al., "Effects of the stationary phase and the solvent on the stereodynamics of biphep ligands quantified by dynamic three-column HPLC," Angewante Chemie, 2012, 51(12):2985-2988.
Manecke et al., "Preparation and properties of monomeric and polymeric Schiff bases derived from salicylaldehyde and 2,5-dihydroxyterephthalaldehyde. II. Electrical conductivity," Makromolekulare Chemie, 1972, 160:111-126 English Abstract.
Manecke et al., "Preparation and properties of chelate-forming monomeric and polymeric Schiff bases derived from salicylaldehyde and 2,5-dihydroxyterephthalaldehyde. I," Makromolekulare Chemie, 1970, 133:61-82 English Abstract.
Mexican Office Action in Mexican Application No. MX/a/2018/016273, dated Mar. 26, 2021, 7 pages.
Mexican Office Action in Mexican Application No. MX/a/2018/007774, dated Apr. 8, 2021, 5 pages.
Miyaura and Suzuki, "Palladium-Catalyzed Cross-Coupling Reactions of Organoboron Compounds," Chem Rev., 1995, 95:2457-2483.
Mochida et al., "Rhodium-Catalyzed Regioselective Olefination Directed by a Carboxylic Group," J Org Chem, 2011, 76(9):3024-3033.
Moneta et al., "Boron templated synthesis of macrocyclic hosts containing convergent hydroxy or methoxy groups," Bulletin de la Societe Chimique de France, 1988, 6:995-1004 (English Abstract).
Nallasivam et al., "Development of Unimolecular Tetrakis(piperidin-4-ol) as a Ligand for Suzuki-Miyaura Cross-Coupling Reactions: Synthesis of Incrustoporin and Preclamol," 2015, Eur J Org Chem., 2015(16):3558-3567.
Nero et al., "Oncogenic protein interfaces: small molecules, big challenges," Nature Reviews, Apr. 2014, 14:248-262.
Nishimura et al, "Autoimmune Dilated Cardiomyopathy in PD-1 Receptor-Deficient Mice," Science, Jan. 2001, 291:319-322.

(56) References Cited

OTHER PUBLICATIONS

Nishimura et al., "Development of Lupus-like Autoimmune Diseases by Disruption of the PD-1 Gene Encoding an ITIM Motif-Carrying Immunoreceptor," Immunity, Aug. 1999, 11:141-151.
Nishimura et al., "PD-1: an inhibitory immunoreceptor involved in peripheral tolerance," Trends in Immunology, May 2001, 22(5):265-268.
Nishino et al., "Copper-Mediated C—H/C—H Biaryl Coupling of Benzoic Acid Derivatives and 1,3-Azoles," Angew. Chem. Int. Ed., 2013, 52:4457-4461.
Normand et al., "Dinuclear vs. mononuclear complexes: accelerated, metal-dependent ring-opening polymerization of lactide," Chem. Commun., 2013, 49(99):11692-11694.
Okazaki and Honjo, "The PD-1-PD-L pathway in immunological tolerance," Trends Immunol., Apr. 2006, 4:195-201.
Okazaki et al., "A rheostat for immune responses: the unique properties of PD-1 and their advantages for clinical application," Nature Immunology, Dec. 2013, 14(12):1212-1218.
Paek et al.., "Facile syntheses and multi-orthofunctionalizations of tertiary benzamides," Bulletin of the Korean Chemical Society, 1993, 14(6):732-739.
Paek et al., "Chiral host. Attempted synthesis using McMurray reaction as a final ring closure method," Bulletin of the Korean Chemical Society, 1989, 10(6):572-577.
Pardoll, "The blockade of immune checkpoints in cancer immunotherapy," Nature, Apr. 2012, 12:252-264.
Parry et al., "CTLA-4 and PD-1 Receptors Inhibit T-Cell Activation by Distinct Mechanisms," Mol. Cell. Biol., Nov. 2005, 25(21):9543-9553.
Parsons et al., "Directed ortho metalation reactions. Expedient synthesis of 3,3'-disubstituted 1,1'-bi-(2-phenols) (BIPOLS)," Tetrahedron Letters, 1994, 35(41):7537-7540.
Pascolutti et al., "Structure and Dynamics of PD-L1 and an Ultra-High-Affinity PD-1 Receptor Mutant," Structure, Oct. 2016, 24:1719-1728.
Paulini et al., "Orthogonal Multipolar Interactions in Structural Chemistry and Biology," Angew. Chem. Int. Ed., 2005, 44:1788-1805.
Pearson et al., "The formation of complexes between aza-derivatives of crown ethers and primary alkylammonium salts. Part 5. Chiral macrocyclic diamines," J. Chem. Soc., Perkin I, 1979, 12:3113-3126.
Pfeiffer et al., "Inner complex salts of the aldimine and azo series," Journal fuer Praktische Chemie, 1937, 149:217-296 Machine Translation.
Pierre et al., "Synthesis of a new macrobicyclic siderophoric host molecule with six converging phenolate groups," Angewandte Chemie, 1991, 103(1):75-76 Machine Translation.
Postow et al, "Immune Checkpoint Blockade in Cancer Therapy," J. Clinical Oncology, Jun. 2015, 33(17):1974-1982.
Press Release Archive, "Boehringer Ingelheim and Yale University collaborate to investigate novel immunotherapy targets across several therapeutic areas," Boehringer Ingelheim, Jan. 13, 2015, 2 pages.
Puehlhofer et al., "SASAPOS cascades of perfluorinated aromatic carboxylic acids: low-temperature decarboxylation triggered by electrostatic effects of polycationic ligand sets," Euro J of Org Chem., 2004, 5:1002-1007.
Punniyamurthy et al., "Enantiomerically pure bicyclo[3.3.1]nona-2,6-diene as the sole source of enantioselectivity in BIPHEP-Rh asymmetric hydrogenation," Chem Comm., 2008, 41:5092-5094.
Sabatier et al, "Prognostic and predictive value of PDL1 expression in breast cancer," Oncotarget, Mar. 2015, 6(7):5449-5464.
Sharpe et al, "The function of programmed cell death 1 and its ligands in regulating autoimmunity and infection," Nat. Immunol., Mar. 2007 8(3):239-245.
Sharpe et al., "The B7-CD28 Superfamily," Nature Reviews, Feb. 2002, 2:116-126.
Sharma et al., "Palladium-Catalyzed Decarboxylative Acylation of O-Phenyl Carbamates with Alpha-Oxocarboxylic Acids at Room Temperature," Advanced Synthesis & Catalysis, 2013, 355(4):667-672.
STN Search Report dated Apr. 14, 2016, 79 pages.
STN Search Report dated Apr. 29, 2016, 69 pages.
STN Search Report dated Aug. 30, 2016, 4 pages.
STN Search Report dated Jun. 6, 2016, 115 pages.
STN Search Report dated Sep. 2, 2016, 115 pages.
STN Search Report, dated May 1, 2016, 12 pages.
STN Search Report dated May 24, 2016, 92 pages.
STN Search Report dated Sep. 12, 2016, 4 pages.
STN Search Report dated Jun. 16, 2016, 8 pages.
STN Search Report dated Sep. 12, 2016, 17 pages.
STN Search Report dated Jul. 12, 2016, 4 pages.
STN Search Report dated Aug. 19, 2016, 23 pages.
STN Search Report dated Dec. 15, 2016, 4 pages.
STN Search Report dated Dec. 19, 2016, 11 pages.
STN Search Report dated Dec. 16, 2016, 25 pages.
STN Search Report dated Dec. 16, 2016, 4 pages.
STN Search Report dated Dec. 20, 2016, 117 pages.
STN Search Report dated Sep. 27, 2017, 4 pages.
STN Search Report dated Mar. 27, 2018, 4 pages.
STN Search Report dated Apr. 30, 2018, 8 pages.
Sorrell et al., "3,3'-Disubstituted 2,2'-biphenols. Synthesis of nonplanar, tetradentate chelating ligands," J Org Chem., 1985, 50(26):5765-5769.
Storz, "Intellectual property issues of immune checkpoint inhibitors," mAbs, Jan. 2016, 8(1):10-26.
Sumrit et al., "Aluminum complexes containing salicylbenzoxazole ligands and their application in the ring-opening polymerization of rac-lactide and ε-caprolactone," Dalton Transactions (2016), 45(22), 9250-9266.
Sun et al., "Studies on Synthesis and Properties of Some New Dibenzocyclobromonium," Chemical Journal of Chinese Universities, 1998, 19(12), 6 pages (English Abstract).
Taiwan Office Action in Taiwan Application No. 105133530, dated Oct. 15, 2020, 8 pages.
Taiwan Office Action in Taiwan Application No. 105141804, dated Nov. 9, 2020, 9 pages.
Taiwan Office Action in Taiwan Application No. 105137807, dated Nov. 12, 2020, 12 pages.
Tang et al., "Facile synthesis of enantioenriched phenol-sulfoxides and their aluminum complexes," Org Biomol Chem., 2016, 14(24):5580-5585.
Thiel et al., "Small-Molecule Stabilization of Protein-Protein Interactions: An Underestimated Concept in Drug Discoveiy?" Angew. Chem. Int. Ed., 2012, 51:2012-2018.
Tucker et al., "Host-guest complexation. 52. Bridged and chiral hemispherands," J Org Chem., 1989, 54(23):5460-5482.
Ukraine Office Action in Ukraine Application No. a 2019 00525, dated Jan. 14, 2021, 11 pages.
Unrau et al., "Directed ortho metalation. Suzuki cross coupling connections. Convenient regiospecific routes to functionalized m- and p-teraryls and m-quinquearyls," Tetrahedron Letters, 1992, 33(20):2773-2776.
Velcheti et al., "Programmed death-1/programmed death-1 ligand axis as a therapeutic target in oncology: current insights," Journal of Receptor Ligand and Channel Research, Dec. 2014, 8(23):1-7.
Wang et al, "The prognostic value of PD-L1 expression for non-small cell lung cancer patients: A meta-analysis," Eur. J. Surg. Oncol., 2015, 41:450-456.
Wang et al, "A binuclear Zn(II)—Zn(II) complex from a 2-hydroxybenzohydrazide-derived Schiff base for selective detection of pyrophosphate," Dalton Transactions, Oct. 2014, 43(37):14142-14146.
Wang et al., "Molecular Modeling and Functional Mapping of B7—H1 and B7-DC Uncouple Costimulatory Function from PD-1 Interaction," J. Exp. Med., Apr. 2013, 197(3):1083-1091.
Wei et al., "Strength of PD-1 signaling differentially affects T-cell effector functions," PNAS, Apr. 2013, E2480-E2489.
Weinmann, "Cancer Immunotherapy: Selected Targets and Small-Molecule Modulators," Chem. Med. Chem., 2016, 11:450-466.

(56) References Cited

OTHER PUBLICATIONS

Weiss et al., "Electrostatics and color: Massive electrostatic perturbation of chromophores by ion cluster ligands," J Am Chem Soc., 2007, 129(3):547-553.
Weiss et al., "Electrostatic activation of SNAr-reactivity by sulfonylonio substituents," Zeitschrift fuer Naturforschung, 2001, 56(12):1360-1368 English Abstract.
Weiss et al., "First-ever per(onio) substitution of benzene: the role of the counterion," Angewandte Chemie, 1995, 34(12):1319-1321.
Weiss et al., "Massive electrostatic effects on heteropolar C—C disconnections: Transforming a phenyl anion into a potent leaving group," Euro J Org Chem., 2005, 16:3530-3535.
Weiss et al., "Poly-onio substituted quinones as strong electron acceptors," Inst Org Chem., 1986, 98(10):925-926.
Weiss et al., "SASAPOS, not Sisyphus: highly efficient 20-step one-pot synthesis of a discrete organic-inorganic ion cluster with a porphyrin core," Angewandte Chemie International Edition, 2002, 41(20):3815-3817.
Weiss et al., "Syntheses and Reactions of Polycationically Substituted Azido- and Diazidobenzenes," Eur J Org Chem., Nov. 2007, 31:5270-5276.
Wells et al., "Reaching for high-hanging fruit in drug discovery at protein-protein interfaces," Nature, Dec. 2007, 450:1001-1009.
Wu et al., "Targeting the BACE1 Active Site Flap Leads to a Potent Inhibitor That Elicits Robust Brain Aβ Reduction in Rodents," ACS Medicinal Chemistry Letters, 2016, 7(3):271-276.
Wuts et al., "Protective Groups in Organic Synthesis," 4th Ed., 2007, 1111 pages.
www.medscape.com [online]. "The 'Family Business' Behind the Finny of PD-1 Inhibitors," Sep. 10, 2014. [Retrieved on Jan. 29, 2015], Retrieved from the Internet: URL<http://www.medscape.com/viewarticle/831448_print>. 3 pages.
Xiong et al., "Biaryl-Bridged Salalen Ligands and Their Application in Titanium-Catalyzed Asymmetric Epoxidation of Olefins with Aqueous H2O2," Eur J Org Chem., 2011, 23:4289-4292.
Xu et al., "Quantitative structure-activity relationship study on BTK inhibitors by modified multivariate adaptive regression spline and CoMSIA methods," SAR QSAR Environ Res., 2015, 26(4):279-300.
Xu et al., "Design, synthesis and biological evaluation of deuterated nintedanib for improving pharmacokinetic properties," J Label Compd RadioPharm., Jun. 15, 2015, 58(7):308-312.
Yin et al., "Strategies for Targeting Protein-Protein Interactions With Synthetic Agents," Angew. Chem. Int. Ed., 2005, 44:4130-4163.
Young et al., "Discovery of highly potent and selective Bruton's tyrosine kinase inhibitors: Pyridazinone analogs with improved metabolic stability," Bioorganic & Medicinal Chemistry Letters, 2016, 26(2):575-579.
Young et al., "Potent and selective Bruton's tyrosine kinase inhibitors: Discovery of GDC-0834," Bioorganic & Medicinal Chemistiy Letters, 2015, 25(6):1333-1337.
Zarganes-Tzitzikas, "Inhibitors of programmed cell death 1 (PD-1): a patent review (2010-2015)," Expert Opinion on Therapeutic Patents, Sep. 19, 2016, 26(9):973-977.
Zak et al., "Structural basis for small molecule targeting of the programmed death ligand 1 (PD-L1)," Oncotarget, 2016, 7(21):30323-30335.
Zak et al., "Structural basis for small molecule targeting of the programmed death ligand 1 (PD-L1)" Oncotarget, Apr. 2016, 19 pages; Supplemental Material for 2016, 7(21):30323-30335.
Zak et al., "Structure of the Complex of Human Programmed Death 1, PD-1, and Its Ligand PD-L1: with Supplemental Information," Structure, Dec. 2015, 23:2341-2348.
Zang et al., "Four 2D metal-organic networks incorporating Cd-cluster SUBs: hydrothermal synthesis, structures and photoluminescent properties," CrystEngComm, 2009, 11(1):122-129.
Zhan et al., "From monoclonal antibodies to small molecules: the development of inhibitors targeting the PD-1/PD-L1 pathway," Drug Discovery Today, Apr. 2016, 10 pages.
Zhang et al., "Electrospray mass spectrum of a per(onio)-substituted benzene: retention of Coulombic charge upon collisionally activated decomposition," J Am Soc. Mass. Spectrom., 1998, 9(1):15-20.
Zhang et al., "Non-symmetrical diarylcarboxylic acids via rhodium(I)-catalyzed regiospecific cross-dehydrogenation coupling of aromatic acids: twofold direct C—H bond activations in water," RSC Advances, 2016, 6(64):91617-91620.
Zhang et al., "Structural and Functional Analysis of the Costimulatory Receptor Programmed Death-1," Immunity, Mar. 2004, 20:337-347.
Zhang et al., "Biaryl-Based Macrocyclic and Polymeric Chiral (Salophen)Ni(II) Complexes: Synthesis and Spectroscopic Study," J Org Chem., 2001, 66(2):481-487.
Zhao et al., "Design, synthesis and organocatalysis of 2,2'-biphenol-based prolinamide organocatalysts in the asymmetric direct aldol reaction in water," Synlett, 2013, 24(20):2743-2747.
Argentina Office Action in Argentina Application No. 20170103634, dated Jan. 27, 2022, 7 pages.
Australian Notice of Allowance in Australian Application No. 2017382870, dated Mar. 15, 2022, 4 pages.
Azuma et al., "B7—H1 is a ubiquitous antiapoptotic receptor on cancer cells," Blood, Apr. 1, 2018, 111(7):3635-3643.
Bastin et al., "Salt Selection and Optimisation for Pharmaceutical New Chemical Entities," Org Proc Res Dev., dated Jan. 1, 2000, pp. 4(5):427-435.
Caira, "Crystalline Polymorphism of Organic Compounds," Topics in Current Chemistry, Jan. 1, 1998, 198:163-208.
Cheng et al., "Cancer-associated fibroblasts induce PDL1+ neutrophils through the IL6-STAT3 pathway that foster immune suppression in hepatocellular carcinoma," Cell Death and Disease, 2018, 9:422.
Dong et al., "Tumor-associated B7—H1 promotes T-cell apoptosis: a potential mechanism of immune evasion," Nature Medicine, Aug. 2002, 8(8):793-800.
European Communication in European Application No. 20202254.7, dated Apr. 1, 2022, 4 pages.
Highlights Prescribing Information, "Opdivo," Revised Apr. 2019, 90 pages.
Highlights Prescribing Information, "Keytruda," Revised Feb. 2019, 66 pages.
Indian Office Action in Indian Application No. 202017053661, dated Jun. 3, 2022, 5 pages.
International Preliminary Report on Patentability in International Application No. PCT/US2020/045311, dated Feb. 17, 2022, 8 pages.
International Preliminary Report on Patentability in International Application No. PCT/US2020/053190, dated Apr. 5, 2022, 7 pages.
International Preliminary Report on Patentability in International Application No. PCT/US2020/059817, dated May 17, 2022, 12 pages.
International Search Report and Written Opinion in International Application No. PCT/US2021/058338, dated Feb. 9, 2022, 15 pages.
International Search Report and Written Opinion in International Application No. PCT/US2021/058334, dated Apr. 25, 2022, 23 pages.
International Search Report and Written Opinion in International Application No. PCT/US2021/063965, dated Apr. 12, 2022, 20 pages.
International Search Report and Written Opinion in International Application No. PCT/US2021/058268, dated Apr. 21, 2022, 22 pages.
Invitation to Pay Fee's in International Application No. PCT/US2021/058268, dated Jan. 31, 2022, 16 pages.
Invitation to Pay Fee's in International Application No. PCT/US2021/058334, dated Feb. 3, 2022, 12 pages.
Israeli Office Action in Israeli Application No. 287,267, dated Feb. 15, 2022, 4 pages.
Reck et al., "Pembrolizumab versus Chemotherapy for PD-L1-Positive Non-Small-Cell Lung Cancer," N Engl J Med., Nov. 10, 2016, 375(19):1823-1833.
Rowe et al., "Fumaric Acid" Handbook of pharmaceutical excipients, Jan. 1, 2009, pp. 276-277, 309-310, 393-396.

(56) References Cited

OTHER PUBLICATIONS

Stahl et al., "Handbook of Pharmaceutical Salts: Properties, Selection, and Use," Wiley, 2002, p. 329-350.
Sznol et al., "Antagonist Antibodies to PD-1 and B7—H1 (PD-L1) in the Treatment of Advanced Human Cancer," Clin Cancer Res., Mar. 1, 2013, 19(5):1021-1034.
Vaddepally et al., "Review of Indications of FDA-Approved Immune Checkpoint Inhibitors per NCCN Guidelines with the Level of Evidence," Cancers, 2020, 12(3):738.

HETEROCYCLIC COMPOUNDS AS IMMUNOMODULATORS

CLAIM OF PRIORITY

This application is a continuation of U.S. patent application Ser. No. 16/781,927, filed on Feb. 4, 2020; which is a continuation of U.S. patent application Ser. No. 16/444,797, filed on Jun. 18, 2019; which is a continuation of U.S. patent application Ser. No. 16/170,827, filed on Oct. 25, 2018; which is a continuation of U.S. patent application Ser. No. 15/906,655, filed on Feb. 27, 2018; which is a continuation of U.S. patent application Ser. No. 15/587,466, filed on May 5, 2017; which claims the benefit of U.S. Provisional Application No. 62/332,655, filed on May 6, 2016, each of which is incorporated herein by reference in its entirety.

FIELD OF THE INVENTION

The present application is concerned with pharmaceutically active compounds. The disclosure provides compounds as well as their compositions and methods of use. The compounds modulate PD-1/PD-L1 protein/protein interaction and are useful in the treatment of various diseases including infectious diseases and cancer.

BACKGROUND OF THE INVENTION

The immune system plays an important role in controlling and eradicating diseases such as cancer. However, cancer cells often develop strategies to evade or to suppress the immune system in order to favor their growth. One such mechanism is altering the expression of co-stimulatory and co-inhibitory molecules expressed on immune cells (Postow et al, J. Clinical Oncology 2015, 1-9). Blocking the signaling of an inhibitory immune checkpoint, such as PD-1, has proven to be a promising and effective treatment modality.

Programmed cell death-1 (PD-1), also known as CD279, is a cell surface receptor expressed on activated T cells, natural killer T cells, B cells, and macrophages (Greenwald et al, Annu. Rev. Immunol 2005, 23:515-548; Okazaki and Honjo, Trends Immunol 2006, (4):195-201). It functions as an intrinsic negative feedback system to prevent the activation of T-cells, which in turn reduces autoimmunity and promotes self-tolerance. In addition, PD-1 is also known to play a critical role in the suppression of antigen-specific T cell response in diseases like cancer and viral infection (Sharpe et al, *Nat Immunol* 2007 8, 239-245; Postow et al, J. Clinical Oncol 2015, 1-9).

The structure of PD-1 consists of an extracellular immunoglobulin variable-like domain followed by a transmembrane region and an intracellular domain (Parry et al, Mol Cell Biol 2005, 9543-9553). The intracellular domain contains two phosphorylation sites located in an immunoreceptor tyrosine-based inhibitory motif and an immunoreceptor tyrosine-based switch motif, which suggests that PD-1 negatively regulates T cell receptor-mediated signals. PD-1 has two ligands, PD-L1 and PD-L2 (Parry et al, Mol Cell Biol 2005, 9543-9553; Latchman et al, Nat Immunol 2001, 2, 261-268), and they differ in their expression patterns. PD-L1 protein is upregulated on macrophages and dendritic cells in response to lipopolysaccharide and GM-CSF treatment, and on T cells and B cells upon T cell receptor and B cell receptor signaling. PD-L1 is also highly expressed on almost all tumor cells, and the expression is further increased after IFN-γ treatment (Iwai et al, PNAS2002, 99(19):12293-7; Blank et al, Cancer Res 2004, 64(3):1140-5). In fact, tumor PD-L1 expression status has been shown to be prognostic in multiple tumor types (Wang et al, Eur J Surg Oncol 2015; Huang et al, Oncol Rep 2015; Sabatier et al, Oncotarget 2015, 6(7): 5449-5464). PD-L2 expression, in contrast, is more restricted and is expressed mainly by dendritic cells (Nakae et al, J Immunol 2006, 177:566-73). Ligation of PD-1 with its ligands PD-L1 and PD-L2 on T cells delivers a signal that inhibits IL-2 and IFN-γ production, as well as cell proliferation induced upon T cell receptor activation (Carter et al, Eur J Immunol 2002, 32(3):634-43; Freeman et al, J Exp Med 2000, 192(7):1027-34). The mechanism involves recruitment of SHP-2 or SHP-1 phosphatases to inhibit T cell receptor signaling such as Syk and Lck phosphorylation (Sharpe et al, Nat Immunol 2007, 8, 239-245). Activation of the PD-1 signaling axis also attenuates PKC-θ activation loop phosphorylation, which is necessary for the activation of NF-κB and AP1 pathways, and for cytokine production such as IL-2, IFN-γ and TNF (Sharpe et al, Nat Immunol 2007, 8, 239-245; Carter et al, Eur J Immunol 2002, 32(3):634-43; Freeman et al, J Exp Med 2000, 192(7):1027-34).

Several lines of evidence from preclinical animal studies indicate that PD-1 and its ligands negatively regulate immune responses. PD-1-deficient mice have been shown to develop lupus-like glomerulonephritis and dilated cardiomyopathy (Nishimura et al, Immunity 1999, 11:141-151; Nishimura et al, Science 2001, 291:319-322). Using an LCMV model of chronic infection, it has been shown that PD-1/PD-L1 interaction inhibits activation, expansion and acquisition of effector functions of virus-specific CD8 T cells (Barber et al, Nature 2006, 439, 682-7). Together, these data support the development of a therapeutic approach to block the PD-1-mediated inhibitory signaling cascade in order to augment or "rescue" T cell response. Accordingly, there is a need for new compounds that block PD-1/PD-L1 protein/protein interaction.

SUMMARY

The present disclosure provides, inter alia, a compound of Formula (I):

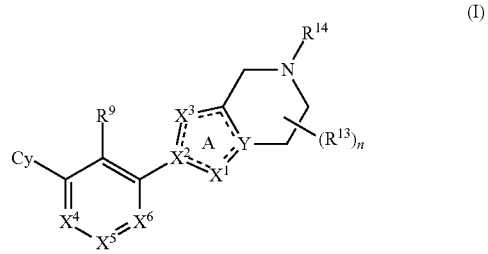

or a pharmaceutically acceptable salt or a stereoisomer thereof, wherein constituent variables are defined herein.

The present disclosure further provides a pharmaceutical composition comprising a compound of the disclosure, or a pharmaceutically acceptable salt or a stereoisomer thereof, and at least one pharmaceutically acceptable carrier or excipient.

The present disclosure further provides methods of modulating or inhibiting PD-1/PD-L1 protein/protein interaction, which comprises administering to an individual a compound of the disclosure, or a pharmaceutically acceptable salt or a stereoisomer thereof.

3

The present disclosure further provides methods of treating a disease or disorder in a patient comprising administering to the patient a therapeutically effective amount of a compound of the disclosure, or a pharmaceutically acceptable salt or a stereoisomer thereof.

DETAILED DESCRIPTION

I. Compounds

The present disclosure provides a compound of Formula (I):

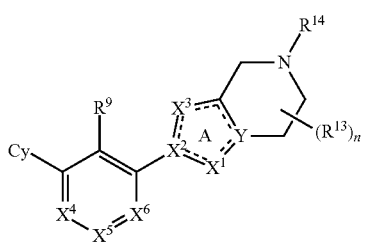

or a pharmaceutically acceptable salt or a stereoisomer thereof, wherein:

$X^1$ is O, S, N, $NR^1$ or $CR^1$;

$X^2$ is N or C;

$X^3$ is O, S, N, $NR^3$ or $CR^3$;

$X^4$ is N or $CR^4$;

$X^5$ is N or $CR^5$;

$X^6$ is N or $CR^6$;

Y is C or N;

at least one of $X^1$, $X^2$, $X^3$ and Y is a heteroatom selected from N, O and S;

Cy is $C_{6-10}$ aryl, $C_{3-10}$ cycloalkyl, 5- to 14-membered heteroaryl, or 4- to 10-membered heterocycloalkyl, each of which is optionally substituted with 1 to 5 independently selected $R^7$ substituents;

$R^1$, $R^3$, $R^4$, $R^5$ and $R^6$ are each independently selected from H, $C_{1-4}$ alkyl, $C_{3-4}$ cycloalkyl, $C_{2-4}$ alkenyl, $C_{2-4}$ alkynyl, halo, CN, OH, $C_{1-4}$ alkoxy, $C_{1-4}$ haloalkyl, $C_{1-4}$ haloalkoxy, $NH_2$, —NH—$C_{1-4}$ alkyl, —N($C_{1-4}$ alkyl)$_2$, $NHOR^{10}$, $C(O)R^{10}$, $C(O)NR^{10}R^{10}$, $C(O)OR^{10}$, $OC(O)R^{10}$, $OC(O)NR^{10}R^{10}$, $NR^{10}C(O)R^{10}$, $NR^{10}C(O)OR^{10}$, $NR^{10}C(O)NR^{10}R^{10}$, $C(=NR^{10})R^{10}$, $C(=NR^{10})NR^{10}R^{10}$, $NR^{10}C(=NR^{10})NR^{10}R^{10}$, $NR^{10}S(O)R^{10}$, $NR^{10}S(O)_2R^{10}$, $NR^{10}S(O)_2NR^{10}R^{10}$, $S(O)R^{10}$, $S(O)NR^{10}R^{10}$, $S(O)_2R^{10}$, and $S(O)_2NR^{10}R^{10}$, wherein each $R^{10}$ is independently selected from H and $C_{1-4}$ alkyl optionally substituted with 1 or 2 groups independently selected from halo, OH, CN and $C_{1-4}$ alkoxy; and wherein the $C_{1-4}$ alkyl, $C_{3-4}$ cycloalkyl, $C_{2-4}$ alkenyl, $C_{2-4}$ alkynyl and $C_{1-4}$ alkoxy of $R^1$, $R^3$, $R^4$, $R^5$ and $R^6$ are each optionally substituted with 1 or 2 substituents independently selected from halo, OH, CN and $C_{1-4}$ alkoxy;

$R^9$ is $C_{1-4}$ alkyl, halo, CN, OH, cyclopropyl, $C_{2-4}$ alkenyl, $C_{2-4}$ alkynyl, $C_{1-4}$ alkoxy, $C_{1-4}$ haloalkyl, $C_{1-4}$ haloalkoxy, $NH_2$, —NH—$C_{1-4}$ alkyl, —N($C_{1-4}$ alkyl)$_2$, $NHOR^{11}$, $C(O)R^{11}$, $C(O)NR^{11}R^{11}$, $C(O)OR^{11}$, $OC(O)R^{11}$, $OC(O)NR^{11}R^{11}$, $NR^{11}C(O)R^{11}$, $NR^{11}C(O)OR^{11}$, $NR^{11}C(O)NR^{11}R^{11}$, $C(=NR^{11})R^{11}$, $C(=NR^{11})NR^{11}R^{11}$, $NR^{11}C(=NR^{11})NR^{11}R^{11}$, $NR^{11}S(O)R^{11}$, $NR^{11}S(O)_2R^{11}$, $NR^{11}S(O)_2NR^{11}R^{11}$, $S(O)R^{11}$, $S(O)NR^{11}R^{11}$, $S(O)_2R^{11}$, and $S(O)_2NR^{11}R^{11}$, wherein $C_{1-4}$ alkyl, cyclopropyl, $C_{2-4}$ alkenyl, $C_{2-4}$ alkynyl and $C_{1-4}$ alkoxy of $R^9$ are each optionally substituted with 1 or 2 substituents selected from halo, OH, CN and

4

$OCH_3$ and each $R^{11}$ is independently selected from H and $C_{1-4}$ alkyl optionally substituted with 1 or 2 halo, OH, CN or $OCH_3$ substituents;

$R^7$, $R^{13}$ and $R^{14}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-(5-14 membered heteroaryl)-$C_{1-4}$ alkyl-, (4-10 membered heterocycloalkyl)-$C_{1-4}$ alkyl-, CN, $NO_2$, $OR^a$, SR, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- of $R^7$, $R^{13}$ and $R^{14}$ are each optionally substituted with 1, 2, 3, or 4 $R^b$ substituents;

or two adjacent $R^7$ substituents on the Cy ring, taken together with the atoms to which they are attached, form a fused phenyl ring, a fused 5-, 6- or 7-membered heterocycloalkyl ring, a fused 5- or 6-membered heteroaryl ring or a fused $C_{3-6}$ cycloalkyl ring, wherein the fused 5-, 6- or 7-membered heterocycloalkyl ring and fused 5- or 6-membered heteroaryl ring each have 1-4 heteroatoms as ring members selected from N, O and S and wherein the fused phenyl ring, fused 5-, 6- or 7-membered heterocycloalkyl ring, fused 5- or 6-membered heteroaryl ring and fused $C_{3-6}$ cycloalkyl ring are each optionally substituted with 1, 2 or 3 independently selected $R^b$ substituents;

or two $R^{13}$ substituents attached to the same carbon atom, taken together with the carbon atom to which they are attached, form a $C_{3-6}$ cycloalkyl ring or 4-, 5-, 6- or 7-membered heterocycloalkyl ring, wherein the $C_{3-6}$ cycloalkyl ring and 4-, 5-, 6- or 7-membered heterocycloalkyl ring are each optionally substituted with 1, 2 or 3 independently selected $R^b$ substituents;

each $R^a$ is independently selected from H, CN, $C_{1-6}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^a$ are each optionally substituted with 1, 2, 3, 4, or 5 $R^d$ substituents;

each $R^d$ is independently selected from $C_{1-4}$ alkyl, $C_{1-4}$ haloalkyl, halo, $C_{3-10}$ cycloalkyl, 4-10 membered heterocycloalkyl, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $S(O)R^e$, $S(O)NR^e$, $S(O)_2R^e$, $NR^eS(O)_2R^e$, $NR^eS(O)_2NR^eR^e$, and $S(O)_2NR^eR^e$, wherein the $C_{1-4}$ alkyl, $C_{3-10}$ cycloalkyl and 4-10 membered heterocycloalkyl of $R^d$ are each further optionally substituted with 1-3 independently selected $R^q$ substituents;

each R substituent is independently selected from halo, $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$; wherein the $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1-3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 $R^f$ substituents independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $NR^gS(O)_2R^g$, $NR^gS(O)_2NR^gR^g$, and $S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of R are each optionally substituted with 1, 2, 3, 4, or 5 $R^n$ substituents independently selected from $C_{1-4}$ alkyl, $C_{1-4}$ haloalkyl, halo, CN, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR^o)NR^oR^o$, $NR^oC(=NR^o)NR^oR^o$, $S(O)R^o$, $S(O)NR^oR^o$, $S(O)_2R^o$, $NR^oS(O)_2R^o$, $NR^oS(O)_2NR^oR^o$, and $S(O)_2NR^oR^o$;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1-3 independently selected $R^p$ substituents;

or any two $R^a$ substituents together with the nitrogen atom to which they are attached form a 4-, 5-, 6-, 7-, 8-, 9- or 10-membered heterocycloalkyl group optionally substituted with 1, 2 or 3 $R^h$ substituents independently selected from $C_{1-6}$ alkyl, $C_{3-10}$ cycloalkyl, 4-7 membered heterocycloalkyl, $C_{6-10}$ aryl, 5-6 membered heteroaryl, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{2-6}$ alkenyl, $C_{2-6}$ alkynyl, halo, CN, $OR^i$, $SR^i$, $NHOR^i$, $C(O)R^i$, $C(O)NR^iR^i$, $C(O)OR^i$, $OC(O)R^i$, $OC(O)NR^iR^i$, $NHR^i$, $NR^iR^i$, $NR^iC(O)R^i$, $NR^iC(O)NR^iR^i$, $NR^iC(O)OR^i$, $C(=NR^i)NR^iR^i$, $NR^iC(=NR^i)NR^iR^i$, $S(O)R^i$, $S(O)NR^iR^i$, $S(O)_2R^i$, $NR^iS(O)_2R^i$, $NR^iS(O)_2NR^iR^i$, and $S(O)_2NR^iR^i$, wherein the $C_{1-6}$ alkyl, $C_{3-10}$ cycloalkyl, 4-7 membered heterocycloalkyl, $C_{6-10}$ aryl, 5-6 membered heteroaryl, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl- of $R^h$ are each further optionally substituted by 1, 2, or 3 $R^i$ substituents independently selected from $C_{3-6}$ cycloalkyl, $C_{6-10}$ aryl, 5 or 6-membered heteroaryl, $C_{2-4}$ alkenyl, $C_{2-4}$ alkynyl, halo, $C_{1-4}$ alkyl, $C_{1-4}$ haloalkyl, CN, $NHOR^k$, $OR^k$, $SR^k$, $C(O)R^k$, $C(O)NR^kR^k$, $C(O)OR^k$, $OC(O)R^k$, $OC(O)NR^kR^k$, $NHR^k$, $NR^kR^k$, $NR^kC(O)R^k$, $NR^kC(O)NR^kR^k$, $NR^kC(O)OR^k$, $C(=NR^k)NR^kR^k$, $NR^kC(=NR^k)NR^kR^k$, $S(O)R^k$, $S(O)NR^kR^k$, $S(O)_2R^k$, $NR^kS(O)_2R^k$, $NR^kS(O)_2NR^kR^k$, and $S(O)_2NR^kR^k$;

or two $R^h$ groups attached to the same carbon atom of the 4- to 10-membered heterocycloalkyl taken together with the carbon atom to which they are attached form a $C_{3-6}$ cycloalkyl or 4- to 6-membered heterocycloalkyl having 1-2 heteroatoms as ring members selected from O, N or S;

or any two $R^c$ substituents together with the nitrogen atom to which they are attached form a 4-, 5-, 6-, or 7-membered heterocycloalkyl group optionally substituted with 1, 2, or 3 independently selected $R^h$ substituents;

or any two $R^e$ substituents together with the nitrogen atom to which they are attached form a 4-, 5-, 6-, or 7-membered heterocycloalkyl group optionally substituted with 1, 2, or 3 independently selected $R^h$ substituents;

or any two $R^g$ substituents together with the nitrogen atom to which they are attached form a 4-, 5-, 6-, or 7-membered heterocycloalkyl group optionally substituted with 1, 2, or 3 independently selected $R^h$ substituents;

or any two $R^i$ substituents together with the nitrogen atom to which they are attached form a 4-, 5-, 6-, or 7-membered heterocycloalkyl group optionally substituted with 1, 2, or 3 independently selected $R^h$ substituents;

or any two $R^k$ substituents together with the nitrogen atom to which they are attached form a 4-, 5-, 6-, or 7-membered heterocycloalkyl group optionally substituted with 1, 2, or 3 independently selected $R^h$ substituents;

or any two $R^o$ substituents together with the nitrogen atom to which they are attached form a 4-, 5-, 6-, or 7-membered heterocycloalkyl group optionally substituted with 1, 2, or 3 independently selected $R^h$ substituents; and each $R^e$, $R^i$, $R^k$, $R^o$ or $R^p$ is independently selected from H, $C_{1-4}$ alkyl, $C_{3-6}$ cycloalkyl, $C_{6-10}$ aryl, 5 or 6-membered heteroaryl, $C_{1-4}$ haloalkyl, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, $C_{2-4}$ alkenyl, and $C_{2-4}$ alkynyl of $R^e$, $R^i$, $R^k$, $R^o$ or $R^p$ are each optionally substituted with 1, 2 or 3 $R^q$ substituents;

each $R^q$ is independently selected from OH, CN, —COOH, $NH_2$, halo, $C_{1-6}$haloalkyl, $C_{1-6}$ alkyl, $C_{1-6}$ alkoxy, $C_{1-6}$ haloalkoxy, $C_{1-6}$ alkylthio, phenyl, 5-6 membered heteroaryl, 4-6 membered heterocycloalkyl, $C_{3-6}$ cycloalkyl, $NHR^{12}$, $NR^{12}R^{12}$, and $C_{1-4}$ haloalkoxy, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with halo, OH, CN, —COOH, $NH_2$, $C_{1-4}$ alkoxy, $C_{1-4}$ haloalkyl, $C_{1-4}$ haloalkoxy, phenyl, $C_{3-10}$ cycloalkyl and 4-6 membered heterocycloalkyl and each $R^{12}$ is independently $C_{1-6}$ alkyl;

is a single bond or a double bond to maintain ring A being aromatic;

the subscript n is an integer of 1, 2, 3, 4, 5 or 6; and when $R^9$ is OH, Cy is other than 6-carbamimidoyl-1H-benzo[d]imidazol-2-yl.

The compounds, or pharmaceutically acceptable salts or stereoisomers thereof, as described herein are useful as inhibitors of the PD-1/PD-L1 protein/protein interaction. For example, compounds or pharmaceutically acceptable salts or stereoisomers thereof as described herein can disrupt the PD-1/PD-L1 protein/protein interaction in the PD-1 pathway.

In some embodiments of compounds of Formula (I), when $R^9$ is OH, Cy is other than 1H-benzo[d]imidazol-2-yl optionally substituted with a $R^7$ substituent.

In some embodiments of compounds of Formula (I), $R^7$, $R^{13}$ and $R^{14}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, NO$_2$, OR$^a$, SR$^a$, NHOR$^a$, C(O)R$^a$, C(O)NR$^a$R$^a$, C(O)OR$^a$, OC(O)R$^a$, OC(O)NR$^a$R$^a$, NHR$^a$, NR$^a$R$^a$, NR$^a$C(O)R$^a$, NR$^a$C(O)OR$^a$, NR$^a$C(O)NR$^a$R$^a$, C(=NR$^a$)R$^a$, C(=NR$^a$)NR$^a$R$^a$, NR$^a$C(=NR$^a$)NR$^a$R$^a$, NR$^a$S(O)R$^a$, NR$^a$S(O)$_2$R$^a$, NR$^a$S(O)$_2$NR$^a$R$^a$, S(O)R$^a$, S(O)NR$^a$R$^a$, S(O)$_2$ R$^a$, and S(O)$_2$NR$^a$R$^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- of $R^7$, $R^{13}$ and $R^{14}$ are each optionally substituted with 1, 2, 3, or 4 $R^q$ substituents.

In some embodiments of compounds of Formula (I), two adjacent $R^7$ substituents on the Cy ring, taken together with the atoms to which they are attached, form a fused phenyl ring, a fused 5-, 6- or 7-membered heterocycloalkyl ring, a fused 5- or 6-membered heteroaryl ring or a fused $C_{3-6}$ cycloalkyl ring, wherein the fused 5-, 6- or 7-membered heterocycloalkyl ring and fused 5- or 6-membered heteroaryl ring each have 1-4 heteroatoms as ring members selected from N, O and S and wherein the fused phenyl ring, fused 5-, 6- or 7-membered heterocycloalkyl ring, fused 5- or 6-membered heteroaryl ring and fused $C_{3-6}$ cycloalkyl ring are each optionally substituted with 1, 2 or 3 independently selected $R^q$ substituents.

In some embodiments of compounds of Formula (I), Cy is $C_{6-10}$ aryl, optionally substituted with 1 to 5 independently selected $R^7$ substituents. In certain embodiments, Cy is phenyl or naphthyl, each of which is optionally substituted with 1 to 4 independently selected $R^7$ substituents. In certain embodiments, Cy is phenyl optionally substituted with 1 to 5 independently selected $R^7$ substituents. In certain embodiments, Cy is unsubstituted phenyl. In certain embodiments, Cy is 2,3-dihydro-1,4-benzodioxin-6-yl, optionally substituted with 1 to 5 independently selected $R^7$ substituents.

In some embodiments of compounds of Formula (I), Cy is $C_{3-10}$ cycloalkyl, optionally substituted with 1 to 5 independently selected $R^7$ substituents. In certain embodiments, Cy is cyclopropyl, cyclobutyl, cyclopentyl, cyclohexyl, cyclohexenyl, cycloheptyl or cyclooctyl, each of which is optionally substituted with 1 to 5 independently selected $R^7$ substituents.

In some embodiments of compounds of Formula (I), Cy is 5- to 14-membered heteroaryl, optionally substituted with 1 to 5 independently selected $R^7$ substituents. In certain embodiments, Cy is pyridy, primidinyl, pyrazinyl, pyridazinyl, triazinyl, pyrrolyl, pyrazolyl, azolyl, oxazolyl, thiazolyl, imidazolyl, furanyl, thiophenyl, quinolinyl, isoquinolinyl, naphthyridinyl, indolyl, benzothiophenyl, benzofuranyl, benzisoxazolyl, imidazo[1,2-b]thiazolyl, purinyl, thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl, each of which is optionally substituted with 1 to 5 independently selected $R^7$ substituents. In certain embodiments, Cy is thiophenyl or pyridyl, each of which is optionally substituted with 1 to 5 independently selected $R^7$ substituents. In some embodiments, Cy is 2-thiophenyl, 3-thiophenyl, 2-pyridyl, 3-pyridyl or 4-pyridyl, each of which is optionally substituted with 1 to 5 independently selected $R^7$ substituents.

In some embodiments of compounds of Formula (I), Cy is 4- to 10-membered heterocycloalkyl, optionally substituted with 1 to 5 independently selected $R^7$ substituents. In certain embodiments, Cy is azetidinyl, azepanyl, dihydrobenzofuranyl, dihydrofuranyl, dihydropyranyl, morpholino, 3-oxa-9-azaspiro[5.5]undecanyl, 1-oxa-8-azaspiro[4.5]decanyl, piperidinyl, piperazinyl, oxopiperazinyl, pyranyl, pyrrolidinyl, quinuclidinyl, tetrahydrofuranyl, tetrahydropyranyl, 1,2,3,4-tetrahydroquinolinyl, tropanyl, 2,3-dihydro-1,4-benzodioxin-6-yl, and thiomorpholino, each of which is optionally substituted with 1 to 4 independently selected $R^7$ substituents. In some embodiments, Cy is 3,6-dihydro-2H-pyran-4-yl, optionally substituted with 1 to 5 independently selected $R^7$ substituents.

In some embodiments of compounds of Formula (I), Cy is phenyl, 5- or 6-membered heteroaryl, $C_{3-6}$ cycloalkyl or 5- or 6-membered heterocycloalkyl, each of which is optionally substituted with 1 to 5 independently selected $R^7$ substituents. In certain instances, Cy is phenyl, 2-thiophenyl, 3-thiophenyl, 2-pyridyl, 3-pyridyl, 4-pyridyl, $C_{3-6}$ cycloalkyl or 3,6-dihydro-2H-pyran-4-yl, each of which is optionally substituted with 1 to 5 $R^7$ substituents.

In some embodiments of compounds of Formula (I), $X^4$ is $CR^4$, $X^5$ is $CR^5$ and $X^6$ is $CR^6$. In certain instances, $R^4$, $R^5$ and $R^6$ are each H.

In some embodiments of compounds of Formula (I), $X^4$ is $CR^4$, $X^5$ is N and $X^6$ is N. In certain instances, $R^4$ is H.

In some embodiments of compounds of Formula (I), $X^4$ is $CR^4$, $X^5$ is N and $X^6$ is $CR^6$. In certain instances, $R^4$ and $R^6$ are each H.

In some embodiments of compounds of Formula (I), $X^4$ is $CR^4$, $X^5$ is $CR^5$ and $X^6$ is N. In certain instances, $R^4$ and $R^5$ are each H.

In some embodiments of compounds of Formula (I), $X^4$ is N, $X^5$ is $CR^5$ and $X^6$ is $CR^6$. In certain instances, $R^5$ and $R^6$ are each H.

In some embodiments of compounds of Formula (I), $X^4$ is N, $X^5$ is N and $X^6$ is $CR^6$. In certain instances, $R^6$ is H.

In some embodiments of compounds of Formula (I), $X^4$ is N, $X^5$ is $CR^5$ and $X^6$ is N. In certain instances, $R^5$ is H.

In some embodiments, the present disclosure provides compounds having Formula

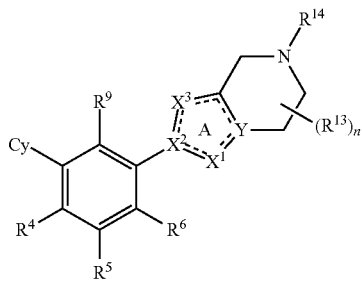

(II)

or a pharmaceutically acceptable salt or a stereoisomer thereof, wherein the variables of Formula (II) are as defined in Formula (I) or any embodiment of compounds of Formula (I) as described herein. In one embodiment of compounds of Formula (II), $R^9$ is halo, CN or $C_{1-4}$ alkyl optionally substituted with 1 or 2 $R^q$ groups. In another embodiment, $R^9$ is Cl, $CH_3$ or CN.

In some embodiments, the present disclosure provides compounds having Formula (IIa):

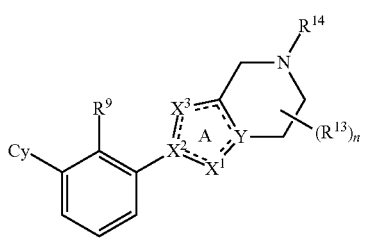

(IIa)

or a pharmaceutically acceptable salt or a stereoisomer thereof, wherein the variables of Formula (IIa) are as defined in Formula (I) or any embodiment of compounds of Formula (I) as described herein. In one embodiment, Cy is phenyl optionally substituted with 1 to 5 $R^7$ groups. In one embodiment, $R^9$ is halo, CN or $C_{1-4}$ alkyl optionally substituted with 1 or 2 $R^q$ groups. In another embodiment, $R^9$ is Cl, $CH_3$ or CN.

In some embodiments, the present disclosure provides compounds having Formula (III):

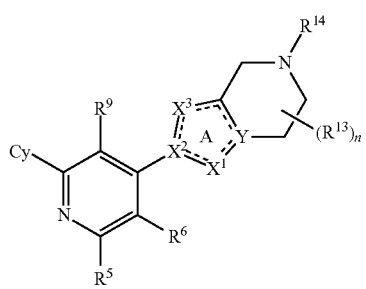

(III)

or a pharmaceutically acceptable salt or a stereoisomer thereof, wherein the variables of Formula (III) are as defined in Formula (I) or any embodiment of compounds of Formula (I) as described herein. In one embodiment, Cy is phenyl optionally substituted with 1 to 5 $R^7$ groups. In one embodiment, $R^5$ and $R^6$ are H. In one embodiment, $R^9$ is halo, CN or $C_{1-4}$ alkyl optionally substituted with 1 or 2 $R^q$ groups. In another embodiment, $R^9$ is Cl, $CH_3$ or CN.

In some embodiments, the present disclosure provides compounds having Formula (IV):

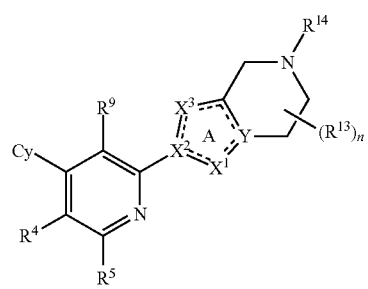

(IV)

or a pharmaceutically acceptable salt or a stereoisomer thereof, wherein the variables of Formula (IV) are as defined in Formula (I) or any embodiment of compounds of Formula (I) as described herein. In one embodiment, Cy is phenyl optionally substituted with 1 to 5 $R^7$ groups. In one embodiment, $R^4$ and $R^5$ are H. In one embodiment, $R^9$ is halo, CN or $C_{1-4}$ alkyl optionally substituted with 1 or 2 $R^q$ groups. In another embodiment, $R^9$ is Cl, $CH_3$ or CN.

In some embodiments, the present disclosure provides compounds having Formula (V):

(V)

or a pharmaceutically acceptable salt or a stereoisomer thereof, wherein the variables of Formula (V) are as defined in Formula (I) or any embodiment of compounds of Formula (I) as described herein. In one embodiment, $R^9$ is halo, CN or $C_{1-4}$ alkyl optionally substituted with 1 or 2 $R^q$ groups. In another embodiment, $R^9$ is Cl, $CH_3$ or CN.

In some embodiments, the present disclosure provides compounds having Formula (VI):

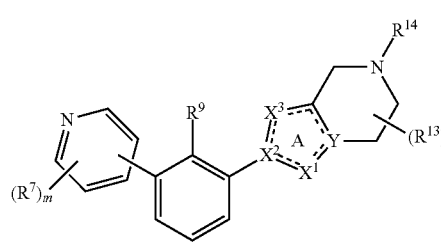

(VI)

or a pharmaceutically acceptable salt or a stereoisomer thereof, wherein the subscript m is an integer of 1, 2, 3 or 4 and the variables of Formula (VI) are as defined in Formula (I) or any embodiment of compounds of Formula (I) as described herein. The moiety

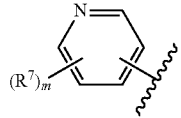

in Formula (VI) is

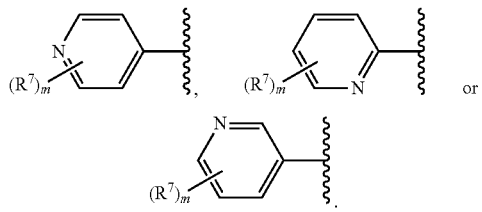

In certain embodiments, the present disclosure provides compounds having Formula (VIa):

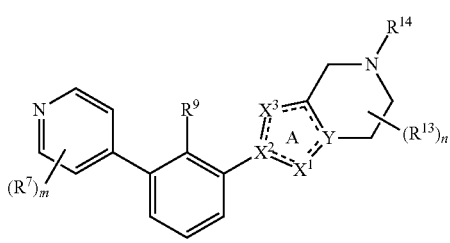

or a pharmaceutically acceptable salt or a stereoisomer thereof, wherein the subscript m is an integer of 1, 2, 3 or 4 and the variables of Formula (VIa) are as defined in Formula (I) or any embodiment of compounds of Formula (I) as described herein.

In certain embodiments, the present disclosure provides compounds having Formula (VIb):

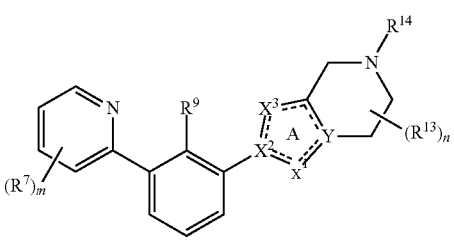

or a pharmaceutically acceptable salt or a stereoisomer thereof, wherein the subscript m is an integer of 1, 2, 3 or 4 and the variables of Formula (VIb) are as defined in Formula (I) or any embodiment of compounds of Formula (I) as described herein.

In certain embodiments, the present disclosure provides compounds having Formula (VIc):

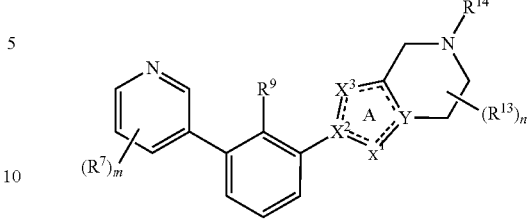

or a pharmaceutically acceptable salt or a stereoisomer thereof, wherein the subscript m is an integer of 1, 2, 3 or 4 and the variables of Formula (VIc) are as defined in Formula (I) or any embodiment of compounds of Formula (I) as described herein.

In some embodiments, the present disclosure provides compounds having Formula (VII):

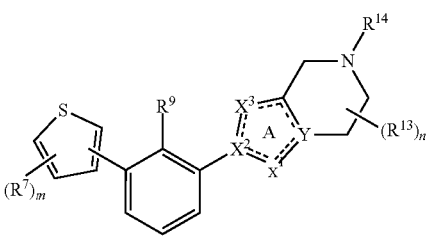

or a pharmaceutically acceptable salt or a stereoisomer thereof, wherein m is an integer of 1, 2 or 3 and the variables of Formula (VII) are as defined in Formula (I) or any embodiment of compounds of Formula (I) as described herein. The moiety

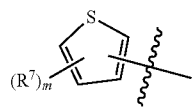

in Formula (VII) is

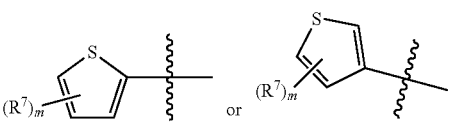

In some embodiments, the present disclosure provides compounds having Formula (VIIa):

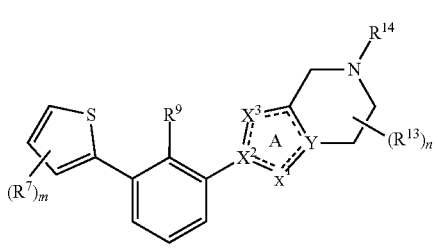

or a pharmaceutically acceptable salt or a stereoisomer thereof, wherein m is an integer of 1, 2 or 3 and the variables of Formula (VIIa) are as defined in Formula (I) or any embodiment of compounds of Formula (I) as described herein.

In some embodiments, the present disclosure provides compounds having Formula (VIIb):

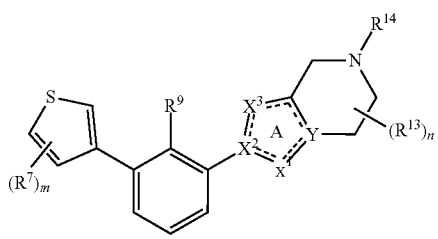

(VIIb)

or a pharmaceutically acceptable salt or a stereoisomer thereof, wherein m is an integer of 1, 2 or 3 and the variables of Formula (VIIb) are as defined in Formula (I) or any embodiment of compounds of Formula (I) as described herein.

In some embodiments of compounds of any of the Formulas as disclosed herein or a pharmaceutically acceptable salt or a stereoisomer thereof, the moiety:

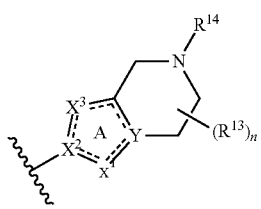

is selected from:

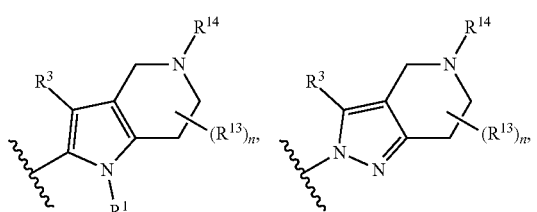

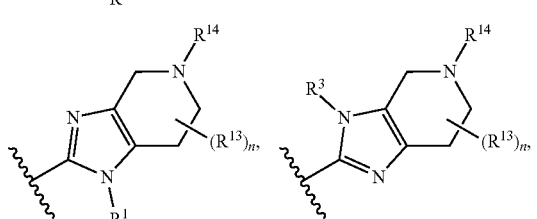

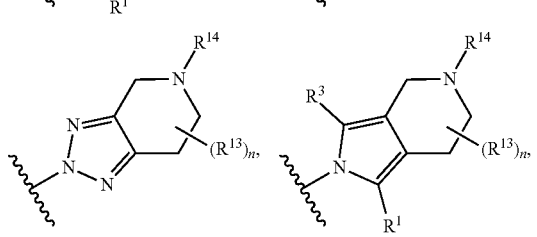

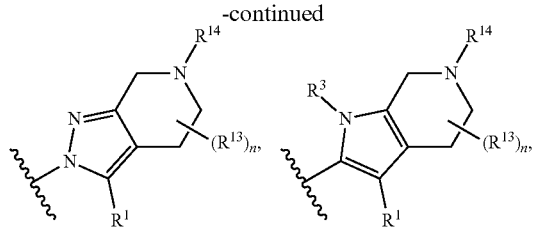

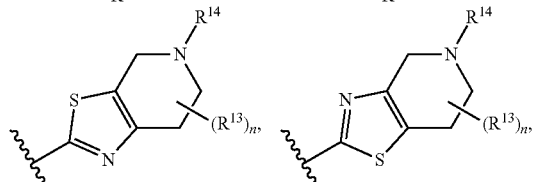

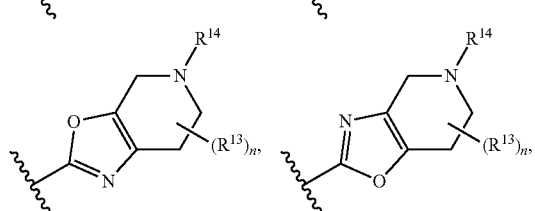

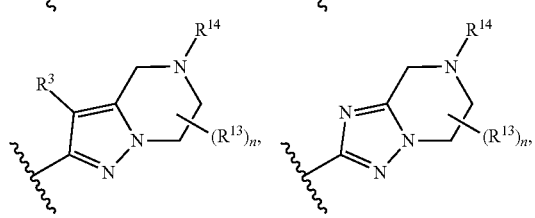

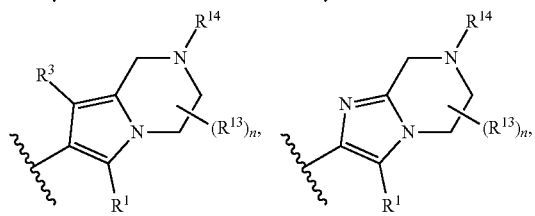

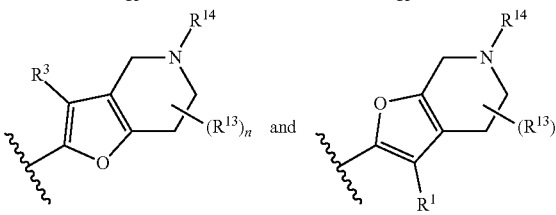

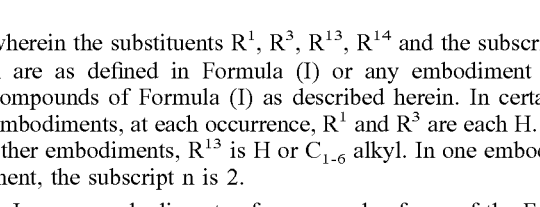

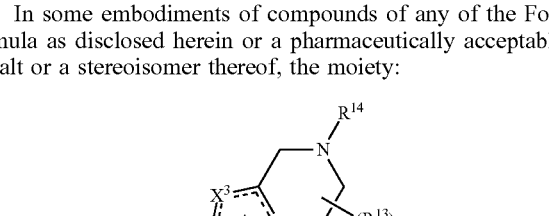

wherein the substituents $R^1$, $R^3$, $R^{13}$, $R^{14}$ and the subscript n are as defined in Formula (I) or any embodiment of compounds of Formula (I) as described herein. In certain embodiments, at each occurrence, $R^1$ and $R^3$ are each H. In other embodiments, $R^{13}$ is H or $C_{1-6}$ alkyl. In one embodiment, the subscript n is 2.

In some embodiments of compounds of any of the Formula as disclosed herein or a pharmaceutically acceptable salt or a stereoisomer thereof, the moiety:

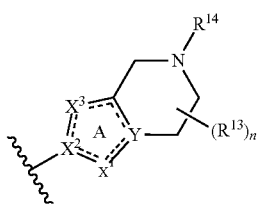

is selected from

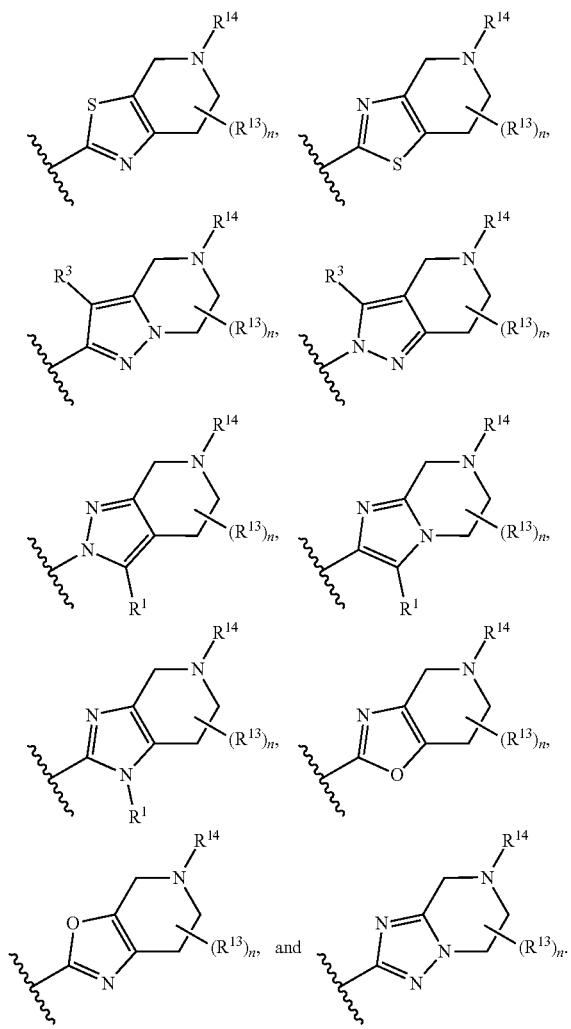

In some embodiments of compounds of any of the Formulas as disclosed herein, $X^1$ is N, $X^2$ is C, $X^3$ is S and Y is C. In some instances, $X^4$, $X^5$ and $X^6$ are each CH.

In some embodiments of compounds of any of the Formulas as disclosed herein, $X^1$ is S, $X^2$ is C, $X^3$ is N, and Y is C. In some instances, $X^4$, $X^5$ and $X^6$ are each CH.

In some embodiments of compounds of any of the Formulas as disclosed herein, $X^1$ is N, $X^2$ is C, $X^3$ is $CR^3$, and Y is N. In some instances, $X^4$, $X^5$ and $X^6$ are each CH.

In some embodiments of compounds of any of the Formulas as disclosed herein, $X^1$ is N, $X^2$ is C, $X^3$ is $NR^3$, and Y is C. In some instances, $X^4$, $X^5$ and $X^6$ are each CH.

In some embodiments of compounds of any of the Formulas as disclosed herein, $X^1$ is N, $X^2$ is C, $X^3$ is S, $X^6$ is N, and Y is C. In some instances, $X^4$ and $X^5$ are each CH.

In some embodiments of compounds of any of the Formulas as disclosed herein, $X^1$ is N, $X^2$ is N, $X^3$ is $CR^3$, and Y is C. In some instances, $X^4$, $X^5$ and $X^6$ are each CH.

In some embodiments of compounds of any of the Formulas as disclosed herein, $X^1$ is $CR^1$, $X^2$ is N, $X^3$ is N, and Y is C. In some instances, $X^4$, $X^5$ and $X^6$ are each CH.

In some embodiments of compounds of any of the Formulas as disclosed herein, $X^1$ is $CR^1$, $X^2$ is C, $X^3$ is N, and Y is N. In some instances, $X^4$, $X^5$ and $X^6$ are each CH.

In some embodiments of compounds of any of the Formulas as disclosed herein, $X^1$ is $NR^1$, $X^2$ is C, $X^3$ is N, and Y is C. In some instances, $X^4$, $X^5$ and $X^6$ are each CH.

In some embodiments of compounds of any of the Formulas as disclosed herein, $X^1$ is N, $X^2$ is C, $X^3$ is O, and Y is C. In some instances, $X^4$, $X^5$ and $X^6$ are each CH.

In some embodiments of compounds of any of the Formulas as disclosed herein, $X^1$ is O, $X^2$ is C, $X^3$ is N, and Y is C. In some instances, $X^4$, $X^5$ and $X^6$ are each CH.

In some embodiments of compounds of any of the Formulas as disclosed herein, $X^1$ is N, $X^2$ is C, $X^3$ is N, and Y is N. In some instances, $X^4$, $X^5$ and $X^6$ are each CH.

In some embodiments of compounds of any of the Formulas as disclosed herein, $X^1$ is N, $X^2$ is C, $X^3$ is S, $X^4$ is N, and Y is C. In some instances, $X^5$ and $X^6$ are each CH.

In some embodiments, $R^1$, $R^3$, $R^4$, $R^5$ and $R^6$ are each H.

In some embodiments, $R^9$ is halo, $C_{1-4}$ alkyl or CN.

In some embodiments, $R^9$ is $CH_3$ or CN. In certain embodiments, $R^9$ is Cl, $CH_3$ or CN. In one embodiment, $R^9$ is $CH_3$. In another embodiment, $R^9$ is CN. In another embodiment, $R^9$ is F, Cl or Br.

In some embodiments, $R^7$ is H.

In some embodiments, $R^4$, $R^5$ and $R^6$ are each H.

In some embodiments of compounds of any of the Formulas as disclosed herein, $R^{13}$ is H or $C_{1-6}$ alkyl.

In some embodiments of compounds of any of the Formulas as disclosed herein, two $R^{13}$ substituents attached to the same carbon atom, taken together with the carbon atom to which they are attached, form a $C_{3-6}$ cycloalkyl ring or 4-, 5-, 6- or 7-membered heterocycloalkyl ring, wherein the $C_{3-6}$ cycloalkyl ring and 4-, 5-, 6- or 7-membered heterocycloalkyl ring are each optionally substituted with 1, 2 or 3 independently selected $R^q$ substituents. Exemplary spiro $C_{3-6}$ cycloalkyl ring formed by two $R^{13}$ substituents include cyclopropyl, cyclobutyl, cyclopentyl and cyclohexyl.

In some embodiments of compounds of any of the Formulas as disclosed herein, $R^{14}$ is H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_3$-10 cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^a$, SR, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^a$-$C(O)OR^a$, $NR^aC(O)NR^aR^a$, $C(=NR^a)R^a$, $C(=NR^a)NR^aR^a$, $NR^aC(=NR^a)NR^aR^a$, $NR^aS(O)R^a$, $NR^aS(O)_2R^a$, $NR^aS(O)_2NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- of $R^{14}$ are each optionally substituted with 1, 2, 3, or 4 $R^b$ substituents or 1, 2, 3 or 4 $R^q$ substituents.

In some embodiments of compounds of any of the Formulas as disclosed herein, $R^{14}$ is H, $C_{1-6}$ alkyl, phenyl, phenyl-$C_{1-4}$ alkyl-, $C_{3-6}$ cycloalkyl, $C_{3-6}$ cycloalkyl-$C_{1-4}$ alkyl-, 5- or 6-membered heteroaryl, 4- to 6-membered heterocycloalkyl, (5- or 6-membered heteroaryl)-$C_{1-4}$ alkyl- or (4- to 6-membered heterocycloalkyl)-$C_{1-4}$ alkyl-, wherein the $C_{1-6}$ alkyl, phenyl, phenyl-$C_{1-4}$ alkyl-, $C_{3-6}$ cycloalkyl, $C_{3-6}$ cycloalkyl-$C_{1-4}$ alkyl-, 5- or 6-membered heteroaryl, 4- to 6-membered heterocycloalkyl, (5- or 6-membered heteroaryl)-$C_{1-4}$ alkyl- or (4- to 6-membered heterocycloalkyl)-$C_{1-4}$ alkyl- of $R^{14}$ is optionally substituted with 1, 2 or 3 $R^q$ substituents.

In some embodiments of compounds of any of the Formulas as disclosed herein, $R^{14}$ is 2-hydroxyethyl, 2-hydroxypropyl, (R)-2-hydroxypropyl, (S)-2-hydroxypropyl, tetrahydro-2H-pyran-4-yl, 4-carboxycyclohexyl, 3-carboxypropyl, 2-carboxycyclopropylmethyl, 1H-pyrazol-4-ylmethyl or 4-cyanomethylcyclohexyl.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula (I) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$—includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methylpropan-1,3-diyl and the like.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The term "amino" refers to a group of formula —NH$_2$.

The term "carbonyl", employed alone or in combination with other terms, refers to a —C(=O)— group, which also may be written as C(O).

The term "cyano" or "nitrile" refers to a group of formula —C≡N, which also may be written as —CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2 (n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "sulfido" refers to a sulfur atom as a divalent substituent, forming a thiocarbonyl group (C—S) when attached to carbon.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms.

Aryl groups include, e.g., phenyl, naphthyl, indanyl, indenyl and the like. In some embodiments, aryl groups have from 6 to about 10 carbon atoms. In some embodiments aryl groups have 6 carbon atoms. In some embodiments aryl groups have 10 carbon atoms. In some embodiments, the aryl group is phenyl. In some embodiments, the aryl group is naphthyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridintl (pyridyl), pyrimidinyl, pyrazinyl, pyridazinyl, pyrrolyl, pyrazolyl, azolyl, oxazolyl, thiazolyl, imidazolyl, furanyl, thiophenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, benzothiophenyl, benzofuranyl, benzisoxazolyl, imidazo[1,2-b]thiazolyl, purinyl, and the like.

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include azetidinyl, azepanyl, dihydrobenzofuranyl, dihydrofuranyl, dihydropyranyl, morpholino, 3-oxa-9-azaspiro[5.5]undecanyl, 1-oxa-8-azaspiro[4.5]decanyl, piperidinyl, piperazinyl, oxopiperazinyl, pyranyl, pyrrolidinyl, quinuclidinyl, tetrahydrofuranyl, tetrahydropyranyl, 1,2,3,4-tetrahydroquinolinyl, tropanyl, and thiomorpholino.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as 3-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

II. Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, Protecting Groups, (Thieme, 2007); Robertson, Protecting Group Chemistry, (Oxford University Press, 2000); Smith et al., *March's Advanced Organic Chemistry*: Reactions, *Mechanisms, and Structure*, 6$^{th}$ Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula (I) can be prepared, e.g., using a process as illustrated in Schemes 1-7.

Compounds of formula 1-7 can be synthesized as shown in Scheme 1. A selective coupling of the iodide 1-1 with compounds of formula 1-2 [M is B(OR)$_2$, Sn(Alkyl)$_3$, or Zn-Hal] under suitable Suzuki coupling conditions, Stille coupling conditions, or Negishi coupling conditions can give derivatives of formula 1-3. The resulting chloride 1-3 can be converted to its boronic esters or stannanes of formula 1-4 in the presence of a suitable palladium catalyst. Another palladium catalyzed coupling of the resulting compounds of formula 1-4 with a commercially available bromide or iodide building block 1-5 (e.g. Hal is Br or I) under suitable Suzuki or Stille coupling conditions can give compounds of formula 1-6. After removal of Boc on the piperidine under acidic condition (trifluoroacetic acid or hydrochloric acid), the substitution of R$^{14}$ can be introduced to the resulting secondary amine by a reductive amination with the corresponding aldehydes or ketones or an alkylation with the corresponding alkyl halides to provide the desired compounds of formula 1-7.

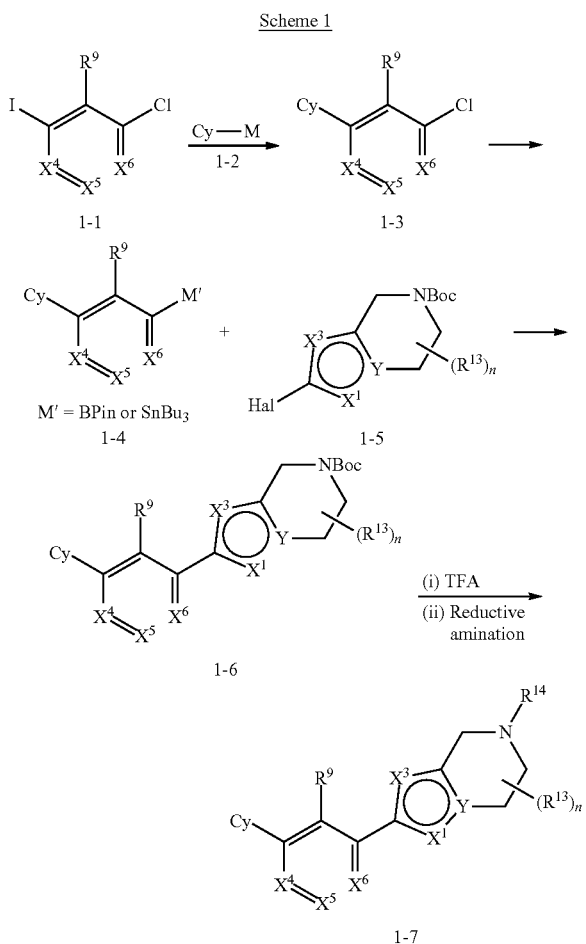

Similarly, compounds of formula 2-4, with C—N bonding between the five- and six-membered aromatic rings, can be synthesized as shown in Scheme 2. Compounds of formula 2-1 (e.g., Hal is Cl or Br) can be prepared using similar conditions as described in Scheme 1. The C—N bond can be formed under suitable Buchwald-Hartwig amination conditions with a commercial amine moiety of formula 2-2 to give compounds of formula 2-3. After removal of Boc on the piperidine under acidic condition, the substitution of $R^{14}$ can be introduced to the resulting secondary amine by a reductive amination with the corresponding aldehydes or ketones to provide the desired compounds of formula 2-4.

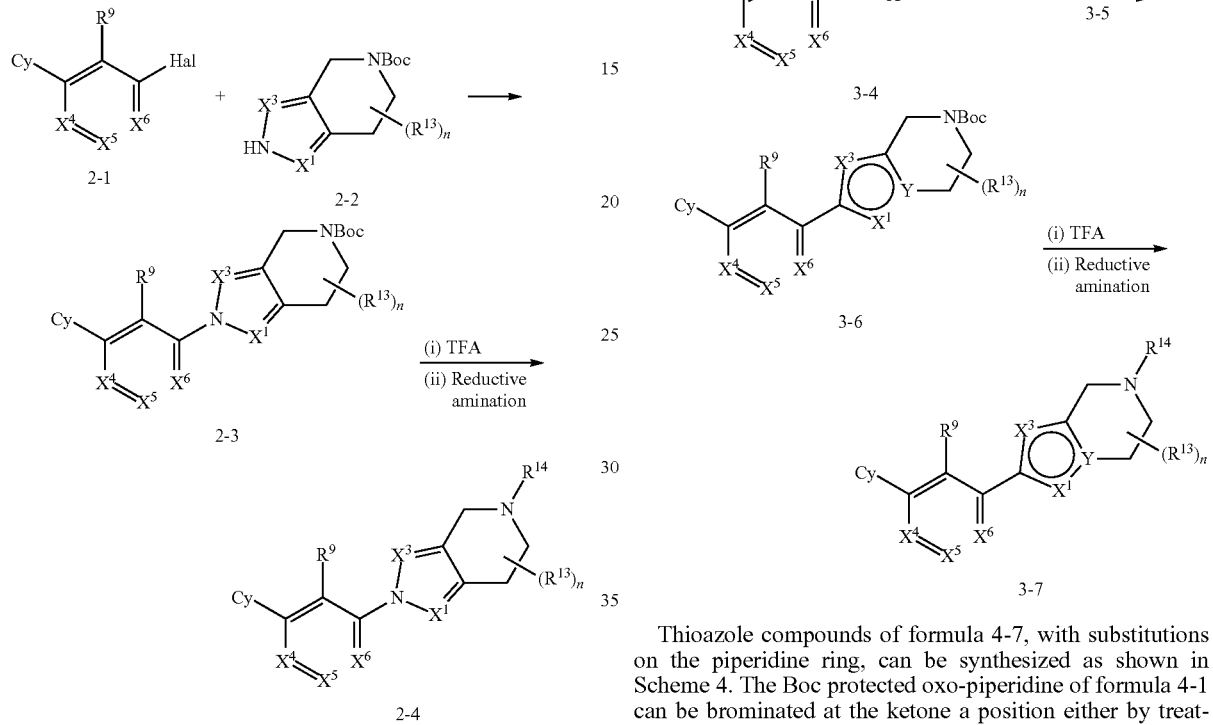

Alternatively, compounds of formula 3-7 can be synthesized as shown in Scheme 3. Selective conversion of the L group in compound 3-1 (L is Br, I or OTf) to boronic ester can be achieved in the presence of a suitable palladium catalyst and bis(pinacolato)diboron to give boronic ester of formula 3-2. Selective Suzuki coupling of heteroaryl bromide 3-3 with boronic ester 3-2 can give biaryl chloride 3-4. Installation of Cy ring can be achieved using similar conditions as described in Scheme 1 by coupling biaryl chloride 3-4 with compound 3-5 to give compounds of formula 3-6. Removal of Boc protecting group followed by reductive amination with the corresponding aldehydes or ketones can provide the desired compounds of formula 3-7.

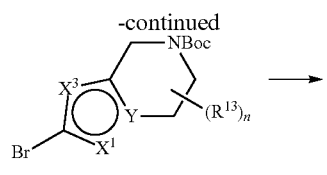

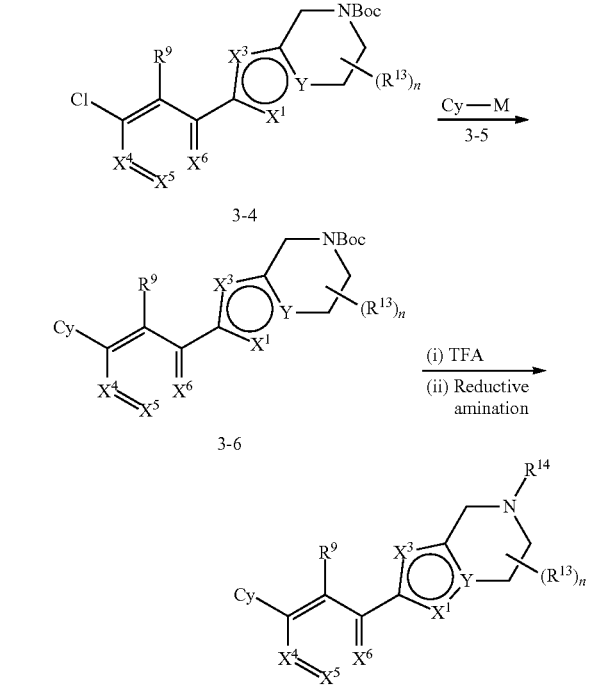

Thioazole compounds of formula 4-7, with substitutions on the piperidine ring, can be synthesized as shown in Scheme 4. The Boc protected oxo-piperidine of formula 4-1 can be brominated at the ketone α position either by treatment with bromine, or by a sequence of TMS enol ether formation and NBS bromination. The resulting bromide 4-2 can be converted to the aminothioazole 4-3 via reacting with thiourea in alcoholic solvents at elevated temperature. The amine group in 4-3 can be converted to halide under Sandermeyer conditions (e.g., in the presence of $^t$BuONO and $CuBr_2$) to give bromothiazole 4-4. Compound of formula 4-5 [M' is $B(OR)_2$ or $SnBu_3$] can be prepared using similar conditions as described in Scheme 1. Coupling of bromothiazole 4-4 with compound 4-5 can be achieved under suitable Suzuki coupling conditions or Stille coupling conditions to give compounds of formula 4-6. After removal of Boc on the coupling product 4-6 under acidic condition (trifluoroacetic acid or hydrochloric acid), the substitution of $R^{14}$ can be introduced to the resulting secondary amine by a reductive amination with the corresponding aldehydes or ketones to provide the desired compounds of formula 4-7.

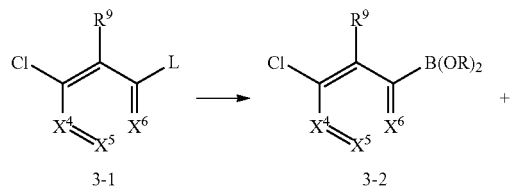

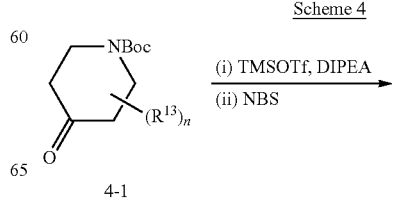

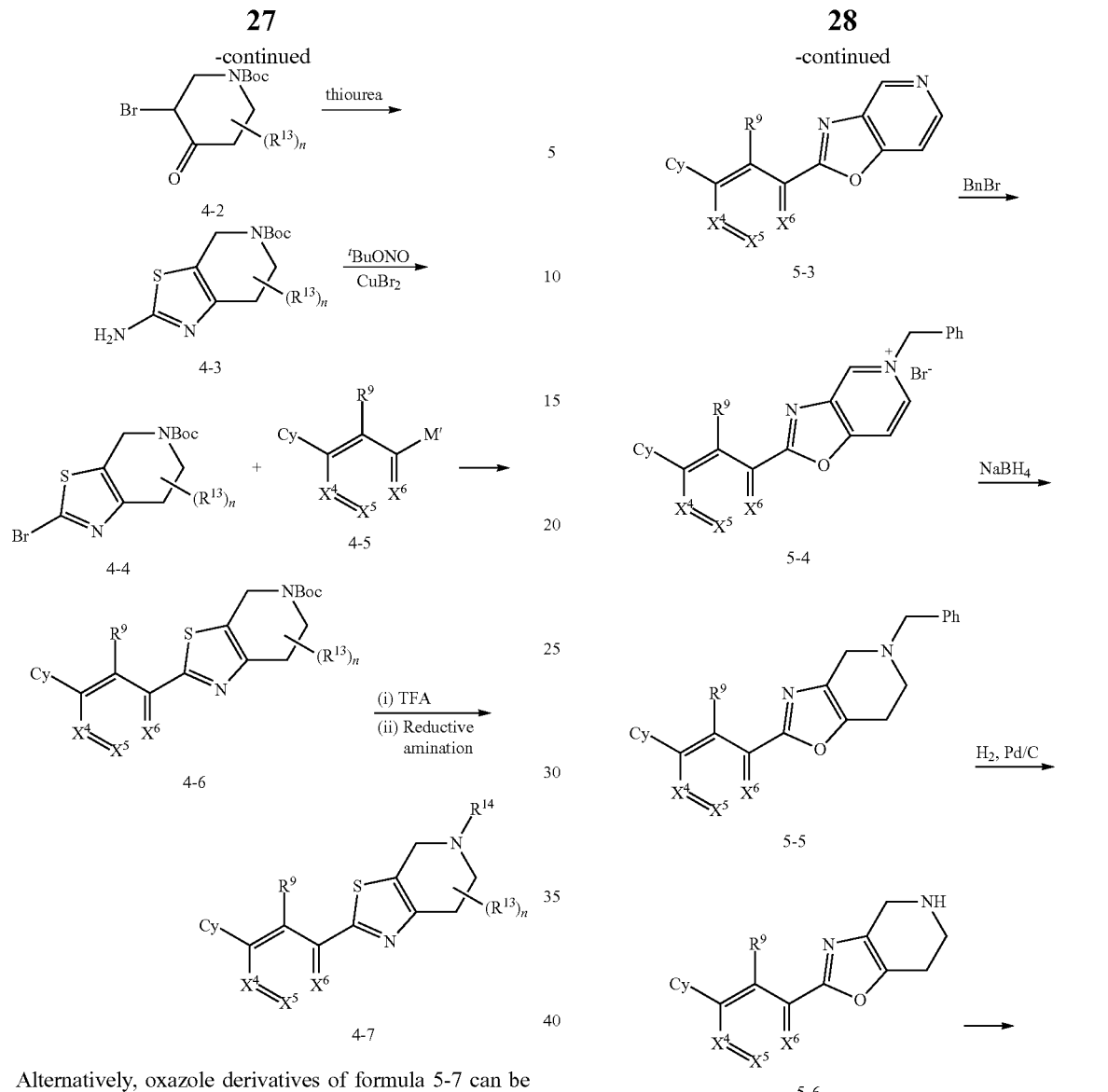

Alternatively, oxazole derivatives of formula 5-7 can be synthesized according to the synthetic route as outlined in Scheme 5. Condensation of carboxylic acid 5-1 with amino, hydroxyl-disubstituted pyridine 5-2 in the presence of a condensation reagent (such as cyanuric chloride) can produce compounds of formula 5-3. Alkylation of the pyridine in 5-3 with benzyl bromide can give the quaternary salt 5-4 and subsequent reduction of 5-4 with NaBH$_4$ can lead to compound 5-5. Removal of the benzyl group using Pd/C under hydrogenation conditions can give compound 5-6. The R$^{14}$ group can be introduced under standard alkylation conditions or reductive amination conditions to give the final product 5-7.

Scheme 5

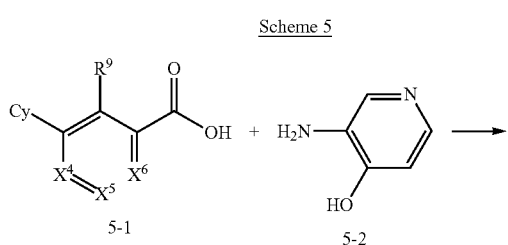

Compounds of formula 6-5 can also be synthesized using conditions as shown in Scheme 6. Cyclization of α-bromo ketone derivatives of formula 6-1 with amino pyrazine 6-2 can give the heteroaryl compounds 6-3. Selective reduction of the pyrazine ring in compound 6-3 can be achieved by treating with LiBH$_4$ or using a similar reaction sequence as described in Scheme 5 to give compound 6-4. Similarly, the R$^{14}$ group can be introduced under alkylation conditions or reductive amination conditions to give the desired product 6-5.

Scheme 6

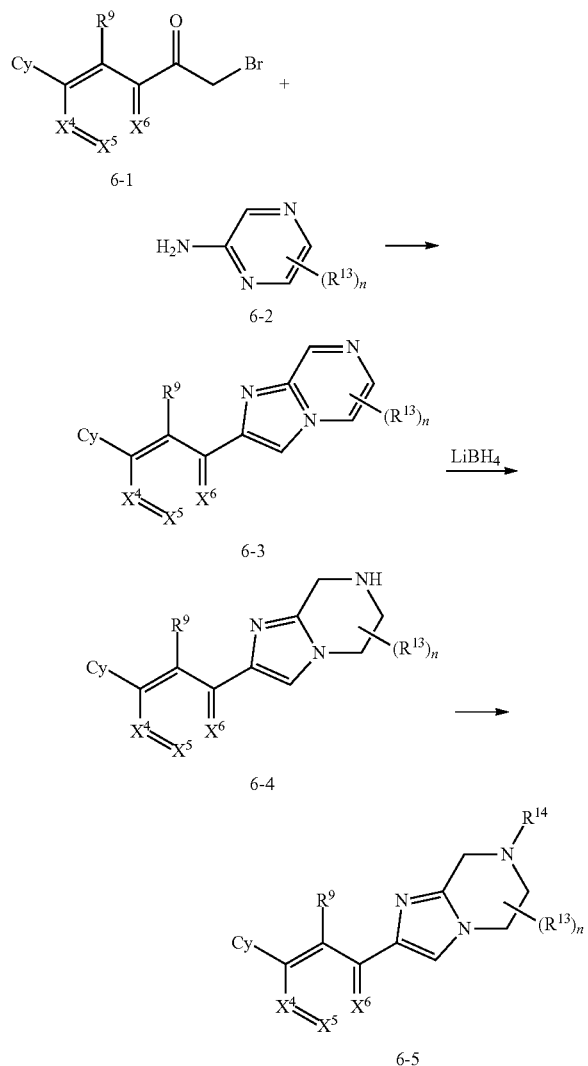

Alternatively, compounds of formula 7-5 can be synthesized as shown in Scheme 7. Coupling of compound 7-1 [M' is B(OR)$_2$ or SnBu$_3$] with heteroaryl halide 7-2 (Hal is Cl, Br or I) can be achieved under suitable Suzuki coupling conditions or Stille coupling conditions to give compounds of formula 7-3. Selective reduction of the heteroaryl ring in 7-3 using similar conditions as described in Scheme 5 or Scheme 6 can give compound 7-4. Installation of R$^{14}$ group can be achieved similarly under alkylation conditions or reductive amination conditions to give compound 7-5.

Scheme 7

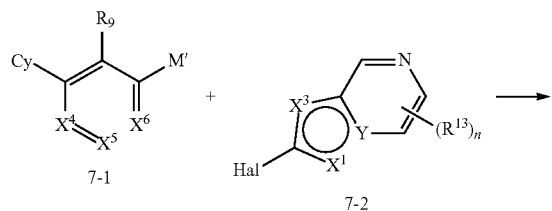

III. Uses of the Compounds

Compounds of the present disclosure can inhibit the activity of PD-1/PD-L1 protein/protein interaction and, thus, are useful in treating diseases and disorders associated with activity of PD-1 and the diseases and disorders associated with PD-L1 including its interaction with other proteins such as PD-1 and B7-1 (CD80). In certain embodiments, the compounds of the present disclosure, or pharmaceutically acceptable salts or stereoisomers thereof, are useful for therapeutic administration to enhance, stimulate and/or increase immunity in cancer or chronic infection, including enhancement of response to vaccination. In some embodiments, the present disclosure provides a method for inhibiting or blocking the PD-1/PD-L1 protein/protein interaction. The method includes administering to an individual or a patient a compound of Formula (I) or any of the formulas as described herein or of a compound as recited in any of the claims and described herein, or a pharmaceutically acceptable salt or a stereoisomer thereof. The compounds of the present disclosure can be used alone, in combination with other agents or therapies or as an adjuvant or neoadjuvant for the treatment of diseases or disorders, including cancer or infection diseases. For the uses described herein, any of the compounds of the disclosure, including any of the embodiments thereof, may be used.

The compounds of the present disclosure inhibit the PD-1/PD-L1 protein/protein interaction, resulting in a PD-1 pathway blockade. The blockade of PD-1 can enhance the immune response to cancerous cells and infectious diseases in mammals, including humans. In some embodiments, the present disclosure provides treatment of an individual or a patient in vivo using a compound of Formula (I) or a salt or stereoisomer thereof such that growth of cancerous tumors is inhibited. A compound of Formula (I) or of any of the formulas as described herein, or a compound as recited in any of the claims and described herein, or a salt or stereoisomer thereof, can be used to inhibit the growth of cancerous tumors. Alternatively, a compound of Formula (I) or of any of the formulas as described herein, or a compound as recited in any of the claims and described herein, or a salt or stereoisomer thereof, can be used in conjunction with other agents or standard cancer treatments, as described below. In one embodiment, the present disclosure provides a method for inhibiting growth of tumor cells in vitro. The method includes contacting the tumor cells in vitro with a compound of Formula (I) or of any of the formulas as described herein, or of a compound as recited in any of the claims and described herein, or of a salt or stereoisomer thereof. In another embodiment, the present disclosure provides a method for inhibiting growth of tumor cells in an individual or a patient. The method includes administering to the individual or patient in need thereof a therapeutically effective amount of a compound of Formula (I) or of any of the formulas as described herein, or of a compound as recited in any of the claims and described herein, or a salt or a stereoisomer thereof.

In some embodiments, provided herein is a method for treating cancer. The method includes administering to a patient in need thereof, a therapeutically effective amount of a compound of Formula (I) or any of the formulas as described herein, a compound as recited in any of the claims and described herein, or a salt thereof. Examples of cancers include those whose growth may be inhibited using compounds of the disclosure and cancers typically responsive to immunotherapy.

In some embodiments, the present disclosure provides a method of enhancing, stimulating and/or increasing the immune response in a patient. The method includes administering to the patient in need thereof a therapeutically effective amount of a compound of Formula (I) or any of the formulas as described herein, a compound as recited in any of the claims and described herein, or a salt thereof.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers, especially metastatic cancers that express PD-L1.

In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

PD-1 pathway blockade with compounds of the present disclosure can also be used for treating infections such as viral, bacteria, fungus and parasite infections. The present disclosure provides a method for treating infections such as viral infections. The method includes administering to a patient in need thereof, a therapeutically effective amount of a compound of Formula (I) or any of the formulas as described herein, a compound as recited in any of the claims and described herein, a salt thereof. Examples of viruses causing infections treatable by methods of the present disclosure include, but are not limit to, human immunodeficiency virus, human papilomavirus, influenza, hepatitis A, B, C or D viruses, adenovirus, poxvirus, herpes simplex viruses, human cytomegalovirus, severe acute respiratory syndrome virus, ebola virus, and measles virus. In some embodiments, viruses causing infections treatable by methods of the present disclosure include, but are not limit to, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

The present disclosure provides a method for treating bacterial infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic bacteria causing infections treatable by methods of the disclosure include chlamydia, rickettsial bacteria, mycobacteria, staphylococci, streptococci, pneumonococci, meningococci and conococci, Klebsiella, Proteus, serratia, *Pseudomonas*, Legionella, diphtheria, salmonella, bacilli, cholera, tetanus, botulism, anthrax, plague, leptospirosis, and Lyme's disease bacteria.

The present disclosure provides a method for treating fungus infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic fungi causing infections treatable by methods of the disclosure include *Candida* (*albicans, krusei, glabrata, tropicalis*, etc.), *Cryptococcus neoformans, Asper-* gillus (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*.

The present disclosure provides a method for treating parasite infections. The method includes administering to a patient in need thereof, a therapeutically effective amount of a compound of Formula (I) or any of the formulas as described herein, a compound as recited in any of the claims and described herein, or a salt thereof. Non-limiting examples of pathogenic parasites causing infections treatable by methods of the disclosure include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors for the treatment of diseases, such as cancer or infections. Examples of cancers include solid tumors and liquid tumors, such as blood cancers. Examples of infections include viral infections, bacterial infections, fungus infections or parasite infections. For example, the compounds of the present disclosure can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf.

In some embodiments, the compounds of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), an IDO inhibitor (e.g., epacadostat and NLG919), an LSD1 inhibitor (e.g., INCB59872 and INCB60003), a TDO inhibitor, a PI3K-delta inhibitor, a PI3K-gamma inhibitor such as PI3K-gamma selective inhibitor (e.g., INCB50797), a Pim inhibitor, a CSFTR inhibitor, a TAM receptor tyrosine kinases (Tyro-3, Axl, and Mer), an angiogenesis inhibitor, an interleukin receptor inhibitor, bromo and extra terminal family members inhibitors (for example, bromodomain inhibitors or BET inhibitors such as INCB54329 and INCB57643) and an adenosine receptor antagonist or combinations thereof.

Compounds of the present disclosure can be used in combination with one or more immune checkpoint inhibitors. Exemplary immune checkpoint inhibitors include inhibitors against immune checkpoint molecules such as CD27, CD28, CD40, CD122, CD96, CD73, CD47, OX40, GITR, CSFIR, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab or pembrolizumab. In some embodiments, the anti-PD1 antibody is pembrolizumab. In some embodiments, the anti PD-1 antibody is SHR-1210.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MED14736, MPDL3280A (also known as RG7446), or MSB0010718C. In some embodiments, the anti-PD-L1 monoclonal antibody is MPDL3280A or MED14736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518 or MK-4166.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562. In some embodiments, the OX40L fusion protein is MED16383.

Compounds of the present disclosure can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, oncolytic virotherapy and immunomodulating small molecules, including thalidomide or JAK/2 inhibitor and the like. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

Other anti-cancer agent(s) include antibody therapeutics such as trastuzumab (Herceptin), antibodies to costimulatory molecules such as CTLA-4 (e.g., ipilimumab), 4-1BB, antibodies to PD-1 and PD-L1, or antibodies to cytokines (IL-10, TGF-β, etc.). Examples of antibodies to PD-1 and/or PD-L1 that can be combined with compounds of the present disclosure for the treatment of cancer or infections such as viral, bacteria, fungus and parasite infections include, but are not limited to, nivolumab, pembrolizumab, MPDL3280A, MEDI-4736 and SHR-1210.

The compounds of the present disclosure can further be used in combination with one or more anti-inflammatory agents, steroids, immunosuppressants or therapeutic antibodies.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, *Giardia*, Malaria, *Leishmania, Staphylococcus aureus, Pseudomonas Aeruginosa*.

Viruses causing infections treatable by methods of the present disclosure include, but are not limit to human papilomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, cornovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, chlamydia, rickettsial bacteria, mycobacteria, staphylococci, streptococci, pneumonococci, meningococci and conococci, *Klebsiella, Proteus, Serratia, Pseudomonas, Legionella*, diphtheria, salmonella, bacilli, cholera, tetanus, botulism, anthrax, plague, leptospirosis, and Lyme's disease bacteria.

Pathogenic fungi causing infections treatable by methods of the disclosure include, but are not limited to, *Candida (albicans, krusei, glabrata, tropicalis*, etc.), *Cryptococcus neoformans, Aspergillus (fumigatus, niger*, etc.), Genus *Mucorales (mucor, absidia, rhizophus), Sporothrix schenkii, Blastomyces dermatitidis, Paracoccidioides brasiliensis, Coccidioides immitis* and *Histoplasma capsulatum*.

Pathogenic parasites causing infections treatable by methods of the disclosure include, but are not limited to, *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

When more than one pharmaceutical agent is administered to a patient, they can be administered simultaneously, separately, sequentially, or in combination (e.g., for more than two agents).

IV. Formulation, Dosage Forms and Administration

When employed as pharmaceuticals, the compounds of the present disclosure can be administered in the form of pharmaceutical compositions. Thus the present disclosure provides a composition comprising a compound of Formula (I) or any of the formulas as described herein, a compound as recited in any of the claims and described herein, or a pharmaceutically acceptable salt thereof, or any of the embodiments thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the present disclosure or a pharmaceutically acceptable salt thereof, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™) In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 g/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

V. Labeled Compounds and Assay Methods

The compounds of the present disclosure can further be useful in investigations of biological processes in normal and abnormal tissues. Thus, another aspect of the present invention relates to labeled compounds of the invention (radio-labeled, fluorescent-labeled, etc.) that would be useful not only in imaging techniques but also in assays, both in vitro and in vivo, for localizing and quantitating PD-1 or PD-L1 protein in tissue samples, including human, and for identifying PD-L1 ligands by inhibition binding of a labeled compound. Accordingly, the present invention includes PD-1/PD-L1 binding assays that contain such labeled compounds.

The present invention further includes isotopically-labeled compounds of the disclosure. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to deuterium, $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$C, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro PD-L1 protein labeling and competition assays, compounds that incorporate $^{3}$H, $^{14}$C, $^{82}$Br, $^{125}$, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is to be understood that a "radio-labeled" or "labeled compound" is a compound that has incorporated at least one radionuclide. In some embodiments the radionuclide is selected from the group consisting of $^{3}$H, $^{14}$C, $^{125}$I, $^{35}$S and $^{82}$Br. In some embodiments, the compound incorporates 1, 2, 3, 4, 5, 6, 7 or 8 deuterium atoms. Synthetic methods for incorporating radio-isotopes into organic compounds are known in the art.

Specifically, a labeled compound of the invention can be used in a screening assay to identify and/or evaluate compounds. For example, a newly synthesized or identified compound (i.e., test compound) which is labeled can be evaluated for its ability to bind a PD-L1 protein by monitoring its concentration variation when contacting with the PD-L1 protein, through tracking of the labeling. For example, a test compound (labeled) can be evaluated for its ability to reduce binding of another compound which is known to bind to a PD-L1 protein (i.e., standard compound). Accordingly, the ability of a test compound to compete with the standard compound for binding to the PD-L1 protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

VI. Kits

The present disclosure also includes pharmaceutical kits useful, e.g., in the treatment or prevention of diseases or disorders associated with the activity of PD-L1 including its interaction with other proteins such as PD-1 and B7-1 (CD80), such as cancer or infections, which include one or more containers containing a pharmaceutical composition comprising a therapeutically effective amount of a compound of Formula (I), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of PD-1/PD-L1 protein/protein interaction according to at least one assay described herein.

EXAMPLES

Experimental procedures for compounds of the invention are provided below. Open Access Preparative LCMS Purification of some of the compounds prepared was performed on Waters mass directed fractionation systems. The basic equipment setup, protocols and control software for the operation of these systems have been described in detail in literature. See, e.g., Blom, "Two-Pump At Column Dilution Configuration for Preparative LC-MS", K. Blom, *J. Combi. Chem.*, 2002, 4, 295-301; Blom et al., "Optimizing Preparative LC-MS Configurations and Methods for Parallel Synthesis Purification", *J. Combi. Chem.*, 2003, 5, 670-83; and Blom et al., "Preparative LC-MS Purification: Improved Compound Specific Method Optimization", *J. Combi. Chem.*, 2004, 6, 874-883.

Example 1

2-(2-methylbiphenyl-3-yl)-4,5,6,7-tetrahydro[1,3]thiazolo[4,5-c]pyridine

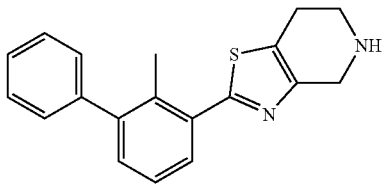

Step 1: 4,4,5,5-tetramethyl-2-(2-methylbiphenyl-3-yl)-1,3,2-dioxaborolane

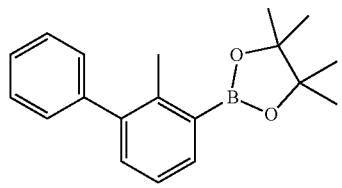 [SMILES: Cc1c(B2OC(C)(C)C(C)(C)O2)cccc1-c1ccccc1]

A mixture of 3-chloro-2-methylbiphenyl (1.44 mL, 8.08 mmol) (Aldrich, cat #361623), 4,4,5,5,4',4',5',5'-octamethyl-[2,2']bi[[1,3,2]dioxaborolanyl] (6.15 g, 24.2 mmol), palladium acetate (72.5 mg, 0.323 mmol), K$_3$PO$_4$ (5.14 g, 24.2 mmol) and 2-(dicyclohexylphosphino)-2',6'-dimethoxy-1,1'-biphenyl (332 mg, 0.808 mmol) in 1,4-dioxane (30 mL) was degassed and stirred at r.t. for 48 h. The reaction mixture was diluted with methylene chloride, washed with saturated NaHCO$_3$, water and brine. The organic layer was dried over Na$_2$SO$_4$, filtered and concentrated. The residue was purified by flash chromatography on a silica gel column eluting with 0 to 5% ethyl acetate in methylene chloride to give the desired product (1.60 g, 68%). LCMS calculated for C$_{19}$H$_{24}$BO$_2$ (M+H)$^+$: m/z=295.2; found 295.1.

Step 2: tert-butyl 2-(2-methylbiphenyl-3-yl)-6,7-dihydro[1,3]thiazolo[4,5-c]pyridine-5(4H)-carboxylate

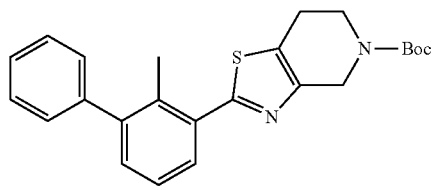 [SMILES: Cc1c(-c2ccccc2)cccc1-c1nc2c(s1)CCN(C(=O)OC(C)(C)C)C2]

To a solution of tert-butyl 2-bromo-6,7-dihydro[1,3]thiazolo[4,5-c]pyridine-5(4H)-carboxylate (9.9 mg, 31 μmol) (Astatech, cat #27671), 4,4,5,5-tetramethyl-2-(2-methylbiphenyl-3-yl)-1,3,2-dioxaborolane (10 mg, 34 μmol) and sodium carbonate (8.2 mg, 77.2 μmol) in tert-butyl alcohol (0.3 mL) and water (0.1 mL) was added dichloro[1,1'-bis(dicyclohexylphosphino)ferrocene]palladium(II) (Pd-127: 4.7 mg, 6.2 μmol). The mixture was purged with N$_2$, then heated at 110° C. for 2 h. The reaction mixture was diluted with methylene chloride, washed with saturated NaHCO$_3$, water and brine. The organic layer was dried over Na$_2$SO$_4$, filtered and concentrated. The residue was used in the next step without further purification. LC-MS calculated for C$_{24}$H$_{27}$N$_2$O$_2$S (M+H)$^+$: m/z=407.2; found 407.2.

Step 3: 2-(2-methylbiphenyl-3-yl)-4,5,6,7-tetrahydro[1,3]thiazolo[4,5-c]pyridine The crude product from Step 2 was dissolved in methylene chloride (0.6 mL) then treated with TFA (0.3 mL). The resulting mixture was stirred at room temperature for 30 min before concentrated and purified by prep-HPLC (pH=2, acetonitrile/water+TFA) to give the desired product as the TFA salt. LC-MS calculated for C$_{19}$H$_{19}$N$_2$S (M+H)$^+$: m/z=307.2; found 307.2.

Example 2

2-(2-methylbiphenyl-3-yl)-4,5,6,7-tetrahydro[1,3]thiazolo[5,4-c]pyridine

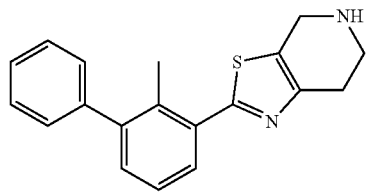 [SMILES: Cc1c(-c2ccccc2)cccc1-c1nc2c(s1)CNCC2]

Step 1: tert-butyl 2-(2-methylbiphenyl-3-yl)-6,7-dihydro[, 3]thiazolo[5,4-c]pyridine-5(4H)-carboxylate

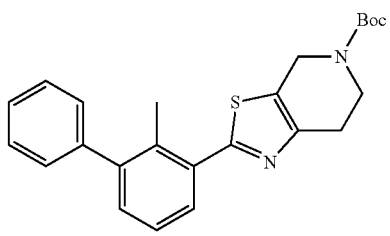 [SMILES: Cc1c(-c2ccccc2)cccc1-c1nc2c(s1)CN(C(=O)OC(C)(C)C)CC2]

This compound was prepared using similar procedures as described for Example 1, Step 2 with tert-butyl 2-bromo-6,7-dihydro[1,3]thiazolo[5,4-c]pyridine-5(4H)-carboxylate (Astatech, cat #AB1021) replacing tert-butyl 2-bromo-6,7-dihydro[1,3]thiazolo[4,5-c]pyridine-5(4H)-carboxylate. The reaction mixture was diluted with methylene chloride, washed with saturated NaHCO$_3$, water and brine. The organic layer was dried over Na$_2$SO$_4$, filtered and concentrated. The residue was used in the next step without further purification. LC-MS calculated for $C_{24}H_{27}N_2O_2S$ (M+H)$^+$: m/z=407.2; found 407.2.

Step 2: 2-(2-methylbiphenyl-3-yl)-4,5,6,7-tetrahydro[, 3]thiazolo[5,4-c]pyridine The crude product from Step 1 was dissolved in methylene chloride (0.6 mL) then treated with TFA (0.3 mL). The resulting mixture was stirred at room temperature for 30 min before concentrated and purified by prep-HPLC (pH=2, acetonitrile/water+TFA) to give the desired product as the TFA salt. LC-MS calculated for $C_{19}H_9N_2S$ (M+H)$^+$: m/z=307.2; found 307.2.

Example 3

5-methyl-2-(2-methylbiphenyl-3-yl)-4,5,6,7-tetrahydro[1,3]thiazolo[5,4-c]pyridine

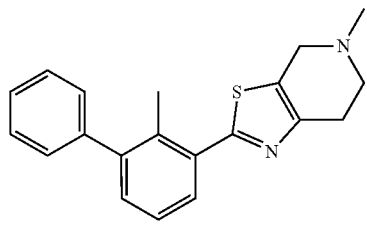 [SMILES: Cc1c(-c2ccccc2)cccc1-c1nc2c(s1)CN(C)CC2]

Formaldehyde (37 wt. % in water, 16 µL, 0.2 mmol) was added to a solution of 2-(2-methylbiphenyl-3-yl)-4,5,6,7-tetrahydro[1,3]thiazolo[5,4-c]pyridine (Example 2: 15 mg, 0.049 mmol) and N,N-diisopropylethylamine (20 µL, 0.1 mmol) in methylene chloride (1.0 mL), then the reaction mixture was allowed to stir at r.t. for 5 min before sodium triacetoxyborohydride (30 mg, 0.1 mmol) was added to the reaction mixture. The resulting mixture was stirred for another 2 h then concentrated and purified by prep-HPLC (pH=2, acetonitrile/water+TFA) to give the desired product as the TFA salt. LC-MS calculated for $C_{20}H_{21}N_2S$ (M+H)$^+$: m/z=321.2; found 321.2.

Example 4

2-[2-(2-methylbiphenyl-3-yl)-6,7-dihydro[1,3]thiazolo[5,4-c]pyridin-5(4H)-yl]ethanol

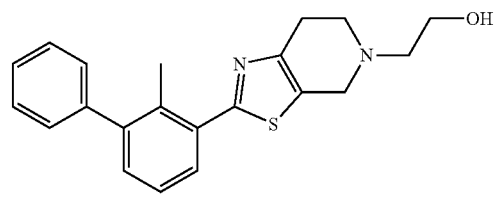 [SMILES: Cc1c(-c2ccccc2)cccc1-c1nc2c(s1)CN(CCO)CC2]

To a solution of 2-(2-methylbiphenyl-3-yl)-4,5,6,7-tetrahydro[1,3]thiazolo[5,4-c]pyridine (Example 2: 5.0 mg, 16 µmol) and bromoethanol (5.7 µL, 80 µmol) in N,N-dimethylformamide (0.5 mL) was added potassium carbonate (11 mg, 80 µmol). The resulting mixture was stirred at r.t. for 16 h, and then purified by prep-HPLC (pH=2, acetonitrile/water+TFA) to give the desired product as the TFA salt. LC-MS calculated for $C_{21}H_{23}N_2OS$ (M+H)$^+$: m/z=351.2; found 351.2.

Example 5

(2S)-1-[2-(2-methylbiphenyl-3-yl)-6,7-dihydro[1,3]thiazolo[5,4-c]pyridin-5(4H)-yl]propan-2-ol

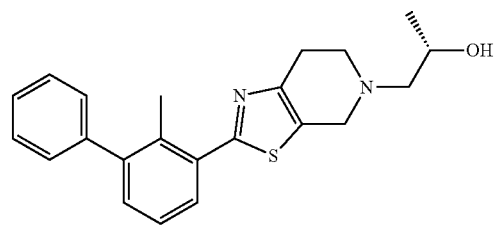 [SMILES: Cc1c(-c2ccccc2)cccc1-c1nc2c(s1)CN(C[C@H](C)O)CC2]

To a solution of 2-(2-methylbiphenyl-3-yl)-4,5,6,7-tetrahydro[1,3]thiazolo[5,4-c]pyridine (Example 2: 10.0 mg, 32.6 µmol) and N,N-diisopropylethylamine (11.4 µL, 0.653 mmol) in methanol (1.3 mL) was added (S)-(−)-methyloxirane (TCI, Cat #: P0951: 22.9 µL, 0.326 mmol). The reaction mixture was stirred at r.t. for 12 h, then diluted with methanol then purified by prep-HPLC (pH=2, acetonitrile/water+TFA) to give the desired product as the TFA salt. LC-MS calculated for $C_{22}H_{25}N_2OS$ (M+H)$^+$: m/z=365.2; found 365.2.

Example 6

2-(2-methylbiphenyl-3-yl)-5-(tetrahydro-2H-pyran-4-yl)-4,5,6,7-tetrahydro[1,3]thiazolo[5,4-c]pyridine

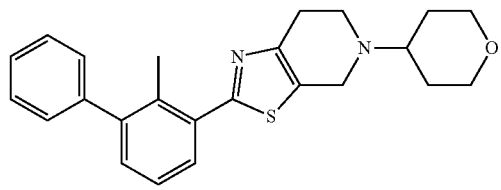 [SMILES: Cc1c(-c2ccccc2)cccc1-c1nc2c(s1)CN(C1CCOCC1)CC2]

This compound was prepared using similar procedures as described for Example 3 with tetrahydro-4H-pyran-4-one (Aldrich, Cat #198242) replacing formaldehyde. The resulting mixture was purified by prep-HPLC (pH=2, acetonitrile/water+TFA) to give the desired product as the TFA salt. LC-MS calculated for $C_{24}H_{27}N_2OS$ (M+H)$^+$: m/z=391.2; found 391.2.

Example 7

4-[2-(2-methylbiphenyl-3-yl)-6,7-dihydro[1,3]thiazolo[5,4-c]pyridin-5(4H)-yl]cyclohexanecarboxylic acid

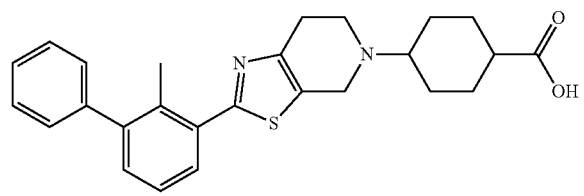 [SMILES: Cc1c(-c2ccccc2)cccc1-c1nc2c(s1)CN(C1CCC(C(=O)O)CC1)CC2]

This compound was prepared using similar procedures as described for Example 3 with 4-oxocyclohexanecarboxylic acid (Aldrich, Cat #751294) replacing formaldehyde. The resulting mixture was purified by prep-HPLC (pH=2, acetonitrile/water+TFA) to give the desired product as the TFA salt. LC-MS calculated for $C_{26}H_{29}N_2O_2S$ (M+H)$^+$: m/z=433.2; found 433.2.

Example 8

4-[2-(2-methylbiphenyl-3-yl)-6,7-dihydro[1,3]thiazolo[5,4-c]pyridin-5(4H)-yl]butanoic acid

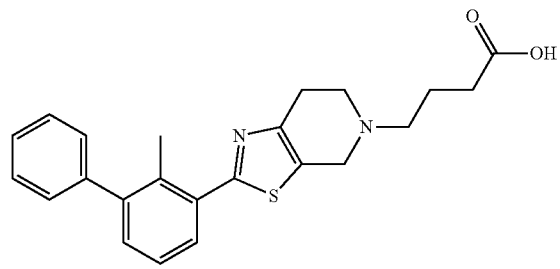 [SMILES: Cc1c(-c2ccccc2)cccc1-c1nc2c(s1)CN(CCCC(=O)O)CC2]

This compound was prepared using similar procedures as described for Example 3 with 4-oxobutanoic acid (Aldrich, Cat #14075) replacing formaldehyde. The resulting mixture was purified by prep-HPLC (pH=2, acetonitrile/water+TFA) to give the desired product as the TFA salt. LC-MS calculated for $C_{23}H_{25}N_2O_2S$ (M+H)$^+$: m/z=393.2; found 393.2.

Example 9

Trans-2-{[2-(2-methylbiphenyl-3-yl)-6,7-dihydro[1,3]thiazolo[5,4-c]pyridin-5(4H)-yl]methyl}cyclopropanecarboxylic acid

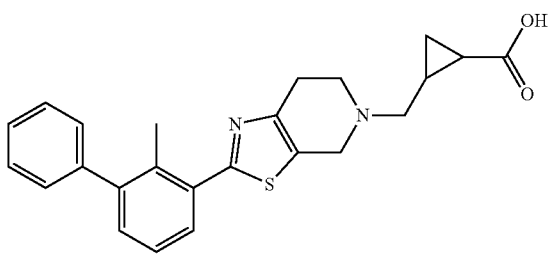 [SMILES: Cc1c(-c2ccccc2)cccc1-c1nc2c(s1)CN(CC1CC1C(=O)O)CC2]

Step 1: ethyl trans-2-{[2-(2-methylbiphenyl-3-yl)-6,7-dihydro[1,3]thiazolo[5,4-c]pyridin-5(4H)-yl]methyl}cyclopropanecarboxylate

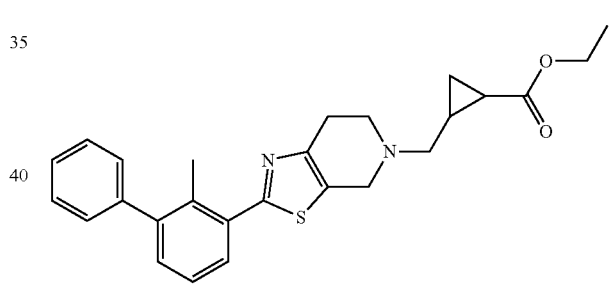

This compound was prepared using similar procedures as described for Example 3 with trans-ethyl 2-formylcyclopropanecarboxylate (Aldrich, Cat #157279) replacing formaldehyde. The resulting mixture was concentrated to dryness and used in the next step without further purification. LC-MS calculated for $C_{26}H_{29}N_2O_2S$ (M+H)$^+$: m/z=433.2; found 433.2.

Step 2: trans-2-{[2-(2-methylbiphenyl-3-yl)-6,7-dihydro[, 3]thiazolo[5,4-c]pyridin-5(4H)-yl]methyl}cyclopropanecarboxylic acid The crude product in Step 1 was treated with 1 N aq. NaOH (0.5 mL) in methanol (1.0 mL) at 50° C. and stirred for 15 h. The reaction mixture was cooled to room temperature then purified by prep-HPLC (pH=2, acetonitrile/water+TFA) to give the desired product as the TFA salt. LC-MS calculated for $C_{24}H_{25}N_2O_2S$ (M+H)$^+$: m/z=405.2; found 405.2.

Example 10

2-(2-methylbiphenyl-3-yl)-5-(1H-pyrazol-4-ylmethyl)-4,5,6,7-tetrahydro[1,3]thiazolo[5,4-c]pyridine

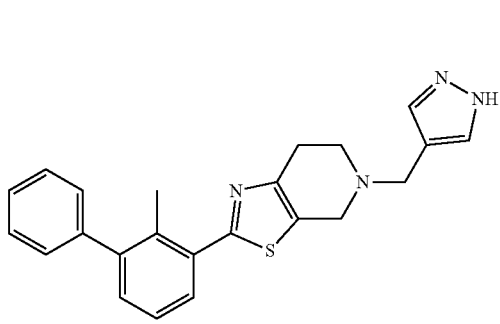 [SMILES: Cc1c(-c2ccccc2)cccc1-c1nc2c(s1)CN(Cc1cn[nH]c1)CC2]

This compound was prepared using similar procedures as described for Example 3 with 1H-pyrazole-4-carbaldehyde (ArkPharm, Cat #AK-25836) replacing formaldehyde. The resulting mixture was purified by prep-HPLC (pH=2, acetonitrile/water+TFA) to give the desired product as the TFA salt. LC-MS calculated for $C_{23}H_{23}N_4S$ $(M+H)^+$: m/z=387.2; found 387.2.

Example 11

{4-[2-(2-methylbiphenyl-3-yl)-6,7-dihydro[1,3]thiazolo[5,4-c]pyridin-5(4H)-yl]cyclohexyl}acetonitrile

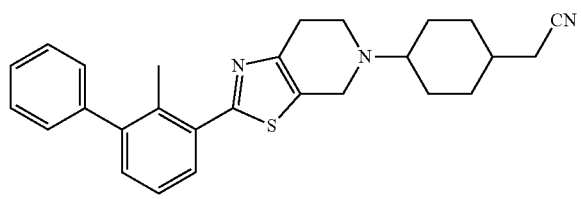 [SMILES: Cc1c(-c2ccccc2)cccc1-c1nc2c(s1)CN(C1CCC(CC#N)CC1)CC2]

This compound was prepared using similar procedures as described for Example 3 with (4-oxocyclohexyl)acetonitrile (ArkPharm, Cat #AK-46872) replacing formaldehyde. The resulting mixture was purified by prep-HPLC (pH=2, acetonitrile/water+TFA) to give the desired product as the TFA salt. LC-MS calculated for $C_{27}H_{30}N_3S$ $(M+H)^+$: m/z=428.2; found 428.2.

Example 12

2-(2-methylbiphenyl-3-yl)-4,5,6,7-tetrahydropyrazolo[1,5-a]pyrazine

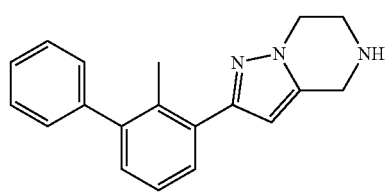 [SMILES: Cc1c(-c2ccccc2)cccc1-c1cc2n(n1)CCNC2]

Step 1: tert-butyl 2-(2-methylbiphenyl-3-yl)-6,7-dihydropyrazolo[1,5-a]pyrazine-5(4H)-carboxylate

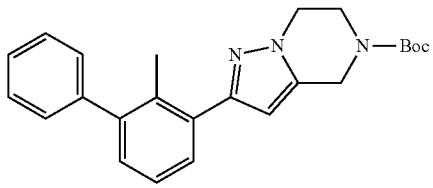 [SMILES: Cc1c(-c2ccccc2)cccc1-c1cc2n(n1)CCN(C(=O)OC(C)(C)C)C2]

This compound was prepared using similar procedures as described for Example 1, Step 2 with tert-butyl 2-iodo-6,7-dihydropyrazolo[1,5-a]pyrazine-5(4H)-carboxylate (Aurum Pharmatech, cat #10451833) replacing tert-butyl 2-bromo-6,7-dihydro[1,3]thiazolo[4,5-c]pyridine-5(4H)-carboxylate. The reaction mixture was diluted with methylene chloride, washed with saturated $NaHCO_3$, water and brine. The organic layer was dried over $Na_2SO_4$, filtered and concentrated. The residue was used in the next step without further purification. LC-MS calculated for $C_{24}H_{28}N_3O_2$ $(M+H)^+$: m/z=390.2; found 390.2.

Step 2: 2-(2-methylbiphenyl-3-yl)-4,5,6,7-tetrahydropyrazolo[1,5-a]pyrazine

The crude product from Step 1 was dissolved in methylene chloride (0.6 mL) then treated with TFA (0.3 mL). The resulting mixture was stirred at room temperature for 30 min before concentrated and purified by prep-HPLC (pH=2, acetonitrile/water+TFA) to give the desired product as the TFA salt. LC-MS calculated for $C_{19}H_2N_3$ $(M+H)^+$: m/z=290.2; found 290.2.

Example 13

2-(2,3-dihydro-1,4-benzodioxin-6-yl)-6-(4,5,6,7-tetrahydro[1,3]thiazolo[5,4-c]pyridin-2-yl)benzonitrile

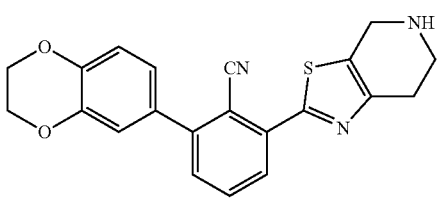 [SMILES: N#Cc1c(-c2ccc3c(c2)OCCO3)cccc1-c1nc2c(s1)CNCC2]

Step 1: 2-bromo-6-(2,3-dihydro-1,4-benzodioxin-6-yl)benzonitrile

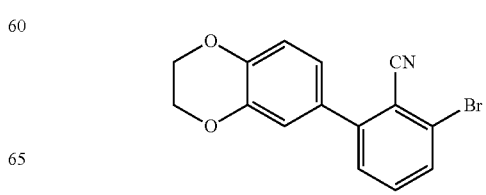

To a solution of 2-bromo-6-iodobenzonitrile (207 mg, 0.674 mmol) (Astatech, cat #CL8155), 2,3-dihydro-1,4-benzodioxin-6-ylboronic acid (127 mg, 0.707 mmol) (Aldrich, cat #635995) and sodium carbonate (178 mg, 1.68 mmol) in tert-butyl alcohol (3 mL) and water (1 mL) was added Pd-127 (51 mg, 67 µmol). The reaction mixture was purged with N$_2$, and then heated at 90° C. for 2 h. The reaction mixture was diluted with methylene chloride, washed with saturated NaHCO$_3$, water and brine. The organic layer was dried over Na$_2$SO$_4$, filtered and concentrated. The residue was purified by flash chromatography on a silica gel column eluting with 10 to 20% ethyl acetate in hexanes to give the desired product (130 mg, 61%). LCMS calculated for C$_{15}$H$_{11}$BrNO$_2$ (M+H)$^+$: m/z=316.2; found 316.2.

Step 2: 2-(2,3-dihydro-1,4-benzodioxin-6-yl)-6-(4,4, 5,5-tetramethyl-1,3,2-dioxaborolan-2-yl)benzonitrile

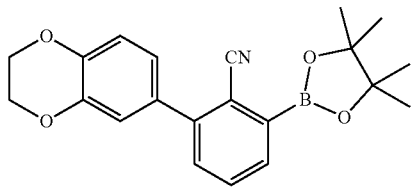 [SMILES: CC1(C)OB(c2cccc(-c3ccc4c(c3)OCCO4)c2C#N)OC1(C)C]

A mixture of 4,4,5,5,4',4',5',5'-octamethyl-[2,2']bi[[1,3,2] dioxaborolanyl] (106 mg, 0.418 mmol), 2-bromo-6-(2,3-dihydro-1,4-benzodioxin-6-yl)benzonitrile (120 mg, 0.380 mmol), [1,1'-bis(diphenylphosphino)ferrocene]dichloropalladium(II), complex with dichloromethane (1:1) (20 mg, 20 µmol) and potassium acetate (112 mg, 1.14 mmol) in 1,4-dioxane (3 mL) was purges with nitrogen and heated at 90° C. for 16 h. The reaction mixture was diluted with methylene chloride, washed with saturated NaHCO$_3$, water and brine. The organic layer was dried over Na$_2$SO$_4$, filtered and concentrated. The residue was purified by flash chromatography on a silica gel column eluting with 0 to 50% ethyl acetate in hexanes to give the desired product (70 mg, 51%). LCMS calculated for C$_{21}$H$_{23}$BNO$_4$ (M+H)$^+$: m/z=364.2; found 364.2.

Step 3: tert-butyl 2-[2-cyano-3-(2,3-dihydro-1,4-benzodioxin-6-yl)phenyl]-6,7-dihydro[1,3]thiazolo [5,4-c]pyridine-5(4H)-carboxylate

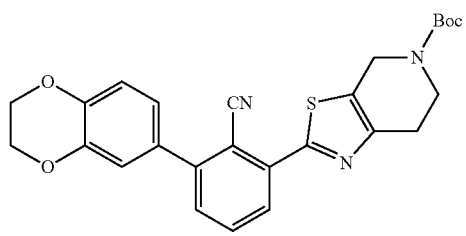 [SMILES: CC(C)(C)OC(=O)N1CCc2nc(-c3cccc(-c4ccc5c(c4)OCCO5)c3C#N)sc2C1]

This compound was prepared using similar procedures as described for Example 2, Step 1 with 2-(2,3-dihydro-1,4-benzodioxin-6-yl)-6-(4,4,5,5-tetramethyl-1,3,2-dioxaborolan-2-yl)benzonitrile (Step 2) replacing 4,4,5,5-tetramethyl-2-(2-methylbiphenyl-3-yl)-1,3,2-dioxaborolane. The reaction mixture was diluted with methylene chloride, washed with saturated NaHCO$_3$, water and brine. The organic layer was dried over Na$_2$SO$_4$, filtered and concentrated. The residue was used in the next step without further purification. LC-MS calculated for C$_{26}$H$_{26}$N$_3$O$_4$S (M+H)$^+$: m/z=476.2; found 476.2.

Step 4: 2-(2,3-dihydro-1,4-benzodioxin-6-yl)-6-(4,5, 6,7-tetrahydro[, 3]thiazolo[5,4-c]pyridin-2-yl)benzonitrile The crude product from Step 3 was dissolved in methylene chloride (0.6 mL) then treated with TFA (0.3 mL). The resulting mixture was stirred at room temperature for 30 min before concentrated and purified by prep-HPLC (pH=2, acetonitrile/water+TFA) to give the desired product as the TFA salt. LC-MS calculated for C$_{21}$H$_{18}$N$_3$O$_2$S (M+H)$^+$: m/z=376.2; found 376.2.

Example 14

2-(3-methyl-4-phenylpyridin-2-yl)-4,5,6,7-tetrahydro[1,3]thiazolo[5,4-c]pyridine

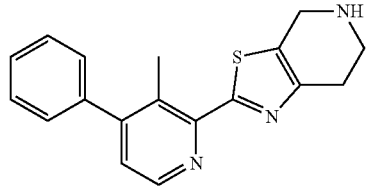

Step 1: 2-chloro-3-methyl-4-phenylpyridine

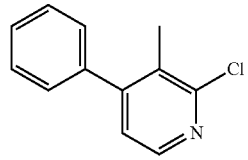

To a solution of 2-chloro-4-iodo-3-methylpyridine (303 mg, 1.20 mmol) (Aldrich, cat #724092), phenylboronic acid (160 mg, 1.32 mmol) (Aldrich, cat #78181) and sodium carbonate (317 mg, 2.99 mmol) in tert-butyl alcohol (10 mL) and water (6 mL) was added Pd-127 (181 mg, 0.239 mmol). The resulting mixture was purged with N$_2$, and then heated at 80° C. for 2 h. The reaction mixture was diluted with methylene chloride, washed with saturated NaHCO$_3$, water and brine. The organic layer was dried over Na$_2$SO$_4$, filtered and concentrated. The residue was purified by flash chromatography on a silica gel column eluting with 10 to 20% ethyl acetate in hexanes to give the desired product (225 mg, 92%). LCMS calculated for C$_{12}$H$_{11}$ClN (M+H)$^+$: m/z=204.2; found 204.2.

Step 2: tert-butyl 2-(3-methyl-4-phenylpyridin-2-yl)-6,7-dihydro[1,3]thiazolo[5,4-c]pyridine-5(4H)-carboxylate

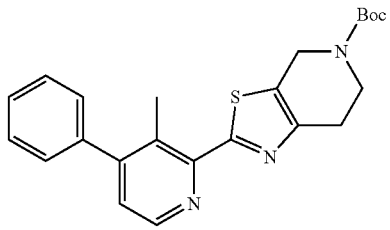 [SMILES: Cc1c(-c2ccccc2)ccnc1-c1nc2c(s1)CN(C(=O)OC(C)(C)C)CC2]

A solution of 2-chloro-3-methyl-4-phenylpyridine (40.0 mg, 0.196 mmol) in 1,4-dioxane (2.0 mL) was bubbled with N$_2$, then hexabutyldistannane (129 µL, 0.255 mmol), lithium chloride (51.6 mg, 1.22 mmol), dichloro[bis(triphenylphosphoranyl)]palladium (14 mg, 20 µmol) and tetrakis(triphenylphosphine)palladium(O) (23 mg, 20 µmol) were added in sequence. The resulting mixture was heated at 90° C. for 90 min before a solution of tert-butyl 2-bromo-6,7-dihydro[1,3]thiazolo[5,4-c]pyridine-5(4H)-carboxylate (94.0 mg, 0.294 mmol) in 1,4-dioxane (1.5 mL) was pumped in over 1.5 h at 95° C. The resulted mixture was stirred at the same temperature for another 12 h, then cooled to room temperature, diluted with methylene chloride, washed with saturated NaHCO$_3$, water and brine. The organic layer was dried over Na$_2$SO$_4$, filtered and concentrated. The residue was used in the next step without further purification. LC-MS calculated for C$_{23}$H$_{26}$N$_3$O$_2$S (M+H)$^+$: m/z=408.2; found 408.2.

Step 3: 2-(3-methyl-4-phenylpyridin-2-yl)-4,5,6,7-tetrahydro[1,3]thiazolo[5,4-c]pyridine The crude product from Step 2 was dissolved in methylene chloride (0.6 mL) then treated with TFA (0.3 mL). The resulting mixture was stirred at room temperature for 30 min before concentrated and purified by prep-HPLC (pH=2, acetonitrile/water+TFA) to give the desired product as the TFA salt. LC-MS calculated for C$_{18}$H$_{18}$N$_3$S (M+H)$^+$: m/z=308.2; found 308.2. $^1$H NMR (600 MHz, DMSO) δ 9.35 (s, 1H), 8.56-8.50 (m, 1H), 7.55-7.51 (m, 2H), 7.50-7.46 (m, 1H), 7.44-7.40 (m, 2H), 7.34 (d, J=4.8 Hz, 1H), 4.52 (br, 2H), 3.54 (br, 2H), 3.09 (t, J=6.1 Hz, 2H), 2.62 (s, 3H).

Example 15

2-[4-(3-methoxyphenyl)-3-methylpyridin-2-yl]-4,5,6,7-tetrahydro[1,3]thiazolo[5,4-c]pyridine

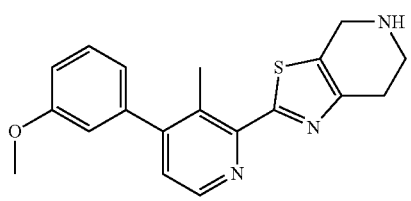 [SMILES: COc1cccc(-c2ccnc(-c3nc4c(s3)CNCC4)c2C)c1]

This compound was prepared using similar procedures as described for Example 14, Step 1-3 with 3-methoxyphenyl-boronic acid (Aldrich, cat 441686) replacing phenylboronic acid in Step 1. The reaction mixture was purified by prep-HPLC (pH=2, acetonitrile/water+TFA) to give the desired product as the TFA salt. LC-MS calculated for C$_{19}$H$_{20}$N$_3$OS (M+H)$^+$: m/z=338.2; found 338.2.

Example 16

2-[4-(2,3-dihydro-1,4-benzodioxin-6-yl)-3-methylpyridin-2-yl]-4,5,6,7-tetrahydro[1,3]thiazolo[5,4-c]pyridine

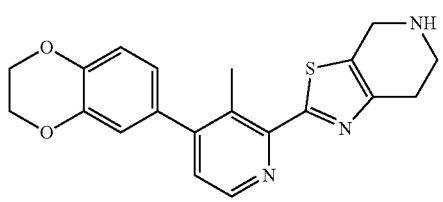 [SMILES: Cc1c(-c2ccc3c(c2)OCCO3)ccnc1-c1nc2c(s1)CNCC2]

This compound was prepared using similar procedures as described for Example 14, Step 1-3 with 2,3-dihydro-1,4-benzodioxin-6-ylboronic acid (Combi-blocks, cat #BB-8311) replacing phenylboronic acid in Step 1. The reaction mixture was purified by prep-HPLC (pH=2, acetonitrile/water+TFA) to give the desired product as the TFA salt. LC-MS calculated for C$_{20}$H$_{20}$N$_3$O$_2$S (M+H)$^+$: m/z=366.2; found 366.2.

Example 17

2-(2-methylbiphenyl-3-yl)-4,5,6,7-tetrahydro-2H-pyrazolo[4,3-c]pyridine

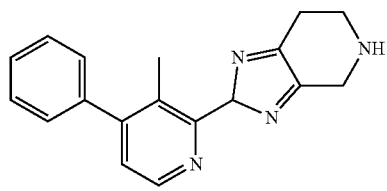 [SMILES: Cc1c(-c2ccccc2)ccnc1C1N=C2CCNCC2=N1]

Step 1: 3-bromo-2-methylbiphenyl

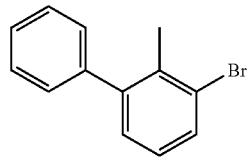

This compound was prepared using similar procedures as described for Example 13, Step 1 with 1-bromo-3-iodo-2-methylbenzene (Oakwood, cat #037475) replacing 2-bromo-6-iodobenzonitrile, and phenylboronic acid replacing 2,3-dihydro-1,4-benzodioxin-6-ylboronic acid. The reaction mixture was diluted with methylene chloride, washed with saturated NaHCO$_3$, water and brine. The organic layer was dried over Na$_2$SO$_4$, filtered and concentrated. The residue was purified by flash chromatography on a silica gel column eluting with 0 to 5% ethyl acetate in hexanes to give the desired product.

Step 2: tert-butyl 2-(2-methylbiphenyl-3-yl)-2,4,6,7-tetrahydro-5H-pyrazolo[4,3-c]pyridine-5-carboxylate

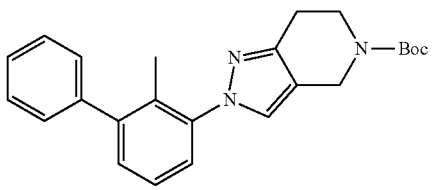 [SMILES: Cc1c(-c2ccccc2)cccc1-n1cc2c(n1)CCN(C(=O)OC(C)(C)C)C2]

To a mixture of 3-bromo-2-methylbiphenyl (100 mg, 0.405 mmol), tert-butyl 1,4,6,7-tetrahydro-5H-pyrazolo[4,3-c]pyridine-5-carboxylate (ArkPharm, Cat #AK-24984: 180 mg, 0.81 mmol), (2'-aminobiphenyl-2-yl)(chloro)[dicyclohexyl(2',6'-diisopropoxybiphenyl-2-yl)phosphoranyl]palladium (30.9 mg, 39.7 µmol) (RuPhos G2, Aldrich, cat #753246) in 1,4-dioxane (1.1 mL) was added sodium tert-butoxide (76.4 mg, 0.795 mmol). The resulting mixture was heated at 110° C. under the atmosphere of $N_2$ for 15 h, then diluted with methylene chloride, washed with saturated NaHCO$_3$, water and brine. The organic layer was dried over Na$_2$SO$_4$, filtered and concentrated. The residue was used in the next step without further purification. LC-MS calculated for $C_{24}H_{28}N_3O_2$ (M+H)$^+$: m/z=390.2; found 390.2.

Step 3: 2-(2-methylbiphenyl-3-yl)-4,5,6,7-tetrahydro-2H-pyrazolo[4,3-c]pyridine

The crude product from Step 2 was dissolved in methylene chloride (0.6 mL) then treated with TFA (0.3 mL). The resulting mixture was stirred at room temperature for 30 min before concentrated and purified by prep-HPLC (pH=2, acetonitrile/water+TFA) to give the desired product as the TFA salt. LC-MS calculated for $C_{19}H_{20}N_3$ (M+H)$^+$: m/z=290.2; found 290.2.

Example 18

2-(2-methylbiphenyl-3-yl)-4,5,6,7-tetrahydro-2H-pyrazolo[3,4-c]pyridine

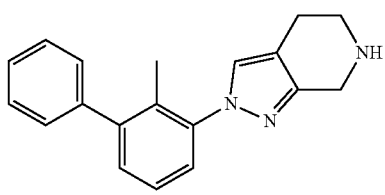 [SMILES: Cc1c(-c2ccccc2)cccc1-n1cc2c(n1)CNCC2]

Step 1: tert-butyl 2-(2-methylbiphenyl-3-yl)-2,4,6,7-tetrahydro-5H-pyrazolo[4,3-c]pyridine-5-carboxylate

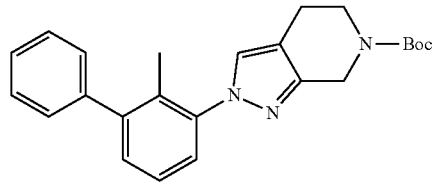 [SMILES: Cc1c(-c2ccccc2)cccc1-n1cc2c(n1)CN(C(=O)OC(C)(C)C)CC2]

This compound was prepared using similar procedures as described for Example 17, Step 2 with tert-butyl 1,4,5,7-tetrahydro-6H-pyrazolo[3,4-c]pyridine-6-carboxylate (Ark Pharm, cat #AK-39955) replacing tert-butyl 1,4,6,7-tetrahydro-5H-pyrazolo[4,3-c]pyridine-5-carboxylate. The resulting mixture was diluted with methylene chloride, washed with saturated NaHCO$_3$, water and brine. The organic layer was dried over Na$_2$SO$_4$, filtered and concentrated. The residue was used in the next step without further purification. LC-MS calculated for $C_{24}H_{28}N_3O_2$ (M+H)$^+$: m/z=390.2; found 390.2.

Step 2: 2-(2-methylbiphenyl-3-yl)-4,5,6,7-tetrahydro-2H-pyrazolo[3,4-c]pyridine

The crude product from Step 1 was dissolved in methylene chloride (0.6 mL) then treated with TFA (0.3 mL). The resulting mixture was stirred at room temperature for 30 min before concentrated and purified by prep-HPLC (pH=2, acetonitrile/water+TFA) to give the desired product as the TFA salt. LC-MS calculated for $C_{19}H_{20}N_3$ (M+H)$^+$: m/z=290.2; found 290.2.

Example 19

7,7-dimethyl-2-(2-methylbiphenyl-3-yl)-4,5,6,7-tetrahydro[1,3]thiazolo[5,4-c]pyridine

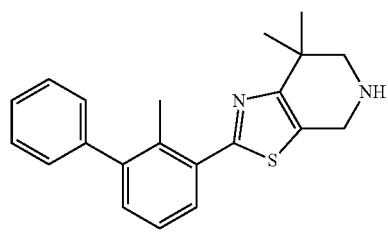 [SMILES: Cc1c(-c2ccccc2)cccc1-c1nc2c(s1)CNCC2(C)C]

Step 1: tert-butyl 5-bromo-3,3-dimethyl-4-oxopiperidine-1-carboxylate

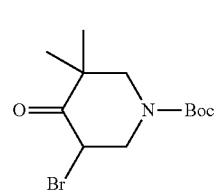 [SMILES: CC(C)(C)OC(=O)N1CC(Br)C(=O)C(C)(C)C1]

To a solution of tert-butyl 3,3-dimethyl-4-oxopiperidine-1-carboxylate (107 mg, 469 μmol) (Combi-blocks, cat #QA-1430) in chloroform (2.0 mL) was added bromine (24.2 μL, 469 μmol) in chloroform (0.5 mL) at 0° C. After stirred at the same temperature for 15 min, it was allowed to warm up to r.t. and stirred for another 30 min. The resulted mixture was concentrated to dryness and used in the next step without further purification. LC-MS calculated for $C_{12}H_{21}BrNO_3$ $(M+H)^+$: m/z=306.2; found 306.2.

Step 2: tert-butyl 2-amino-7,7-dimethyl-6,7-dihydro[1,3]thiazolo[5,4-c]pyridine-5(4H)-carboxylate

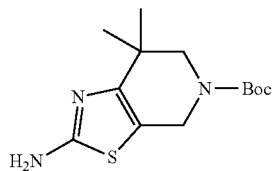

To a solution of above crude product in ethanol (0.5 mL) was added thiourea (53.5 mg, 703 μmol). The resulted mixture was heated at 80° C. for 3 h then concentrated to dryness and used in the next step without further purification. LC-MS calculated for $C_{13}H_{22}N_3O_2S$ $(M+H)^+$: m/z=284.2; found 284.2.

Step 3: tert-butyl 2-bromo-7,7-dimethyl-6,7-dihydro[, 3]thiazolo[5,4-c]pyridine-5(4H)-carboxylate

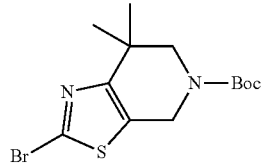 [SMILES: CC(C)(C)OC(=O)N1Cc2sc(Br)nc2C(C)(C)C1]

To a solution of the crude product from Step 2 in acetonitrile (1.0 mL) was added tert-butyl nitrite (94.8 μL, 797 μmol) and copper(II) bromide (157 mg, 703 μmol). After the reaction mixture was stirred for 3 h, it was diluted with methylene chloride and washed over water. The organic layer was dried over $Na_2SO_4$, filtered and concentrated. The residue was used in the next step without further purification. LC-MS calculated for $C_{13}H_{20}BrN_2O_2S$ $(M+H)^+$: m/z=347.2; found 347.2.

Step 4: tert-butyl 7,7-dimethyl-2-(2-methylbiphenyl-3-yl)-6,7-dihydro[1,3]thiazolo[5,4-c]pyridine-5(4H)-carboxylate

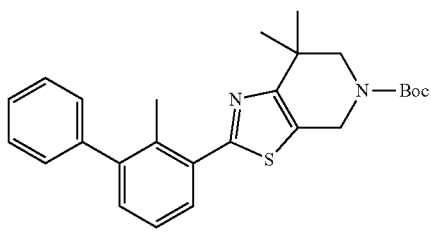 [SMILES: Cc1c(-c2ccccc2)cccc1-c1nc2c(s1)CN(C(=O)OC(C)(C)C)CC2(C)C]

This compound was prepared using similar procedures as described for Example 1, Step 2 with tert-butyl 2-bromo-7,7-dimethyl-6,7-dihydro[1,3]thiazolo[5,4-c]pyridine-5(4H)-carboxylate (Step 3) replacing tert-butyl 2-bromo-6,7-dihydro[1,3]thiazolo[4,5-c]pyridine-5(4H)-carboxylate. The reaction mixture was diluted with methylene chloride, washed with saturated $NaHCO_3$, water and brine. The organic layer was dried over $Na_2SO_4$, filtered and concentrated. The residue was used in the next step without further purification. LC-MS calculated for $C_{26}H_{31}N_2O_2S$ $(M+H)^+$: m/z=435.2; found 435.2.

Step 5: 7,7-dimethyl-2-(2-methylbiphenyl-3-yl)-4,5,6,7-tetrahydro[1,3]thiazolo[5,4-c]pyridine The crude product from Step 4 was dissolved in methylene chloride (0.6 mL) then treated with TFA (0.3 mL). The resulting mixture was stirred at room temperature for 30 min before concentrated and purified by prep-HPLC (pH=2, acetonitrile/water+TFA) to give the desired product as the TFA salt. LC-MS calculated for $C_{21}H_{23}N_2S$ $(M+H)^+$: m/z=335.2; found 335.2.

Example 20

2-(2-methylbiphenyl-3-yl)-5,6,7,8-tetrahydroimidazo[1,2-a]pyrazine

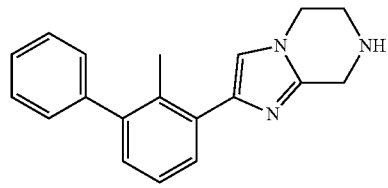 [SMILES: Cc1c(-c2ccccc2)cccc1-c1cn2c(n1)CNCC2]

Step 1: 1-(2-methylbiphenyl-3-yl)ethanone

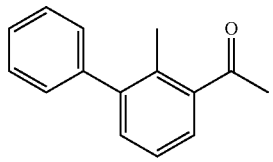 [SMILES: CC(=O)c1cccc(-c2ccccc2)c1C]

To a solution of 1-(3-bromo-2-methylphenyl)ethanone (500 mg, 2.35 mmol) (Astatech, cat #CL9266), phenylboronic acid (300 mg, 2.46 mmol) and sodium carbonate (622 mg, 5.87 mmol) in tert-butyl alcohol (10 mL) and water (4 mL) was added Pd-127 (178 mg, 235 μmol). The resulted mixture was heated at 105° C. for 2 h, and then was diluted with methylene chloride, washed with saturated $NaHCO_3$, water and brine. The organic layer was dried over $Na_2SO_4$, filtered and concentrated. The residue was purified by flash chromatography on a silica gel column eluting with 0 to 50% ethyl acetate in hexanes to give the desired product (400 mg, 80%). LC-MS calculated for $C_{15}H_{15}O$ $(M+H)^+$: m/z=211.2; found 211.2.

Step 2: 2-bromo-1-(2-methylbiphenyl-3-yl)ethanone

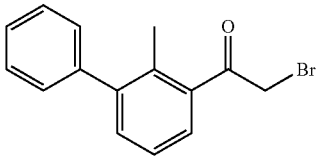 [SMILES: Cc1c(C(=O)CBr)cccc1-c1ccccc1]

To a solution of 1-(2-methylbiphenyl-3-yl)ethanone (1.25 g, 5.94 mmol) in ethyl acetate (30 mL) was added copper(II) bromide (5.3 g, 24 mmol) then stirred at 80° C. for 2 hours, then it was filtered and concentrated to dryness under reduced pressure. The residue was purified by flash chromatography on a silica gel column eluting with 0 to 50% ethyl acetate in hexanes to give the desired product (1.50 g, 87%). LC-MS calculated for $C_{15}H_{14}BrO$ (M+H)$^+$: m/z=289.2; found 289.2.

Step 3: 2-(2-methylbiphenyl-3-yl)imidazo[1,2-a]pyrazine

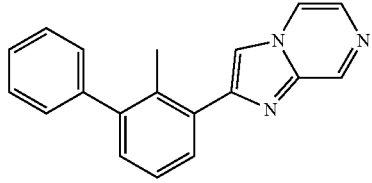 [SMILES: Cc1c(-c2ccccc2)cccc1-c1cn2ccncc2n1]

A solution of 2-bromo-1-(2-methylbiphenyl-3-yl)ethanone (20 mg, 69 μmol), aminopyrazine (9.87 mg, 104 μmol) in acetonitrile (0.4 mL) was heated at 100° C. for 2 h, then it was concentrated to dryness under reduced pressure. The residue was used in the next step without further purification. LC-MS calculated for $C_{19}H_{16}N_3$ (M+H)$^+$: m/z=286.2; found 286.2.

Step 4: 2-(2-methylbiphenyl-3-yl)-5,6,7,8-tetrahydroimidazo[1,2-a]pyrazine

To the solution of the crude product from Step 3 in methanol (2.0 mL) was added Pd/C (10 mg) and the resulting mixture was stirred at r.t. for 4 h under an atmosphere of H$_2$. The resulting mixture was filtered and purified by prep-HPLC (pH=2, acetonitrile/water+TFA) to give the desired product as the TFA salt. LC-MS calculated for $C_{19}H_{20}N_3$ (M+H)$^+$: m/z=290.2; found 290.2.

Example 21

2-(2-methylbiphenyl-3-yl)-4,5,6,7-tetrahydro-1H-imidazo[4,5-c]pyridine

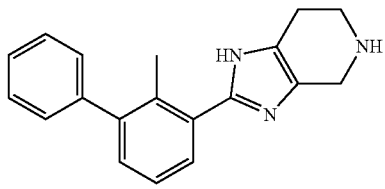 [SMILES: Cc1c(-c2ccccc2)cccc1-c1nc2c([nH]1)CCNC2]

Step 1: 2-methylbiphenyl-3-carbaldehyde

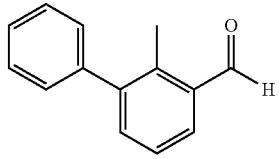

To a solution of (2-methylbiphenyl-3-yl)methanol (TCI, Cat #: H0777: 4.12 g, 20.8 mmol) in methylene chloride (60 mL) was slowly added Dess-Martin periodinane (9.25 g, 21.8 mmol). The resulting mixture was stirred at r.t. for 30 min, and then washed with saturated NaHCO$_3$, water and brine. The organic layer was dried over Na$_2$SO$_4$, filtered and concentrated. The residue was purified by flash chromatography on a silica gel column eluting with 0 to 30% ethyl acetate in hexanes to give the desired product (3.30 g, 80%). LC-MS calculated for $C_{14}H_{13}O$ (M+H)$^+$: m/z=197.2; found 197.2.

Step 2: 2-(2-methylbiphenyl-3-yl)-1H-imidazo[4,5-c]pyridine

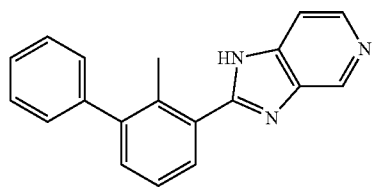 [SMILES: Cc1c(-c2ccccc2)cccc1-c1nc2cnccc2[nH]1]

To a solution of pyridine-3,4-diamine (15 mg, 0.14 mmol) and 2-methylbiphenyl-3-carbaldehyde (30 mg, 0.15 mmol) in methanol (0.69 mL) was added catalytic amount of zinc triflate (5 mg), then heated at 70° C. for 36 h. The resulting mixture was filtered and purified by prep-HPLC (pH=2, acetonitrile/water+TFA) to give the desired product as the TFA salt. LC-MS calculated for $C_{19}H_{16}N_3$ (M+H)$^+$: m/z=286.2; found 286.2.

Step 3: 5-benzyl-2-(2-methylbiphenyl-3-yl)-4,5,6,7-tetrahydro-1H-imidazo[4,5-c]pyridine

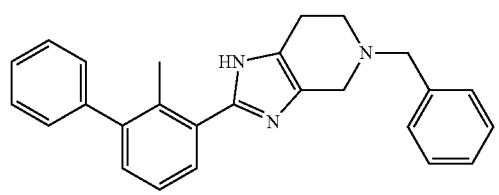 [SMILES: Cc1c(-c2ccccc2)cccc1-c1nc2c([nH]1)CCN(Cc1ccccc1)C2]

To a solution of 2-(2-methylbiphenyl-3-yl)-1H-imidazo[4,5-c]pyridine (10 mg, TFA salt) in DMF (0.3 mL) was added benzylbromide (10 μL) and DIPEA (10 μL). The resulting mixture was heated at 100° C. for 2 h, then concentrated to dryness. The crude mixture was dissolved in methanol (2.0 mL) and NaBH$_4$ (10 mg) was added at r.t. The resulting mixture was stirred for 30 min and purified by prep-HPLC (pH=2, acetonitrile/water+TFA) to give the desired product as the TFA salt. LC-MS calculated for C$_{26}$H$_{26}$N$_3$ (M+H)$^+$: m/z=380.2; found 380.2.

Step 4: 2-(2-methylbiphenyl-3-yl)-4,5,6,7-tetrahydro-1H-imidazo[4,5-c]pyridine To a solution of 5-benzyl-2-(2-methylbiphenyl-3-yl)-4,5,6,7-tetrahydro-1H-imidazo[4,5-c]pyridine (5 mg, TFA salt) in methanol (2.0 mL) was added Pd/C (10 mg) and stirred at r.t. for 4 h under an atmosphere of H$_2$. The resulting mixture was filtered and purified by prep-HPLC (pH=2, acetonitrile/water+TFA) to give the desired product as the TFA salt. LC-MS calculated for C$_{19}$H$_{20}$N$_3$ (M+H)$^+$: m/z=290.2; found 290.2.

Example 22

2-(2-methylbiphenyl-3-yl)-4,5,6,7-tetrahydro[1,3]oxazolo[5,4-c]pyridine

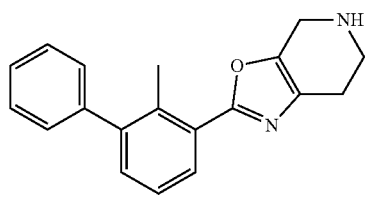 [SMILES: Cc1c(-c2ccccc2)cccc1-c1nc2c(o1)CNCC2]

Step 1: 2-(2-methylbiphenyl-3-yl)[1,3]oxazolo[5,4-c]pyridine

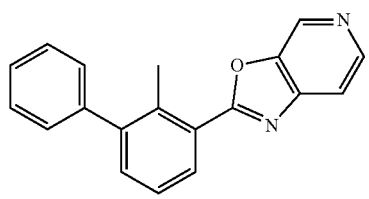 [SMILES: Cc1c(-c2ccccc2)cccc1-c1nc2ccncc2o1]

To a mixture of 2-methylbiphenyl-3-carboxylic acid (100 mg, 471 µmol) (Combi-Blocks, cat #YA-8643) and triethylamine (65.7 µL, 471 µmol) in methylene chloride (2.0 mL) was added cyanuric chloride (28.9 mg, 157 µmol). The resulting mixture was heated at 60° C. for 20 min then 4-aminopyridin-3-ol (51.9 mg, 471 µmol) was added. The resulting mixture was heated at the same temperature for 18 h then cooled to room temperature and concentrated. The residue was purified by prep-HPLC (pH=2, acetonitrile/water+TFA) to give the desired product as the TFA salt. LC-MS calculated for C$_{19}$H$_{15}$N$_2$O (M+H)$^+$: m/z=287.2; found 287.2.

Step 2: 5-benzyl-2-(2-methylbiphenyl-3-yl)-4,5,6,7-tetrahydro[1,3]oxazolo[5,4-c]pyridine

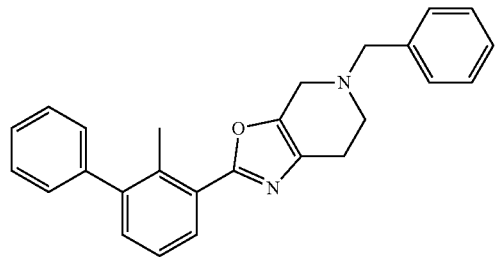 [SMILES: Cc1c(-c2ccccc2)cccc1-c1nc2c(o1)CN(Cc1ccccc1)CC2]

This compound was prepared using similar procedures as described for Example 21, Step 3 with 2-(2-methylbiphenyl-3-yl)[1,3]oxazolo[5,4-c]pyridine (Step 1) replacing 2-(2-methylbiphenyl-3-yl)-1H-imidazo[4,5-c]pyridine. The resulting mixture was purified by prep-HPLC (pH=2, acetonitrile/water+TFA) to give the desired product as the TFA salt. LC-MS calculated for C$_{26}$H$_{25}$N$_2$O (M+H)$^+$: m/z=381.2; found 381.3.

Step 3: 2-(2-methylbiphenyl-3-yl)-4,5,6,7-tetrahydro[,3]oxazolo[5,4-c]pyridine This compound was prepared using similar procedures as described for Example 21, Step 4 with 5-benzyl-2-(2-methylbiphenyl-3-yl)-4,5,6,7-tetrahydro[1,3]oxazolo[5,4-c]pyridine (Step 2) replacing 5-benzyl-2-(2-methylbiphenyl-3-yl)-4,5,6,7-tetrahydro-1H-imidazo[4,5-c]pyridine. The resulting mixture was purified by prep-HPLC (pH=2, acetonitrile/water+TFA) to give the desired product as the TFA salt. LC-MS calculated for C$_{19}$H$_{19}$N$_2$O (M+H)$^+$: m/z=291.2; found 291.2.

Example 23

2-(2-methylbiphenyl-3-yl)-4,5,6,7-tetrahydro[1,3]oxazolo[4,5-c]pyridine

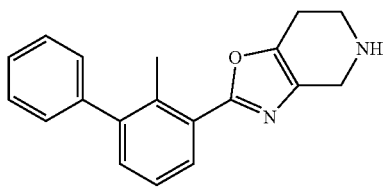 [SMILES: Cc1c(-c2ccccc2)cccc1-c1nc2c(o1)CCNC2]

This compound was prepared using similar procedures as described for Example 22 with 3-aminopyridin-4-ol replacing 4-aminopyridin-3-ol in Step 1. The reaction mixture was purified by prep-HPLC (pH=2, acetonitrile/water+TFA) to give the desired product as the TFA salt. LC-MS calculated for C$_{19}$H$_{19}$N$_2$O (M+H)$^+$: m/z=291.2; found 291.2.

Example 24

5-methyl-2-(2-methylbiphenyl-3-yl)-4,5,6,7-tetrahydro[1,3]oxazolo[4,5-c]pyridine

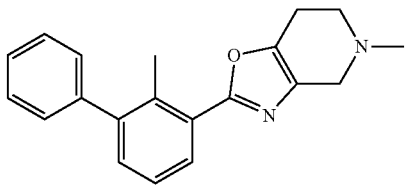 [SMILES: Cc1c(-c2ccccc2)cccc1-c1nc2c(o1)CCN(C)C2]

This compound was prepared using similar procedures as described for Example 3 with 2-(2-methylbiphenyl-3-yl)-4,5,6,7-tetrahydro[1,3]oxazolo[4,5-c]pyridine (Example 23) replacing 2-(2-methylbiphenyl-3-yl)-4,5,6,7-tetrahydro[1,3]thiazolo[5,4-c]pyridine. The resulting mixture was purified by prep-HPLC (pH=2, acetonitrile/water+TFA) to give the desired product as the TFA salt. LC-MS calculated for $C_2H_{21}N_2O$ (M+H)$^+$: m/z=305.2; found 305.2.

Example 25

2-(2-methylbiphenyl-3-yl)-5,6,7,8-tetrahydro[1,2,4]triazolo[1,5-a]pyrazine

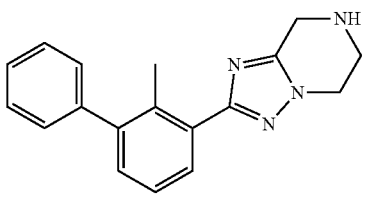 [SMILES: Cc1c(-c2ccccc2)cccc1-c1nc2n(n1)CCNC2]

Step 1: ethyl [(pyrazin-2-ylamino)carbonothioyl]carbamate

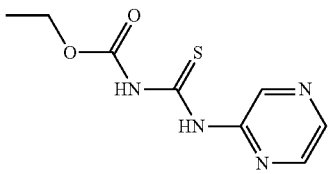

To a solution of aminopyrazine (200 mg, 2.10 mmol) in 1,4-dioxane (10 mL) was added ethoxycarbonyl isothiocyanate (273 μL, 2.42 mmol). The reaction mixture was stirred at r.t. for 15 h. The resulted mixture was concentrated to dryness and used in the next step without further purification. LC-MS calculated for $C_8H_{11}N_4O_2S$ (M+H)$^+$: m/z=227.2; found 227.2.

Step 2: [1,2,4]triazolo[1,5-a]pyrazin-2-amine

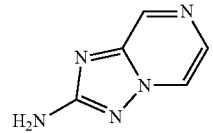

To a solution of the crude product from Step 1 in methanol (7.0 mL) and ethanol (7.0 mL) was added hydroxyamine-hydrochoride (438 mg, 6.31 mmol) and N,N-diisopropylethylamine (733 μL, 4.20 mmol). The resulting mixture was heated at 75° C. for 7 h. After cooled to room temperature, the precipitated product (yellow solid) was filtered and washed with small amount of methanol. LC-MS calculated for $C_5H_6N_5$ (M+H)$^+$: m/z=136.2; found 136.2.

Step 3: 2-bromo[1,2,4]triazolo[1,5-a]pyrazine

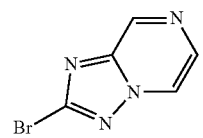

This compound was prepared using similar procedures as described for Example 19, Step 3 with [1,2,4]triazolo[1,5-a]pyrazin-2-amine (Step 2) replacing tert-butyl 2-amino-7,7-dimethyl-6,7-dihydro[1,3]thiazolo[5,4-c]pyridine-5(4H)-carboxylate. After stirred for 3 h, the reaction mixture was diluted with methylene chloride and washed over water. The organic layer was dried over Na$_2$SO$_4$, filtered and concentrated. The residue was used in the next step without further purification. LC-MS calculated for $C_5H_4BrN_4$ (M+H)$^+$: m/z=199.2; found 199.2.

Step 4: 2-(2-methylbiphenyl-3-yl)[1,2,4]triazolo[1,5-a]pyrazine

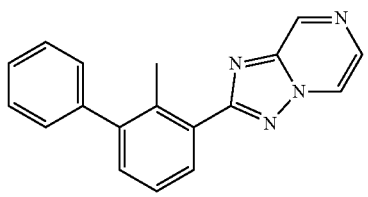 [SMILES: Cc1c(-c2ccccc2)cccc1-c1nc2cnccn2n1]

This compound was prepared using similar procedures as described for Example 1, Step 2 with 2-bromo[1,2,4]triazolo[1,5-a]pyrazine (Step 3) replacing tert-butyl 2-bromo-6,7-dihydro[1,3]thiazolo[4,5-c]pyridine-5(4H)-carboxylate. The reaction mixture was diluted with methylene chloride, washed with saturated NaHCO$_3$, water and brine. The organic layer was dried over Na$_2$SO$_4$, filtered and concentrated. The residue was used in the next step without further purification. LC-MS calculated for $C_{18}H_{15}N_4$ (M+H)$^+$: m/z=287.2; found 287.2.

Step 5: 2-(2-methylbiphenyl-3-yl)-5,6,7,8-tetrahydro[1,2,4]triazolo[1,5-a]pyrazine The crude product from Step 4 was dissolved in methanol (1.0 mL) then treated with LiBH$_4$ (10 mg) at 50° C. for 30 min. The resulting mixture was quenched with TFA before concentrated and purified by prep-HPLC (pH=2, acetonitrile/water+TFA) to give the desired product as the TFA salt. LC-MS calculated for $C_{18}H_{19}N_4$ (M+H)$^+$: m/z=291.2; found 291.2.

Example 26

2-[2-(2,3-dihydro-1,4-benzodioxin-6-yl)-3-methylpyridin-4-yl]-4,5,6,7-tetrahydro[1,3]thiazolo[5,4-c]pyridine

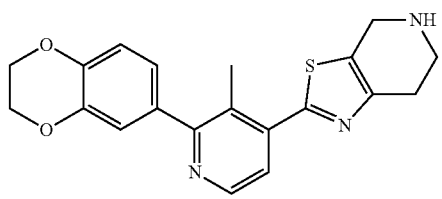 [SMILES: Cc1c(-c2nc3c(s2)CNCC3)ccnc1-c1ccc2c(c1)OCCO2]

Step 1: (2-chloro-3-methylpyridin-4-yl)boronic acid

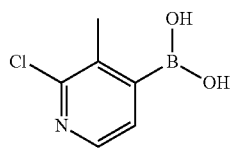

A mixture of 2-chloro-4-iodo-3-methylpyridine (250 mg, 986 μmol) (AstaTech, cat #22441) and boric acid, trimethyl ester (224 μL, 1.97 mmol) in tetrahydrofuran (5.0 mL) was added 2.5 M n-butyllithium in hexanes (789 μL, 1.97 mmol) dropwise at −78° C. The reaction mixture was allowed to warm up to r.t. after 90 min and stirred for another 30 min. The resulting mixture was concentrated and acetonitrile (5 mL) was added. The resulting suspension was filtered through celite then concentrated to give the desired product. LCMS calculated for $C_6H_8BClNO_2$ (M+H)$^+$: m/z=172.2; found 172.2.

Step 2: tert-butyl 2-(2-chloro-3-methylpyridin-4-yl)-6,7-dihydro[1,3]thiazolo[5,4-c]pyridine-5(4H)-carboxylate

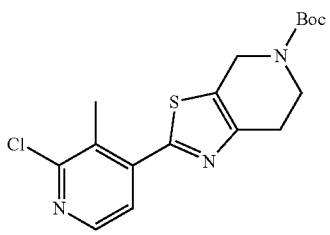 [SMILES: Cc1c(-c2nc3c(s2)CN(C(=O)OC(C)(C)C)CC3)ccnc1Cl]

To a solution of (2-chloro-3-methylpyridin-4-yl)boronic acid (Example 26, Step 1: 170 mg, 1.0 mmol), tert-butyl 2-bromo-6,7-dihydro[1,3]thiazolo[5,4-c]pyridine-5(4H)-carboxylate (AstaTech, cat #AB1021: 320 mg, 1.0 mmol) and sodium carbonate (314 mg, 2.96 mmol) in tert-butyl alcohol (10 mL) and water (5 mL) was added Pd-127 (75 mg, 0.10 mmol). The resulting mixture was purged with $N_2$, then heated at 105° C. for 2 h. The reaction mixture was diluted with methylene chloride, washed with saturated $NaHCO_3$, water and brine. The organic layer was dried over $Na_2SO_4$, filtered and concentrated. The residue was used in the next step without further purification. LC-MS calculated for $C_{17}H_{21}CN_3O_2S$ (M+H)$^+$: m/z=366.1; found 366.2.

Step 3: tert-butyl 2-[2-(2,3-dihydro-1,4-benzodioxin-6-yl)-3-methylpyridin-4-yl]-6,7-dihydro[1,3]thiazolo[5,4-c]pyridine-5(4H)-carboxylate

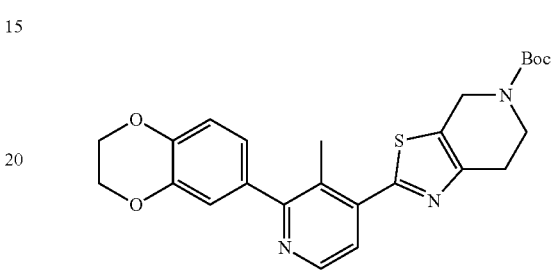

To a solution of 2,3-dihydro-1,4-benzodioxin-6-ylboronic acid (Combi-blocks, Cat #BB-8311: 36 mg, 0.20 mmol), tert-butyl 2-bromo-6,7-dihydro[1,3]thiazolo[5,4-c]pyridine-5(4H)-carboxylate (Example 26, Step 2: 32 mg, 0.10 mmol) and sodium carbonate (31 mg, 0.30 mmol) in tert-butyl alcohol (1.0 mL) and water (0.6 mL) was added Pd-127 (15 mg, 0.020 mmol). The resulting mixture was purged with $N_2$, then heated at 105° C. for 1.5 h. The reaction mixture was diluted with methylene chloride, washed with saturated $NaHCO_3$, water and brine. The organic layer was dried over $Na_2SO_4$, filtered and concentrated. The residue was used in the next step without further purification. LC-MS calculated for $C_{25}H_{28}N_3O_4S$ (M+H)$^+$: m/z=466.1; found 466.2.

Step 4: 2-[2-(2,3-dihydro-1,4-benzodioxin-6-yl)-3-methylpyridin-4-yl]-4,5,6,7-tetrahydro[1,3]thiazolo[5,4-c]pyridine The crude product from Step 3 was dissolved in methylene chloride (0.6 mL) then treated with TFA (0.3 mL). The resulting mixture was stirred at room temperature for 30 min then concentrated and purified by prep-HPLC (pH=2, acetonitrile/water+TFA) to give the desired product as the TFA salt. LC-MS calculated for $C_2H_2N_3O_2S$ (M+H)$^+$: m/z=366.2; found 366.2.

Example 27

2-[2-methyl-3-(3-thienyl)phenyl]-4,5,6,7-tetrahydro[1,3]thiazolo[5,4-c]pyridine

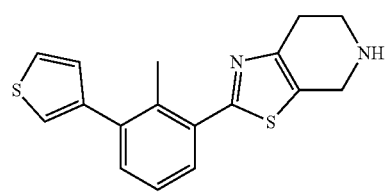 [SMILES: Cc1c(-c2ccsc2)cccc1-c1nc2c(s1)CNCC2]

Step 1: tert-butyl 2-(3-chloro-2-methylphenyl)-6,7-dihydro[, 3]thiazolo[5,4-c]pyridine-5(4H)-carboxylate

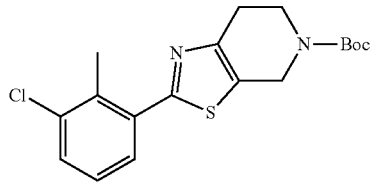 [SMILES: Cc1c(Cl)cccc1-c1nc2c(s1)CN(C(=O)OC(C)(C)C)CC2]

To a solution of (3-chloro-2-methylphenyl)boronic acid (Combi-blocks, cat #BB-2035: 64 mg, 0.38 mmol), tert-butyl 2-bromo-6,7-dihydro[1,3]thiazolo[5,4-c]pyridine-5(4H)-carboxylate (AstaTech, cat #AB1021: 100 mg, 0.31 mmol) and sodium carbonate (100 mg, 0.94 mmol) in tert-butyl alcohol (3.2 mL) and water (2 mL) was added Pd-127 (47 mg, 0.063 mmol). The resulting mixture was purged with $N_2$, then heated at 105° C. for 2 h. The reaction mixture was diluted with methylene chloride, washed with saturated $NaHCO_3$, water and brine. The organic layer was dried over $Na_2SO_4$, filtered and concentrated. The residue was purified by flash chromatography on a silica gel column eluting with 0 to 40% ethyl acetate in hexanes to give the desired product (114 mg, 83%). LC-MS calculated for $C_{18}H_{22}ClN_2O_2S$ $(M+H)^+$: m/z=365.1; found 365.2.

Step 2: tert-butyl 2-[2-methyl-3-(4,4,5,5-tetramethyl-1,3,2-dioxaborolan-2-yl)phenyl]-6,7-dihydro[1,3]thiazolo[5,4-c]pyridine-5(4H)-carboxylate

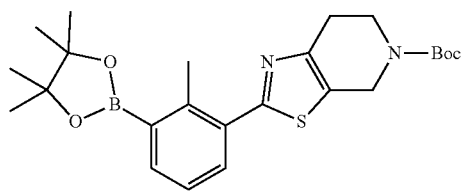 [SMILES: Cc1c(B2OC(C)(C)C(C)(C)O2)cccc1-c1nc2c(s1)CN(C(=O)OC(C)(C)C)CC2]

A mixture of tert-butyl 2-(3-chloro-2-methylphenyl)-6,7-dihydro[1,3]thiazolo[5,4-c]pyridine-5(4H)-carboxylate (Example 26, Step 1: 95 mg, 0.26 mmol), 4,4,5,5,4',4',5',5'-octamethyl-[2,2']bi[[1,3,2]dioxaborolanyl] (200 mg, 0.78 mmol), palladium acetate (2.5 mg, 0.014 mmol), $K_3PO_4$ (170 mg, 0.78 mmol) and 2-(dicyclohexylphosphino)-2',6'-dimethoxy-1,1'-biphenyl (11 mg, 0.026 mmol) in 1,4-dioxane (1 mL) was degassed and stirred at r.t. for 3 d. The reaction mixture was diluted with methylene chloride, washed with saturated $NaHCO_3$, water and brine. The organic layer was dried over $Na_2SO_4$, filtered and concentrated. The residue was purified by flash chromatography on a silica gel column eluting with 0 to 5% ethyl acetate in methylene chloride to give the desired product (108 mg, 90%). LC-MS calculated for $C_{24}H_{34}BN_2O_4S$ $(M+H)^+$: m/z=457.2; found 457.2.

Step 3: tert-butyl 2-[2-methyl-3-(3-thienyl)phenyl]-6,7-dihydro[, 3]thiazolo[5,4-c]pyridine-5(4H)-carboxylate

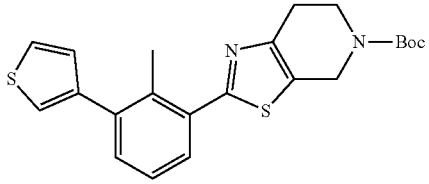 [SMILES: Cc1c(-c2ccsc2)cccc1-c1nc2c(s1)CN(C(=O)OC(C)(C)C)CC2]

To a solution of tert-butyl 2-[2-methyl-3-(4,4,5,5-tetramethyl-1,3,2-dioxaborolan-2-yl)phenyl]-6,7-dihydro[1,3]thiazolo[5,4-c]pyridine-5(4H)-carboxylate (Example 26, Step 2: mg, 0.033 mmol), thiophene, 3-bromo- (6.2 µL, 0.066 mmol) and sodium carbonate (8.7 mg, 0.082 mmol) in tert-butyl alcohol (0.3 mL) and water (0.2 mL) was added Pd-127 (5.0 mg, 0.0066 mmol). The resulting mixture was purged with $N_2$, then heated at 105° C. for 1.5 h. The reaction mixture was diluted with methylene chloride, washed with saturated $NaHCO_3$, water and brine. The organic layer was dried over $Na_2SO_4$, filtered and concentrated. The residue was used in the next step without further purification. LC-MS calculated for $C_{22}H_{25}N_2O_2S_2$ $(M+H)^+$: m/z=413.1; found 413.2.

Step 4: 2-[2-methyl-3-(3-thienyl)phenyl]-4,5,6,7-tetrahydro[1,3]thiazolo[5,4-c]pyridine The crude product from Step 3 was dissolved in methylene chloride (0.6 mL) then treated with TFA (0.3 mL). The resulting mixture was stirred at room temperature for 30 min then concentrated and purified by prep-HPLC (pH=2, acetonitrile/water+TFA) to give the desired product as the TFA salt. LC-MS calculated for $C_{17}H_{17}N_2S_2$ $(M+H)^+$: m/z=313.1; found 313.2.

Example 28

2-(3'-methoxy-2-methylbiphenyl-3-yl)-4,5,6,7-tetrahydro[1,3]thiazolo[5,4-c]pyridine

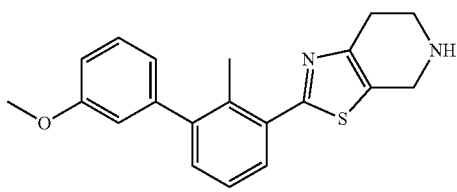

This compound was prepared using similar procedures as described for Example 27, Step 1-4 with 1-bromo-3-methoxybenzene replacing 3-bromothiophene in Step 3. The reaction mixture was purified by prep-HPLC (pH=2, acetonitrile/water+TFA) to give the desired product as the TFA salt. LC-MS calculated for $C_2H_{21}N_2OS$ $(M+H)^+$: m/z=337; found 337.2.

Example 29

2-[3-(3,6-dihydro-2H-pyran-4-yl)-2-methylphenyl]-4,5,6,7-tetrahydro[1,3]thiazolo[5,4-c]pyridine

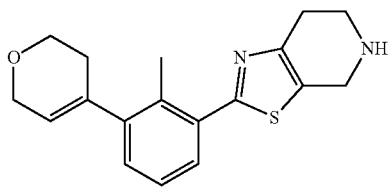 [SMILES: Cc1c(C2=CCOCC2)cccc1-c1nc2c(s1)CNCC2]

This compound was prepared using similar procedures as described for Example 27, Step 1-4 with 4-bromo-3,6-dihydro-2H-pyran (Combi-blocks, cat #OT-0686) replacing 3-bromothiophene in Step 3. The reaction mixture was purified by prep-HPLC (pH=2, acetonitrile/water+TFA) to give the desired product as the TFA salt. LC-MS calculated for $C_{18}H_{21}N_2OS$ (M+H)$^+$: m/z=313.2; found 313.2.

Example 30

2-[3-(2-methoxypyridin-4-yl)-2-methylphenyl]-4,5,6,7-tetrahydro[1,3]thiazolo[5,4-c]pyridine

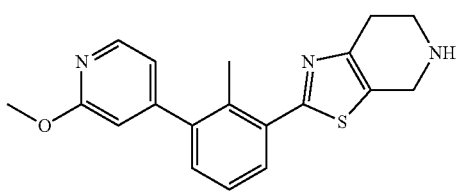 [SMILES: COc1cc(-c2cccc(-c3nc4c(s3)CNCC4)c2C)ccn1]

This compound was prepared using similar procedures as described for Example 27, Step 1-4 with 4-bromo-2-methoxypyridine (ArkPharm, cat #AK-47404) replacing 3-bromothiophene in Step 3. The reaction mixture purified by prep-HPLC (pH=2, acetonitrile/water+TFA) to give the desired product as the TFA salt. LC-MS calculated for $C_{19}H_{20}N_3OS$ (M+H)$^+$: m/z=338.2; found 338.2.

Example 31

2-[3-(5-fluoropyridin-2-yl)-2-methylphenyl]-4,5,6,7-tetrahydro[1,3]thiazolo[5,4-c]pyridine

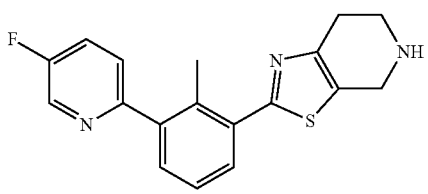 [SMILES: Cc1c(-c2ccc(F)cn2)cccc1-c1nc2c(s1)CNCC2]

This compound was prepared using similar procedures as described for Example 27, Step 1-4 with 2-bromo-5-fluoropyridine (Aldrich, cat #595675) replacing 3-bromothiophene in Step 3. The reaction mixture was purified by prep-HPLC (pH=2, acetonitrile/water+TFA) to give the desired product as the TFA salt. LC-MS calculated for $C_{18}H_{17}FN_3S$ (M+H)$^+$: m/z=326.2; found 326.2.

Example 32

2-(3-cyclohex-1-en-1-yl-2-methylphenyl)-4,5,6,7-tetrahydro[1,3]thiazolo[5,4-c]pyridine

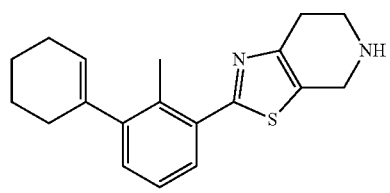 [SMILES: Cc1c(C2=CCCCC2)cccc1-c1nc2c(s1)CNCC2]

This compound was prepared using similar procedures as described for Example 27 with 1-bromocyclohexene (Combi-blocks, cat #OT-0350) replacing 3-bromothiophene in Step 3. The reaction mixture was purified by prep-HPLC (pH=2, acetonitrile/water+TFA) to give the desired product as the TFA salt. LC-MS calculated for $C_{19}H_{23}N_2S$ (M+H)$^+$: m/z=311.2; found 311.2.

Example 33

2-(3'-ethoxy-2-methylbiphenyl-3-yl)-4,5,6,7-tetrahydro[1,3]thiazolo[5,4-c]pyridine

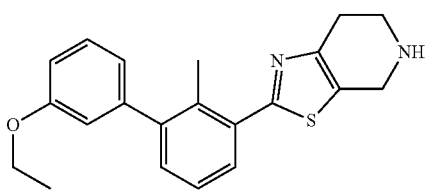 [SMILES: CCOc1cccc(-c2cccc(-c3nc4c(s3)CNCC4)c2C)c1]

This compound was prepared using similar procedures as described for Example 27 with 1-bromo-3-ethoxybenzene (Aldrich, cat #453250) replacing 3-bromothiophene in Step 3. The reaction mixture was purified by prep-HPLC (pH=2, acetonitrile/water+TFA) to give the desired product as the TFA salt. LC-MS calculated for $C_{21}H_{23}N_2OS$ (M+H)$^+$: m/z=351.2; found 351.2.

Example 34

2-(3',5'-dimethoxy-2-methylbiphenyl-3-yl)-4,5,6,7-tetrahydro[1,3]thiazolo[5,4-c]pyridine

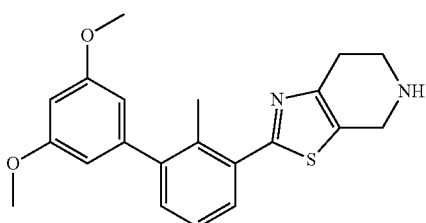

This compound was prepared using similar procedures as described for Example 27 with 3,5-dimethoxybromobenzene (Aldrich, cat #569313) replacing 3-bromothiophene in Step 3. The reaction mixture was purified by prep-HPLC (pH=2, acetonitrile/water+TFA) to give the desired product as the TFA salt. LC-MS calculated for $C_{21}H_{23}N_2O_2S$ (M+H)$^+$: m/z=367.2; found 367.2.

Example 35

4-(2,3-dihydro-1,4-benzodioxin-6-yl)-2-(4,5,6,7-tetrahydro[1,3]thiazolo[5,4-c]pyridin-2-yl)nicotinonitrile

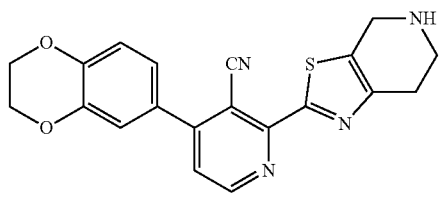 [SMILES: N#Cc1c(-c2ccc3c(c2)OCCO3)ccnc1-c1nc2c(s1)CNCC2]

This compound was prepared using similar procedures as described for Example 16 with 2-chloro-4-iodonicotinonitrile (Aurum Pharmatech, cat #A-6061) replacing 2-chloro-4-iodo-3-methylpyridine. The reaction mixture was purified by prep-HPLC (pH=2, acetonitrile/water+TFA) to give the desired product as the TFA salt. LC-MS calculated for $C_{20}H_{17}N_4O_2S$ (M+H)$^+$: m/z=377.2; found 377.2.

Example 36

2-{[2'-methyl-3'-(4,5,6,7-tetrahydro[1,3]thiazolo[5,4-c]pyridin-2-yl)biphenyl-3-yl]oxy}ethanol

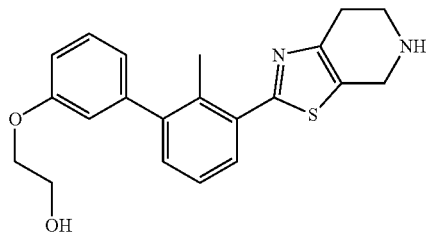 [SMILES: Cc1c(-c2cccc(OCCO)c2)cccc1-c1nc2c(s1)CNCC2]

Step 1: 2-(3-bromophenoxy)ethanol

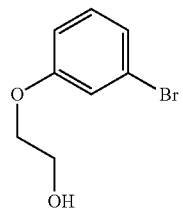 [SMILES: OCCOc1cccc(Br)c1]

To a solution of 3-bromophenol (100 mg, 0.58 mmol) and 2-bromoethanol (36 mg, 0.29 mmol) in methanol (1 mL) was added potassium carbonate (80 mg, 0.58 mmol). The reaction mixture was heated at 55° C. for 4 h, and then diluted with methylene chloride, washed with water and brine. The organic layer was dried over $Na_2SO_4$, filtered and concentrated. The residue was used in the next step without further purification.

Step 2: 2-{[2'-methyl-3'-(4,5,6,7-tetrahydro[1,3]thiazolo[5,4-c]pyridin-2-yl)biphenyl-3-yl]oxy}ethanol This compound was prepared using similar procedures as described for Example 27, Steps 1-4 with 2-(3-bromophenoxy)ethanol (Step 1) replacing 3-bromothiophene in Step 3. The reaction mixture was purified by prep-HPLC (pH=2, acetonitrile/water+TFA) to give the desired product as the TFA salt. LC-MS calculated for $C_{21}H_{23}N_2O_2S$ (M+H)$^+$: m/z=367.2; found 367.2.

Example 37

2-(2',6'-difluoro-3',5'-dimethoxy-2-methylbiphenyl-3-yl)-4,5,6,7-tetrahydro[1,3]thiazolo[5,4-c]pyridine

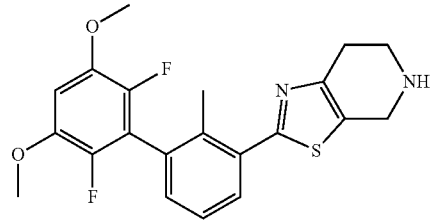 [SMILES: COc1cc(OC)c(F)c(-c2cccc(-c3nc4c(s3)CNCC4)c2C)c1F]

Step 1: 2,4-difluoro-3-iodo-1,5-dimethoxybenzene

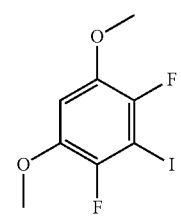

To a stirred slurry of 2,6-difluoro-3,5-dimethoxyaniline (500 mg, 2.64 mmol) in 6.0 M hydrogen chloride in water (4 mL, 24 mmol) was added a solution of sodium nitrite (191 mg, 2.78 mmol) in water (1 mL) dropwise over 15 min at 0° C. After stirring the resulting mixture at 0° C. for another 15 min, a solution of potassium iodide (1.8 g, 10. mmol) in water (2 mL) was slowly added to the resulting orange-red slurry at 0° C. with vigorous stirring. After completion of the addition, the reaction mixture was allowed to warm up to r.t. for 1 hour. The solid was collected by filtration, washed with water and dried under vacuum. 570 mg solid was collected and used directly in the next step.

Step 2: 2-(2',6'-difluoro-3',5'-dimethoxy-2-methylbiphenyl-3-yl)-4,5,6,7-tetrahydro[1,3]thiazolo[5,4-c]pyridine This compound was prepared using similar procedures as described for Example 27, Step 1-4 with 2,4-difluoro-3-iodo-1,5-dimethoxybenzene (Step 1) replacing 3-bromothiophene in Step 3. The reaction mixture was purified by prep-HPLC (pH=2, acetonitrile/water+TFA) to give the desired product as the TFA salt. LC-MS calculated for $C_{21}H_{21}F_2N_2O_2S$ (M+H)$^+$: m/z=403.2; found 403.2.

Example 38

2'-methyl-3'-(4,5,6,7-tetrahydro[1,3]thiazolo[5,4-c]pyridin-2-yl)biphenyl-3-carboxamide

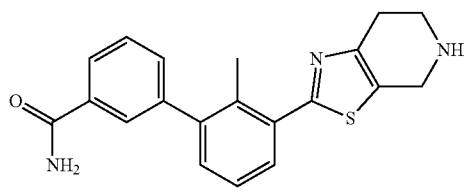 [SMILES: Cc1c(-c2cccc(C(N)=O)c2)cccc1-c1nc2c(s1)CNCC2]

Step 1: tert-butyl 2-[3'-(aminocarbonyl)-2-methylbiphenyl-3-yl]-6,7-dihydro[1,3]thiazolo[5,4-c]pyridine-5(4H)-carboxylate

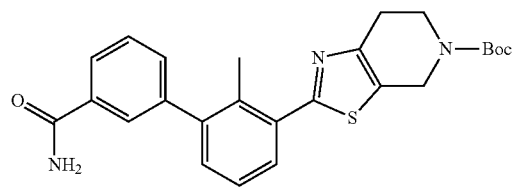 [SMILES: Cc1c(-c2cccc(C(N)=O)c2)cccc1-c1nc2c(s1)CN(C(=O)OC(C)(C)C)CC2]

This compound was prepared using similar procedures as described for Example 27, Step 3 with 3-bromobenzoic acid nitrile (Aldrich, cat #B58202) replacing 3-bromothiophene. The reaction mixture was diluted with methylene chloride, washed with saturated NaHCO$_3$, water and brine. The organic layer was dried over Na$_2$SO$_4$, filtered and concentrated. The residue was used in the next step without further purification. LC-MS calculated for $C_{25}H_{28}N_3O_3S$ (M+H)$^+$: m/z=450.2; found 450.2.

Step 2: 2'-methyl-3'-(4,5,6,7-tetrahydro[1,3]thiazolo[5,4-c]pyridin-2-yl)biphenyl-3-carboxamide The crude product from Step 1 was dissolved in methylene chloride (0.6 mL) then treated with TFA (0.3 mL). The resulting mixture was stirred at room temperature for 30 min then concentrated and purified by prep-HPLC (pH=2, acetonitrile/water+TFA) to give the desired product as the TFA salt. LC-MS calculated for $C_{20}H_{20}N_3OS$ (M+H)$^+$: m/z=350.2; found 350.2.

Example 39

2-[2'-methyl-3'-(4,5,6,7-tetrahydro[1,3]thiazolo[5,4-c]pyridin-2-yl)biphenyl-3-yl]acetamide

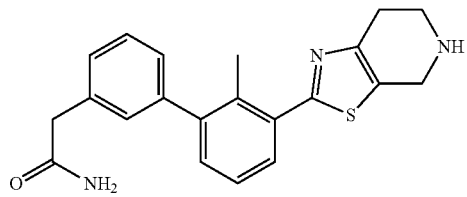 [SMILES: Cc1c(-c2cccc(CC(N)=O)c2)cccc1-c1nc2c(s1)CNCC2]

Step 1: tert-butyl 2-[3'-(2-amino-2-oxoethyl)-2-methylbiphenyl-3-yl]-6,7-dihydro[1,3]thiazolo[5,4-c]pyridine-5(4H)-carboxylate

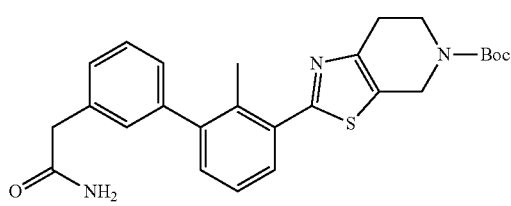 [SMILES: Cc1c(-c2cccc(CC(N)=O)c2)cccc1-c1nc2c(s1)CN(C(=O)OC(C)(C)C)CC2]

This compound was prepared using similar procedures as described for Example 27, Step 3 with (3-bromophenyl)acetonitrile (Aldrich, cat #260088) replacing 3-bromothiophene. The reaction mixture was diluted with methylene chloride, washed with saturated NaHCO$_3$, water and brine. The organic layer was dried over Na$_2$SO$_4$, filtered and concentrated. The residue was used in the next step without further purification. LC-MS calculated for $C_{26}H_{30}N_3O_3S$ (M+H)$^+$: m/z=464.2; found 464.2.

Step 2: 2-[2'-methyl-3'-(4,5,6,7-tetrahydro[1,3]thiazolo[5,4-c]pyridin-2-yl)biphenyl-3-yl]acetamide The crude product from Step 1 was dissolved in methylene chloride (0.6 mL) then treated with TFA (0.3 mL). The resulting mixture was stirred at room temperature for 30 min then concentrated and purified by prep-HPLC (pH=2, acetonitrile/water+TFA) to give the desired product as the TFA salt. LC-MS calculated for $C_{21}H_{22}N_3OS$ (M+H)$^+$: m/z=364.2; found 364.2. $^1$H NMR (500 MHz, CD$_3$OD) δ 7.57-7.53 (m, 1H), 7.43-7.38 (m, 1H), 7.38-7.32 (m, 3H), 7.31-7.27 (m, 1H), 7.24-7.20 (m, 1H), 4.62-4.54 (m, 2H), 3.71-3.64 (m, 2H), 3.58 (s, 2H), 3.21 (t, J=6.2 Hz, 2H), 2.31 (s, 3H).

Example 40

2-[2-methyl-3-(1-methyl-1H-indazol-4-yl)phenyl]-4,5,6,7-tetrahydro[1,3]thiazolo[5,4-c]pyridine

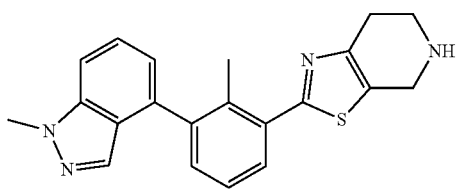 [SMILES: Cc1c(-c2nc3c(s2)CNCC3)cccc1-c1cccc2c1cnn2C]

Step 1: 4-bromo-1-methyl-H-indazole

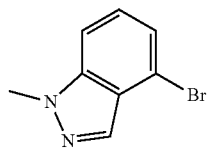

To a solution of 4-bromo-H-indazole (Aldrich, cat #776610: 100. mg, 0.508 mmol) in acetone (2.5 mL) was added potassium hydroxide (85.4 mg, 1.52 mmol). The resulting mixture was stirred at room temperature for 10 min then methyl iodide (63.2 µL, 1.02 mmol) was added. The mixture was stirred at room temperature overnight then concentrated to give a mixture of 4-bromo-2-methyl-2H-indazole and 4-bromo-1-methyl-1H-indazole, which was used in the next step without further purification. LC-MS calculated for $C_8H_8BrN_2$ $(M+H)^+$: m/z=211.0; found 211.1.

Step 2: 2-[2-methyl-3-(1-methyl-H-indazol-4-yl)phenyl]-4,5,6,7-tetrahydro[1,3]thiazolo[5,4-c]pyridine This compound was prepared using similar procedures as described for Example 27, Step 1-4 with 4-bromo-1-methyl-1H-indazole (crude product from Step 1) replacing 3-bromothiophene in Step 3. The reaction mixture was purified by prep-HPLC (pH=2, acetonitrile/water+TFA) to give the desired product as the TFA salt. LC-MS calculated for $C_{21}H_{21}N_4S$ $(M+H)^+$: m/z=361.1; found 361.2. $^1H$ NMR (600 MHz, $CD_3OD$) δ 7.69-7.67 (m, 1H), 7.66-7.63 (m, 1H), 7.61-7.58 (m, 1H), 7.55-7.51 (m, 1H), 7.46-7.41 (m, 2H), 7.08 (d, J=6.9 Hz, 1H), 4.62-4.56 (m, 2H), 4.12 (s, 3H), 3.67 (t, J=6.2 Hz, 2H), 3.22 (t, J=6.2 Hz, 2H), 2.23 (s, 3H).

Example A. PD-1/PD-L1 Homogeneous Time-Resolved Fluorescence (HTRF) Binding Assay The assays were conducted in a standard black 384-well polystyrene plate with a final volume of 20 µL. Inhibitors were first serially diluted in DMSO and then added to the plate wells before the addition of other reaction components. The final concentration of DMSO in the assay was 1%. The assays were carried out at 25° C. in the PBS buffer (pH 7.4) with 0.05% Tween-20 and 0.1% BSA. Recombinant human PD-L1 protein (19-238) with a His-tag at the C-terminus was purchased from AcroBiosystems (PD1-H5229). Recombinant human PD-1 protein (25-167) with Fc tag at the C-terminus was also purchased from AcroBiosystems (PD1-H5257). PD-L1 and PD-1 proteins were diluted in the assay buffer and 10 µL was added to the plate well. Plates were centrifuged and proteins were preincubated with inhibitors for 40 minutes. The incubation was followed by the addition of 10 µL of HTRF detection buffer supplemented with Europium cryptate-labeled anti-human IgG (PerkinElmer-AD0212) specific for Fc and anti-His antibody conjugated to SureLight®-Allophycocyanin (APC, PerkinElmer-AD0059H). After centrifugation, the plate was incubated at 25° C. for 60 min. before reading on a PHERAstar FS plate reader (665 nm/620 nm ratio). Final concentrations in the assay were ~3 nM PD1, 10 nM PD-L1, 1 nM europium anti-human IgG and 20 nM anti-His-Allophycocyanin. $IC_{50}$ determination was performed by fitting the curve of percent control activity versus the log of the inhibitor concentration using the GraphPad Prism 5.0 software.

Compounds of the present disclosure, as exemplified in Examples 1-40, showed $IC_{50}$ values in the following ranges: += $IC_{50}$ ≤100 nM; ++=100 nM< $IC_{50}$ ≤500 nM; +++=500 nM< $IC_{50}$ ≤10000 nM Data obtained for the Example compounds using the PD-1/PD-L homogenous time-resolved fluorescence (HTRF) binding assay described in Example A is provided in Table 1.

TABLE 1

| Example | PD-1/PD-L1 HTRF $IC_{50}$ (nM) |
|---|---|
| 1 | +++ |
| 2 | + |
| 3 | + |
| 4 | + |
| 5 | + |
| 6 | ++ |
| 7 | + |
| 8 | + |
| 9 | ++ |
| 10 | ++ |
| 11 | ++ |
| 12 | ++ |
| 13 | + |
| 14 | + |
| 15 | + |
| 16 | + |
| 17 | ++ |
| 18 | + |
| 19 | +++ |
| 20 | +++ |
| 21 | +++ |
| 22 | + |
| 23 | + |
| 24 | + |
| 25 | ++ |
| 26 | +++ |
| 27 | ++ |
| 28 | + |
| 29 | +++ |
| 30 | ++ |
| 31 | +++ |
| 32 | + |
| 33 | + |
| 34 | + |
| 35 | ++ |
| 36 | ++ |
| 37 | + |
| 38 | + |
| 39 | + |
| 40 | + |

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A compound of Formula (I):

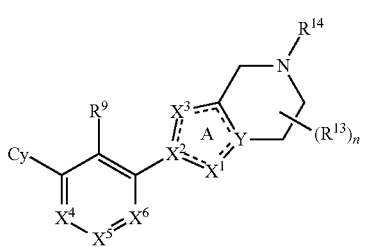

or a pharmaceutically acceptable salt or a stereoisomer thereof, wherein:
one of $X^1$ and $X^3$ is S and the other is N;
$X^2$ is C;
$X^4$ is N or $CR^4$;
$X^5$ is N or $CR^5$;
$X^6$ is N or $CR^6$;
Y is C;
Cy is $C_{6-10}$ aryl, $C_{3-10}$ cycloalkyl, 5- to 14-membered heteroaryl, or 4- to 10-membered heterocycloalkyl, each of which is optionally substituted with 1 to 5 independently selected $R^7$ substituents;
$R^4$, $R^5$ and $R^6$ are each independently selected from H, $C_{1-4}$ alkyl, $C_{3-4}$ cycloalkyl, $C_{2-4}$ alkenyl, $C_{2-4}$ alkynyl, halo, —CN, —OH, $C_{1-4}$ alkoxy, $C_{1-4}$ haloalkyl, $C_{1-4}$ haloalkoxy, —$NH_2$, —NH—$C_{1-4}$ alkyl, —N($C_{1-4}$ alkyl)$_2$, —$NHOR^{10}$, —$C(O)R^{10}$, —$C(O)R^{10}R^{10}$, —$C(O)OR^{10}$, —$OC(O)R^{10}$, —$OC(O)NR^{10}R^{10}$, —$NR^{10}C(O)R^{10}$, —$NR^{10}C(O)OR^{10}$, —$NR^{10}C(O)NR^{10}R^{10}$, —$C(=NR^{10})R^{10}$, —$C(=NR^{10})NR^{10}R^{10}$, —$NR^{10}C(=NR^{10})NR^{10}R^{10}$, —$NR^{10}S(O)R^{10}$, —$NR^{10}S(O)_2R^{10}$, —$NR^{10}S(O)_2NR^{10}R^{10}$, —$S(O)R^{10}$, —$S(O)NR^{10}R^{10}$, —$S(O)_2R^{10}$, and —$S(O)_2NR^{10}R^{10}$, wherein each $R^{10}$ is independently selected from H and $C_{1-4}$ alkyl optionally substituted with 1 or 2 groups independently selected from halo, —OH, —CN and $C_{1-4}$ alkoxy; and wherein the $C_{1-4}$ alkyl, $C_{3-4}$ cycloalkyl, $C_{2-4}$ alkenyl, $C_{2-4}$ alkynyl and $C_{1-4}$ alkoxy of $R^4$, $R^5$ and $R^6$ are each optionally substituted with 1 or 2 substituents independently selected from halo, —OH, —CN and $C_{1-4}$ alkoxy;
$R^9$ is $C_{1-4}$ alkyl, halo, or —CN;
$R^7$, $R^{13}$ and $R^{14}$ are each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, —CN, —$NO_2$, —$OR^a$, —$SR^a$, —$NHOR^a$, —$C(O)R^a$, —$C(O)NR^aR^a$, —$C(O)OR^a$, —$OC(O)R^a$, —$OC(O)NR^aR^a$, —$NHR^a$, —$NR^aR^a$, —$NR^aC(O)R^a$, —$NR^aC(O)OR^a$, —$NR^aC(O)NR^aR^a$, —$C(=NR^a)R^a$, —$C(=NR^a)NR^aR^a$, —$NR^aC(=NR^a)NR^aR^a$, —$NR^aS(O)R^a$, —$NR^aS(O)_2R^a$, —$NR^aS(O)_2NR^aR^a$, —$S(O)R^a$, —$S(O)NR^aR^a$, —$S(O)_2R^a$, and —$S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, and (4-10 membered heterocycloalkyl)-$C_{1-4}$ alkyl- of $R^7$, $R^{13}$ and $R^{14}$ are each optionally substituted with 1, 2, 3, or 4 $R^b$ substituents;
or two adjacent $R^7$ substituents on the Cy ring, taken together with the atoms to which they are attached, form a fused phenyl ring, a fused 5-, 6- or 7-membered heterocycloalkyl ring, a fused 5- or 6-membered heteroaryl ring or a fused $C_{3-6}$ cycloalkyl ring, wherein the fused 5-, 6- or 7-membered heterocycloalkyl ring and fused 5- or 6-membered heteroaryl ring each have 1-4 heteroatoms as ring members selected from N, O and S and wherein the fused phenyl ring, fused 5-, 6- or 7-membered heterocycloalkyl ring, fused 5- or 6-membered heteroaryl ring and fused $C_{3-6}$ cycloalkyl ring are each optionally substituted with 1, 2 or 3 independently selected $R^b$ substituents;
or two $R^{13}$ substituents attached to the same carbon atom, taken together with the carbon atom to which they are attached, form a $C_{3-6}$ cycloalkyl ring or 4-, 5-, 6- or 7-membered heterocycloalkyl ring, wherein the $C_{3-6}$ cycloalkyl ring and 4-, 5-, 6- or 7-membered heterocycloalkyl ring are each optionally substituted with 1, 2 or 3 independently selected $R^b$ substituents;
each $R^a$ is independently selected from H, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^a$ are each optionally substituted with 1, 2, 3, 4, or 5 $R^d$ substituents;
each $R^d$ is independently selected from $C_{1-4}$ alkyl, $C_{1-4}$ haloalkyl, halo, $C_{3-10}$ cycloalkyl, 4-10 membered heterocycloalkyl, —CN, —$NH_2$, —$NHOR^e$, —$OR^e$, —$SR^e$, —$C(O)R^e$, —$C(O)NR^eR^e$, —$C(O)OR^e$, —$OC(O)R^e$, —$OC(O)NR^eR^e$, —$NHR^e$, —$NR^eR^e$, —$NR^eC(O)R^e$, —$NR^eC(O)NR^eR^e$, —$NR^eC(O)OR^e$, —$C(=NR^e)NR^eR^e$, —$NR^eC(=NR^e)NR^eR^e$, —$S(O)R^e$, —$S(O)NR^eR^e$, —$S(O)_2R^e$, —$NR^eS(O)_2R^e$, —$NR^eS(O)_2NR^eR^e$, and —$S(O)_2NR^eR^e$, wherein the $C_{1-4}$ alkyl, $C_{3-10}$ cycloalkyl and 4-10 membered heterocycloalkyl of $R^d$ are each further optionally substituted with 1-3 independently selected $R^q$ substituents;
each $R^b$ substituent is independently selected from halo, $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, —CN, —OH, —$NH_2$, —$NO_2$, —$NHOR^c$, —$OR^c$, —$SR^c$, —$C(O)R^c$, —$C(O)NR^cR^c$, —$C(O)OR^c$, —$OC(O)R^c$, —$OC(O)NR^cR^c$, —$C(=NR^c)NR^cR^c$, —$NR^cC(=NR^c)NR^cR^c$, —$NHR^c$, —$NR^cR^c$, —$NR^cC(O)R^c$, —$NR^cC(O)OR^c$, —$NR^cC(O)NR^cR^c$, —$NR^cS(O)R^c$, —$NR^cS(O)_2R^c$, —$NR^c$ $S(O)_2NR^cR^c$, $-S(O)R^c$, $-S(O)NR^cR^c$, $-S(O)_2R^c$ and $-S(O)_2NR^cR^c$; wherein the $C_{1-4}$ alkyl, $C_{1-4}$ haloalkyl, $C_{1-4}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1-3 independently selected $R^d$ substituents;

each $R^c$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2, 3, 4, or 5 $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, $-CN$, $-NHOR^g$, $-OR^g$, $-SR^g$, $-C(O)R^g$, $-C(O)NR^gR^g$, $-C(O)OR^g$, $-OC(O)R^g$, $-OC(O)NR^gR^g$, $-NHR^g$, $-NR^gR^g$, $-NR^gC(O)R^g$, $-NR^gC(O)NR^gR^g$, $-NR^gC(O)OR^g$, $-C(=NR^g)NR^gR^g$, $-NR^gC(=NR^g)NR^gR^g$, $-S(O)R^g$, $-S(O)NR^gR^g$, $-S(O)_2R^g$, $-NR^gS(O)_2R^g$, $-NR^gS(O)_2NR^gR^g$, and $-S(O)_2NR^gR^g$; wherein the $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 Rn substituents independently selected from $C_{1-4}$ alkyl, $C_{1-4}$ haloalkyl, halo, $-CN$, $-NHOR^o$, $-OR^o$, $-SR^o$, $-C(O)R^o$, $-C(O)NR^oR^o$, $-C(O)OR^o$, $-OC(O)R^o$, $-OC(O)NR^oR^o$, $-NHR^o$, $-NR^oR^o$, $-NR^oC(O)R^o$, $-NR^oC(O)NR^oR^o$, $-NR^oC(O)OR^o$, $-C(=NR^oNR^oR^o$, $-NR^oC(=NR^oNR^oR^o$, $-S(O)R^o$, $-S(O)NR^oR^o$, $-S(O)_2R^o$, $-NR^oS(O)_2R^o$, $-NR^oS(O)_2NR^oR^o$, and $-S(O)_2NR^oR^o$;

each $R^g$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1-3 independently selected $R^p$ substituents;

or any two $R^a$ substituents together with the nitrogen atom to which they are attached form a 4-, 5-, 6-, 7-, 8-, 9- or 10-membered heterocycloalkyl group optionally substituted with 1, 2 or 3 $R^h$ substituents independently selected from $C_{1-6}$ alkyl, $C_{3-10}$ cycloalkyl, 4-7 membered heterocycloalkyl, $C_{6-10}$ aryl, 5-6 membered heteroaryl, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl-, $C_{1-6}$ haloalkyl, $C_{2-6}$ alkenyl, $C_{2-6}$ alkynyl, halo, $-CN$, $-OR^i$, $-SR^i$, $-NHOR^i$, $-C(O)R^i$, $-C(O)OR^i$, $-OC(O)R^i$, $-OC(O)NR^iR^i$, $-NHR^i$, $-NR^iR^i$, $-NR^iC(O)R^i$, $-NR^iC(O)NR^iR^i$, $-NR^iC(O)OR^i$, $-C(=NR^i)NR^iR^i$, $-NR^iC(=NR^i)NR^iR^i$, $-S(O)R^i$, $-S(O)_2R^i$, $-NR^iS(O)_2R^i$, $-NR^iS(O)_2NR^iR^i$, and $-S(O)_2NR^iR^i$, wherein the $C_{1-6}$ alkyl, $C_{3-10}$ cycloalkyl, 4-7 membered heterocycloalkyl, $C_{6-10}$ aryl, 5-6 membered heteroaryl, $C_{3-10}$ cycloalkyl-$C_{1-4}$ alkyl-, (5-6 membered heteroaryl)-$C_{1-4}$ alkyl-, (4-7 membered heterocycloalkyl)-$C_{1-4}$ alkyl- of $R^h$ are each further optionally substituted by 1, 2, or 3 $R^1$ substituents;

each $R^j$ is independently selected from $C_{3-6}$ cycloalkyl, $C_{6-10}$ aryl, 5 or 6-membered heteroaryl, $C_{2-4}$ alkenyl, $C_{2-4}$ alkynyl, halo, $C_{1-4}$ alkyl, $C_{1-4}$ haloalkyl, $-CN$, $-NHOR^k$, $-OR^k$, $-SR^k$, $-C(O)R^k$, $-C(O)NR^kR^k$, $-C(O)OR^k$, $-OC(O)R^k$, $-OC(O)NR^kR^k$, $-NHR^k$, $-NR^kR^k$, $-NR^kC(O)R^k$, $-NR^kC(O)NR^kR^k$, $-NR^kC(O)OR^k$, $-C(=NR^k)NR^kR^k$, $-NR^kC(=NR^k)NR^kR^k$, $-S(O)R^k$, $-S(O)NR^kR^k$, $-S(O)_2R^k$, $-NR^kS(O)_2R^k$, $-NR^kS(O)_2NR^kR^k$, and $-S(O)_2NR^kR^k$;

or two $R^h$ groups attached to the same carbon atom of the 4- to 10-membered heterocycloalkyl taken together with the carbon atom to which they are attached form a $C_{3-6}$ cycloalkyl or 4- to 6-membered heterocycloalkyl having 1-2 heteroatoms as ring members selected from O, N or S;

or any two RC substituents together with the nitrogen atom to which they are attached form a 4-, 5-, 6-, or 7-membered heterocycloalkyl group optionally substituted with 1, 2, or 3 independently selected $R^h$ substituents;

or any two $R^e$ substituents together with the nitrogen atom to which they are attached form a 4-, 5-, 6-, or 7-membered heterocycloalkyl group optionally substituted with 1, 2, or 3 independently selected $R^h$ substituents;

or any two $R^g$ substituents together with the nitrogen atom to which they are attached form a 4-, 5-, 6-, or 7-membered heterocycloalkyl group optionally substituted with 1, 2, or 3 independently selected $R^h$ substituents;

or any two $R^o$ substituents together with the nitrogen atom to which they are attached form a 4-, 5-, 6-, or 7-membered heterocycloalkyl group optionally substituted with 1, 2, or 3 independently selected $R^h$ substituents; and each $R^e$, $R^k$, $R^o$ or $R^p$ is independently selected from H, $C_{1-4}$ alkyl, $C_{3-6}$ cycloalkyl, $C_{6-10}$ aryl, 5 or 6-membered heteroaryl, $C_{1-4}$ haloalkyl, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, $C_{2-4}$ alkenyl, and $C_{2-4}$ alkynyl of $R^e$, $R^i$, $R^k$, $R^o$ or $R^p$ are each optionally substituted with 1, 2 or 3 $R^q$ substituents;

each $R^q$ is independently selected from $-OH$, $-CN$, $-COOH$, $-NH_2$, halo, $C_{1-6}$haloalkyl, $C_{1-6}$ alkyl, $C_{1-6}$ alkoxy, $C_{1-6}$ haloalkoxy, $C_{1-6}$ alkylthio, phenyl, 5-6 membered heteroaryl, 4-6 membered heterocycloalkyl, $C_{3-6}$ cycloalkyl, $-NHR^{12}$, $-NR^{12}R^{12}$, and $C_{1-4}$ haloalkoxy, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with halo, $-OH$, $-CN$, $-COOH$, $-NH_2$, $C_{1-4}$ alkoxy, $C_{1-4}$ haloalkyl, $C_{1-4}$ haloalkoxy, phenyl, $C_{3-10}$ cycloalkyl and 4-6 membered heterocycloalkyl;

each $R^{12}$ is independently $C_{1-6}$ alkyl;

----- is a single bond or a double bond to maintain ring A being aromatic; and the subscript n is an integer of 1, 2, 3, 4, 5 or 6.

2. The compound of claim 1, having Formula (II):

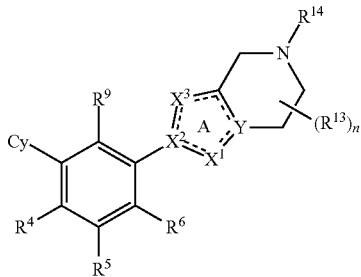

(II)

or a pharmaceutically acceptable salt or a stereoisomer thereof.

3. The compound of claim 2, or a pharmaceutically acceptable salt or a stereoisomer thereof, wherein $R^4$, $R^5$ and $R^6$ are each H.

4. The compound of claim 1, having Formula (III):

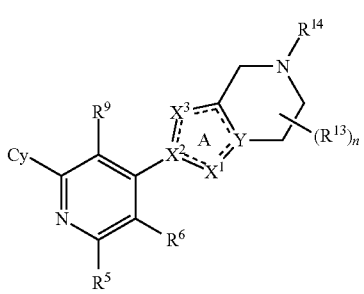

(III)

or a pharmaceutically acceptable salt or a stereoisomer thereof.

5. The compound of claim 1, having Formula (IV):

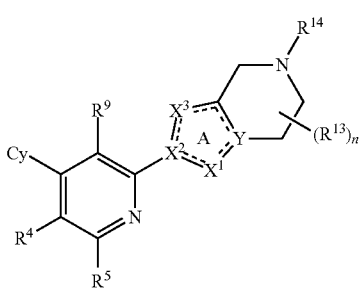

(IV)

or a pharmaceutically acceptable salt or a stereoisomer thereof.

6. The compound of claim 1, or a pharmaceutically acceptable salt or a stereoisomer thereof, wherein Cy is phenyl, 5- or 6-membered heteroaryl, $C_{3-6}$ cycloalkyl or 5- or 6-membered heterocycloalkyl, each of which is optionally substituted with 1 to 5 independently selected $R^7$ substituents.

7. The compound of claim 1, or a pharmaceutically acceptable salt or a stereoisomer thereof, wherein Cy is phenyl, 2-thiophenyl, 3-thiophenyl, 2-pyridyl, 3-pyridyl, 4-pyridyl, $C_{3-6}$ cycloalkyl or 3,6-dihydro-2H-pyran-4-yl, each of which is optionally substituted with 1 to 5 $R^7$ substituents.

8. The compound of claim 1, or a pharmaceutically acceptable salt or a stereoisomer thereof, wherein Cy is phenyl optionally substituted with 1 to 5 $R^7$ substituents.

9. The compound of claim 1, or a pharmaceutically acceptable salt or a stereoisomer thereof, wherein Cy is unsubstituted phenyl.

10. The compound of claim 1, having Formula (V):

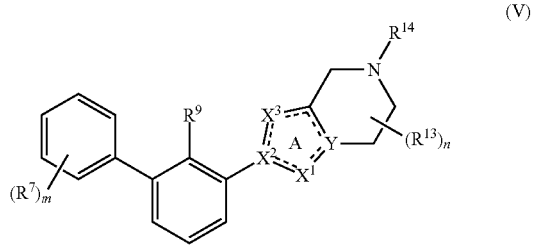

(V)

or a pharmaceutically acceptable salt or a stereoisomer thereof, wherein the subscript m is an integer of 1, 2, 3, 4 or 5.

11. The compound of claim 1, having Formula (VI):

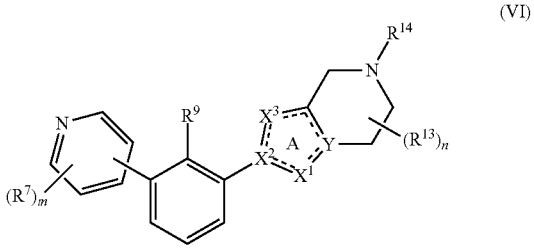

(VI)

or a pharmaceutically acceptable salt or a stereoisomer thereof, wherein m is an integer of 1, 2, 3 or 4.

12. The compound of claim 1, having Formula (VII):

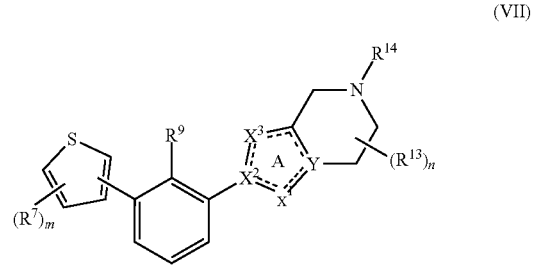

(VII)

or a pharmaceutically acceptable salt or a stereoisomer thereof, wherein m is an integer of 1, 2 or 3.

13. The compound of claim 1, or a pharmaceutically acceptable salt or a stereoisomer thereof, wherein $R^9$ is —$CH_3$, —CN or halo.

14. The compound of claim 1, or a pharmaceutically acceptable salt or a stereoisomer thereof, wherein $X^1$ is N, $X^2$ is C, $X^3$ is S, and Y is C.

15. The compound of claim 1, or a pharmaceutically acceptable salt or a stereoisomer thereof, wherein $X^1$ is S, $X^2$ is C, $X^3$ is N, and Y is C.

16. The compound of claim 1, or a pharmaceutically acceptable salt or a stereoisomer thereof, wherein $X^1$ is N, $X^2$ is C, $X^3$ is S, $X^6$ is N, and Y is C.

17. The compound of claim 1, or a pharmaceutically acceptable salt or a stereoisomer thereof, wherein $X^1$ is N, $X^2$ is C, $X^3$ is S, $X^4$ is N, and Y is C.

18. The compound of claim 1, or a pharmaceutically acceptable salt or a stereoisomer thereof, wherein $R^4$, $R^5$ and $R^6$ when present are each H.

19. The compound of claim 1, or a pharmaceutically acceptable salt or a stereoisomer thereof, wherein $R^{14}$ is 2-hydroxyethyl, 2-hydroxypropyl, (R)-2-hydroxypropyl, (S)-2-hydroxypropyl, tetrahydro-2H-pyran-4-yl, 4-carboxycyclohexyl, 3-carboxypropyl, 2-carboxycyclopropylmethyl, 1H-pyrazol-4-ylmethyl or 4-cyanomethylcyclohexyl.

20. The compound of claim 1, or a pharmaceutically acceptable salt or a stereoisomer thereof, wherein $R^{13}$ is H or $C_{1-6}$ alkyl.

21. The compound of claim 1, or a pharmaceutically acceptable salt thereof, wherein the compound is selected from:

2-(2-methylbiphenyl-3-yl)-4,5,6,7-tetrahydro[1,3]thiazolo[4,5-c]pyridine;

2-(2-methylbiphenyl-3-yl)-4,5,6,7-tetrahydro[1,3]thiazolo[5,4-c]pyridine;

5-methyl-2-(2-methylbiphenyl-3-yl)-4,5,6,7-tetrahydro[1,3]thiazolo[5,4-c]pyridine;

2-[2-(2-methylbiphenyl-3-yl)-6,7-dihydro[1,3]thiazolo[5,4-c]pyridin-5(4H)-yl]ethanol;

(2S)-1-[2-(2-methylbiphenyl-3-yl)-6,7-dihydro[1,3]thiazolo[5,4-c]pyridin-5(4H)-yl]propan-2-ol;

2-(2-methylbiphenyl-3-yl)-5-(tetrahydro-2H-pyran-4-yl)-4,5,6,7-tetrahydro[1,3]thiazolo[5,4-c]pyridine;

4-[2-(2-methylbiphenyl-3-yl)-6,7-dihydro[1,3]thiazolo[5,4-c]pyridin-5(4H)-yl]cyclohexanecarboxylic acid;

4-[2-(2-methylbiphenyl-3-yl)-6,7-dihydro[1,3]thiazolo[5,4-c]pyridin-5(4H)-yl]butanoic acid;

trans-2-{[2-(2-methylbiphenyl-3-yl)-6,7-dihydro[1,3]thiazolo[5,4-c]pyridin-5 (4H)-yl] methyl}cyclopropanecarboxylic acid;

2-(2-methylbiphenyl-3-yl)-5-(1H-pyrazol-4-ylmethyl)-4,5,6,7-tetrahydro[1,3]thiazolo[5,4-c]pyridine;

{4-[2-(2-methylbiphenyl-3-yl)-6,7-dihydro[1,3]thiazolo[5,4-c]pyridin-5(4H)-yl]cyclohexyl}acetonitrile;

2-(2,3-dihydro-1,4-benzodioxin-6-yl)-6-(4,5,6,7-tetrahydro[1,3]thiazolo[5,4-c]pyridin-2-yl)benzonitrile;

2-(3-methyl-4-phenylpyridin-2-yl)-4,5,6,7-tetrahydro[1,3]thiazolo[5,4-c]pyridine;

2-[4-(3-methoxyphenyl)-3-methylpyridin-2-yl]-4,5,6,7-tetrahydro[1,3]thiazolo[5,4-c]pyridine;

2-[4-(2,3-dihydro-1,4-benzodioxin-6-yl)-3-methylpyridin-2-yl]-4,5,6,7-tetrahydro[1,3]thiazolo[5,4-c]pyridine;

7,7-dimethyl-2-(2-methylbiphenyl-3-yl)-4,5,6,7-tetrahydro[1,3]thiazolo[5,4-c]pyridine;

2-[2-(2,3-dihydro-1,4-benzodioxin-6-yl)-3-methylpyridin-4-yl]-4,5,6,7-tetrahydro[1,3]thiazolo[5,4-c]pyridine;

2-[2-methyl-3-(3-thienyl)phenyl]-4,5,6,7-tetrahydro[1,3]thiazolo[5,4-c]pyridine;

2-(3'-methoxy-2-methylbiphenyl-3-yl)-4,5,6,7-tetrahydro[1,3]thiazolo[5,4-c]pyridine;

2-[3-(3,6-dihydro-2H-pyran-4-yl)-2-methylphenyl]-4,5,6,7-tetrahydro[1,3]thiazolo[5,4-c]pyridine;

2-[3-(2-methoxypyridin-4-yl)-2-methylphenyl]-4,5,6,7-tetrahydro[1,3]thiazolo[5,4-c]pyridine;

2-[3-(5-fluoropyridin-2-yl)-2-methylphenyl]-4,5,6,7-tetrahydro[1,3]thiazolo[5,4-c]pyridine;

2-(3-cyclohex-1-en-1-yl-2-methylphenyl)-4,5,6,7-tetrahydro[1,3]thiazolo[5,4-c]pyridine;

2-(3'-ethoxy-2-methylbiphenyl-3-yl)-4,5,6,7-tetrahydro[1,3]thiazolo[5,4-c]pyridine;

2-(3',5'-dimethoxy-2-methylbiphenyl-3-yl)-4,5,6,7-tetrahydro[1,3]thiazolo[5,4-c]pyridine;

4-(2,3-dihydro-1,4-benzodioxin-6-yl)-2-(4,5,6,7-tetrahydro[1,3]thiazolo[5,4-c]pyridin-2-yl)nicotinonitrile;

2-{[2'-methyl-3'-(4,5,6,7-tetrahydro[1,3]thiazolo[5,4-c]pyridin-2-yl)biphenyl-3-yl]oxy}ethanol;

2-(2',6'-difluoro-3',5'-dimethoxy-2-methylbiphenyl-3-yl)-4,5,6,7-tetrahydro[1,3]thiazolo[5,4-c]pyridine;

2'-methyl-3'-(4,5,6,7-tetrahydro[1,3]thiazolo[5,4-c]pyridin-2-yl)biphenyl-3-carboxamide;

2-[2'-methyl-3'-(4,5,6,7-tetrahydro[1,3]thiazolo[5,4-c]pyridin-2-yl)biphenyl-3-yl]acetamide; and 2-[2-methyl-3-(1-methyl-1H-indazol-4-yl)phenyl]-4,5,6,7-tetrahydro[1,3]thiazolo[5,4-c]pyridine.

22. A pharmaceutical composition comprising a compound of claim 1, or a pharmaceutically acceptable salt or a stereoisomer thereof, and at least one pharmaceutically acceptable carrier or excipient.

* * * * *

UNITED STATES PATENT AND TRADEMARK OFFICE
CERTIFICATE OF CORRECTION

PATENT NO. : 11,608,337 B2
APPLICATION NO. : 17/032603
DATED : March 21, 2023
INVENTOR(S) : Zhenwu Li, Liangxing Wu and Wenqing Yao It is certified that error appears in the above-identified patent and that said Letters Patent is hereby corrected as shown below:

In the Claims

Column 77, Line 40, Claim 1, delete "—C(O)R$^{10}$R$^{10}$," and insert -- —C(O)NR$^{10}$R$^{10}$, --;

Column 79, Line 41, Claim 1, delete "Rn" and insert -- R$^n$ --;

Column 79, Lines 46-47, Claim 1, delete "—C(=NR$^o$NR$^o$R$^o$," and insert -- —C(=NR$^o$)NR$^o$R$^o$, --;

Column 79, Line 47, Claim 1, delete "—NR$^o$C(=NR$^o$NR$^o$R$^o$," and insert -- —NR$^o$C(=NR$^o$)NR$^o$R$^o$, --;

Column 80, Line 17, Claim 1, delete "R$^1$" and insert -- R$^j$ --;

Column 80, Line 34, Claim 1, delete "RC" and insert -- R$^c$ --;

Column 80, Line 52, Claim 1, after "R$^e$," insert -- R$^i$, --;

Column 80, Line 60, Claim 1, delete "C$_{1-6}$haloalkyl," and insert -- C$_{1-6}$ haloalkyl, --.

Signed and Sealed this
Twenty-seventh Day of February, 2024

Katherine Kelly Vidal
*Director of the United States Patent and Trademark Office*